United States Patent
Phan et al.

(10) Patent No.: US 11,737,694 B2
(45) Date of Patent: *Aug. 29, 2023

(54) PERSONAL DIAGNOSTIC DEVICE HAVING A PLURALITY OF TUBULES

(71) Applicant: Life Patch International, Irvine, CA (US)

(72) Inventors: Brigitte Chau Phan, Irvine, CA (US); Andrew Atilla Pal, San Diego, CA (US); Ramoncito M. Valencia, Aliso Viejo, CA (US); Donald Bollella, Irvine, CA (US)

(73) Assignee: Life Patch International, Inc., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/994,831

(22) Filed: May 31, 2018

(65) Prior Publication Data
US 2018/0344230 A1  Dec. 6, 2018

Related U.S. Application Data

(63) Continuation of application No. 14/853,523, filed on Sep. 14, 2015, now Pat. No. 9,993,189, which is a (Continued)

(51) Int. Cl.
*A61B 5/15* (2006.01)
*A61B 5/145* (2006.01)
(Continued)

(52) U.S. Cl.
CPC ...... *A61B 5/150969* (2013.01); *A61B 5/0002* (2013.01); *A61B 5/0022* (2013.01);
(Continued)

(58) Field of Classification Search
CPC ............ A61B 2560/0412; A61B 5/145; A61B 5/150221; A61B 5/150251;
(Continued)

(56) References Cited

U.S. PATENT DOCUMENTS 3,654,090 A 4/1972 Schuurs et al.
3,874,852 A 4/1975 Hamill
(Continued)

FOREIGN PATENT DOCUMENTS

CN 1262606 A 8/2000
EP 0428197 A2 5/1991
(Continued)

OTHER PUBLICATIONS

Lee, Y. et al., Flow Characteristics of Hydrophilic/Hydrophobic Capillaries Considering Surface Tension, May 2-4, 2002, Madison, Wisconsin, IEEE.
(Continued)

*Primary Examiner* — Robert T. Crow
(74) *Attorney, Agent, or Firm* — Knobbe, Martens, Olson & Bear, LLP

(57) ABSTRACT

Personal diagnostic devices including diagnostic patches (bio-patches) and interactive medical bracelets (bio-bracelets) are provided with a skin/patch interface, at least one analysis layer, a signal processing layer, and a user output interface. Embodiments of the interactive diagnostic devices may include micro-fluidic circuits with reaction chambers, analysis chambers, mixing cambers, and various pre-disposed chemistries or reagents for performing a wide verity of tests by transdermal transport of blood or perspiration. Sample collection chambers for the fluidic circuit may include minimally invasive tubules that penetrate the skin surface to acquire blood samples from capillaries near the epidermis. Alternate implementations of the personal diag-
(Continued)

nostic device may be equipped with logic processing, input/output devices, acoustic microphones, cryogenic circuits, embedded processors, electrical control circuitry, and battery current sources or photovoltaic sources of electrical power.

20 Claims, 50 Drawing Sheets

Related U.S. Application Data continuation of application No. 10/934,665, filed on Sep. 2, 2004, now Pat. No. 9,133,024.

(60) Provisional application No. 60/510,769, filed on Oct. 11, 2003, provisional application No. 60/500,102, filed on Sep. 3, 2003.

(51) Int. Cl.
| | |
|---|---|
| *A61B 5/00* | (2006.01) |
| *A61B 5/11* | (2006.01) |
| *A61B 5/1486* | (2006.01) |
| *B01L 3/00* | (2006.01) |
| *B82Y 15/00* | (2011.01) |
| *G01N 33/52* | (2006.01) |
| *A61B 5/151* | (2006.01) |
| *B82Y 30/00* | (2011.01) |
| *A61B 5/157* | (2006.01) |
| *A61B 5/1455* | (2006.01) |

(52) U.S. Cl.
CPC ............ *A61B 5/1112* (2013.01); *A61B 5/145* (2013.01); *A61B 5/1455* (2013.01); *A61B 5/1486* (2013.01); *A61B 5/14514* (2013.01); *A61B 5/14521* (2013.01); *A61B 5/14532* (2013.01); *A61B 5/14546* (2013.01); *A61B 5/151* (2013.01); *A61B 5/157* (2013.01); *A61B 5/150022* (2013.01); *A61B 5/15087* (2013.01); *A61B 5/150213* (2013.01); *A61B 5/150221* (2013.01); *A61B 5/150251* (2013.01); *A61B 5/150358* (2013.01); *A61B 5/150389* (2013.01); *A61B 5/150755* (2013.01); *A61B 5/150984* (2013.01); *A61B 5/4839* (2013.01); *A61B 5/681* (2013.01); *A61B 5/6833* (2013.01); *A61B 5/72* (2013.01); *A61B 5/7475* (2013.01); *B01L 3/50273* (2013.01); *B01L 3/502738* (2013.01); *B01L 3/502746* (2013.01); *B82Y 15/00* (2013.01); *B82Y 30/00* (2013.01); *G01N 33/528* (2013.01); *A61B 5/1411* (2013.01); *A61B 2505/07* (2013.01); *A61B 2560/0214* (2013.01); *A61B 2560/0412* (2013.01); *A61B 2562/028* (2013.01); *A61B 2562/0285* (2013.01); *A61B 2562/0295* (2013.01); *B01L 2200/10* (2013.01); *B01L 2200/12* (2013.01); *B01L 2200/143* (2013.01); *B01L 2300/023* (2013.01); *B01L 2300/027* (2013.01); *B01L 2300/069* (2013.01); *B01L 2300/0636* (2013.01); *B01L 2300/0681* (2013.01); *B01L 2300/087* (2013.01); *B01L 2300/0816* (2013.01); *B01L 2300/0887* (2013.01); *B01L 2400/049* (2013.01); *B01L 2400/0655* (2013.01); *B01L 2400/0677* (2013.01)

(58) Field of Classification Search
CPC . A61B 5/150389; A61B 5/157; A61B 5/4839; A61B 5/6833; A61B 5/72; A61B 5/14532; A61B 2562/0295; A61B 5/0002; A61B 5/14514; A61B 5/150969; A61B 2505/07; A61B 5/1486; A61B 5/150022; A61B 5/681; B01L 2200/10; B01L 2300/087; B01L 2300/0887; B01L 3/502738
See application file for complete search history.

(56) References Cited

U.S. PATENT DOCUMENTS

| | | |
|---|---|---|
| 3,940,475 A | 2/1976 | Gross |
| 4,066,512 A | 1/1978 | Lai et al. |
| 4,286,963 A | 9/1981 | Ledis et al. |
| 4,346,018 A | 8/1982 | Carter et al. |
| 4,485,175 A | 11/1984 | Ledis et al. |
| 4,528,274 A | 7/1985 | Carter et al. |
| 4,683,195 A | 7/1987 | Mullis et al. |
| 4,683,202 A | 7/1987 | Mullis |
| 4,732,153 A | 3/1988 | Phillips |
| 4,751,179 A | 6/1988 | Ledis et al. |
| 4,821,733 A | 4/1989 | Peck |
| 4,846,182 A | 7/1989 | Fogt et al. |
| 5,114,864 A | 5/1992 | Walt |
| 5,443,080 A | 8/1995 | D'Angelo et al. |
| 5,458,140 A | 10/1995 | Eppstein et al. |
| 5,676,144 A | 10/1997 | Schoendorfer |
| 5,731,206 A | 3/1998 | Ledis et al. |
| 6,223,074 B1 | 4/2001 | Granger |
| 6,251,083 B1 | 6/2001 | Yum et al. |
| 6,379,324 B1 | 4/2002 | Gartstein et al. |
| 6,424,847 B1 | 7/2002 | Mastrototaro et al. |
| 6,479,015 B1 | 11/2002 | Long et al. |
| 6,585,646 B2 | 7/2003 | Berlin |
| 6,882,051 B2 | 4/2005 | Majumdar et al. |
| 6,887,202 B2 | 5/2005 | Currie et al. |
| 7,004,928 B2 * | 2/2006 | Aceti ................ A61B 5/14532 604/191 |
| 7,364,896 B2 | 4/2008 | Schembri |
| 9,133,024 B2 * | 9/2015 | Phan ................ B01L 3/502738 |
| 9,993,189 B2 * | 6/2018 | Phan ................ B01L 3/502738 |
| 2002/0004640 A1 | 1/2002 | Conn et al. |
| 2002/0037499 A1 | 3/2002 | Quake et al. |
| 2002/0065453 A1 | 5/2002 | Lesho et al. |
| 2002/0091312 A1 | 7/2002 | Berner et al. |
| 2002/0099308 A1 | 7/2002 | Bojan et al. |
| 2002/0124879 A1 | 9/2002 | Kaplan et al. |
| 2002/0138049 A1 | 9/2002 | Allen et al. |
| 2003/0065294 A1 | 4/2003 | Pickup et al. |
| 2003/0153900 A1 * | 8/2003 | Aceti ............... A61B 5/150076 604/890.1 |
| 2003/0199811 A1 * | 10/2003 | Sage, Jr. ............... A61B 17/205 604/46 |
| 2003/0208113 A1 | 11/2003 | Mault et al. |
| 2003/0225362 A1 * | 12/2003 | Currie ................. A61B 5/0059 604/20 |
| 2003/0229276 A1 | 12/2003 | Sarussi et al. |
| 2004/0087916 A1 | 5/2004 | Pickup et al. |
| 2004/0094733 A1 * | 5/2004 | Hower ............... A61B 5/14514 251/11 |
| 2004/0096959 A1 | 5/2004 | Stiene et al. |
| 2004/0181196 A1 | 9/2004 | Pickup et al. |
| 2004/0200909 A1 | 10/2004 | McMillan et al. |

FOREIGN PATENT DOCUMENTS

| | | |
|---|---|---|
| EP | 1262559 | 12/2002 |
| JP | 10-305016 | 11/1998 |
| JP | 2002-527177 | 8/2002 |
| WO | WO 98/024366 | 6/1998 |
| WO | WO 00/004832 | 2/2000 |

(56) References Cited

FOREIGN PATENT DOCUMENTS

WO WO 01/091626 12/2001
WO WO 02/049507 6/2002

OTHER PUBLICATIONS

Petrovick, Mathew, et al., The Role of Personal Monitors in Environmental and Health Effects Research, NAECON 1974 Record, pp. 153-159.
Adner, Marvin M. and Shirey, Terry; Point-of-Care Testing in Sports Medicine, Chap. 30, pp. 303-307, from Point-of-Care Testing, $2^{nd}$ edition, Jan. 2004, edited by Christopher P. Price, Andrew St. John, and Jocelyn M. Hicks, AACC Press, Washington DC, USA.
Ambros-Ingerson, Jose; Granger, Richard; and Lynch, Gary; Simulation of Paleocortex Performs Hierarchical Clustering, Mar. 16, 1990, Science, vol. 247, pp. 1344-1348.
Benvenuto, James; Jin, Yi; Casale, Malcolm; Lynch, Gary; Granger, Richard; Identification of Diagnostic Evoked Response Potential Segments in Alzheimer's Disease, Mar. 20, 2002, Experimental Neurology, vol. 176, pp. 269-276.
Cuatrecasas, Pedro and Anfinsen, Christian B.; Affinity Chromatography, 1971, Methods in Enzymology edited by Sidney P. Colowiek and Nathan O. Kaplan, No. 31, vol. 22, pp. 345-378.
Elion, Elaine A.; Constructing Recombinant DNA Molecules by the Polymerase Chain Reaction, Unit 3.17 from Current Protocols in Molecular Biology, 1993, edited by Virginia Benson Chanda, vol. 1, Supp. 24, John Wiley & Sons.
Erlich, H.A.; Gelfand, D.H.; and Saiki, R.K.; Specific DNA Amplification, Feb. 4, 1988, Nature, vol. 331, pp. 461-462.
Erlich, Henry A., editor PCR Technology: Principles and Applications for DNA Amplification, 1992, Part Chaps. 1, 4, 5, 6, 14, and 19, W.H. Freeman and Company, New York, USA.
Fraser, Callum G.; Analytical Performance Requirements for Point-of-Care Testing, Chap. 8, pp. 95-100, from Point-of-Care Testing, 2nd edition, Jan. 2004, edited by Christopher P. Price, Andrew St. John, and Jocelyn M. Hicks, AACC Press, Washington DC, USA.
Hardy, Robert W. and Hortin, Glen L.; Point-of-Care Testing in Patient Transportation Settings, Chap. 23, pp. 221-225, from Point-of-Care Testing, 2nd edition, Jan. 2004, edited by Christopher P. Price, Andrew St. John, and Jocelyn M. Hicks, AACC Press, Washington DC, USA.
Krentz, Andrew J.; Olufadi, Rasaq; and Byrne, Christopher D.; Pointof-Care Testing in Diabetes Mellitus, Chap. 31, pp. 309-322, from Point-of-Care Testing, 2nd edition, Jan. 2004, edited by Christopher P. Price, Andrew St. John, and Jocelyn M. Hicks, AACC Press, Washington DC, USA.
Kricka, Larry J.; Miniaturization Technology Chap. 6, pp. 71-83, from Point-of-Care Testing, 2nd edition, Jan. 2004, edited by Christopher P. Price, Andrew St. John, and Jocelyn M. Hicks, AACC Press, Washington DC, USA.
Lehmann, Craig A.; Point-of-care Testing in the Home via Telehealth, Chap. 27, pp. 269-277, from Point-of-Care Testing, $2^{nd}$ edition, Jan. 2004, edited by Christopher P. Price, Andrew St. John, and Jocelyn M. Hicks, AACC Press, Washington DC, USA.
Melrose, G.J.H.; Insolubilized Enzymes: Biochemical Applications of Synthetic Polymers from Reviews of Pure and Applied Chemistry, Jun. 1971, vol. 21, pp. 83-119.

Mullis, K. B. and Faloona, F. A.; Specific Synthesis of DNA in Vitro via a Polymerase-Catalyzed Chain Reaction, 1987, Methods in Enzymology, vol. 155, pp. 335-350.
Pearson, M. Joan and Barnes, Ian C.; Approaches to Delivering a Laboratory Medicine Service: Distributed Laboratory Services, Chap. 7, pp. 85-94, from Point-of-Care Testing, 2nd edition, Jan. 2004, edited by Christopher P. Price, Andrew St. John, and Jocelyn M. Hicks, AACC Press, Washington DC, USA.
Peterson, Alexander W.; Heaton, Richard J.; and Georgiadis, Rosina M.; The Effect of Surface Probe Density on DNA Hybridization, Nucleic Acid Research, 2001, vol. 29, No. 24, pp. 5163-5168.
Piette, John D.; The Patient Interface and Point-of-Care Testing, Chap. 19, pp. 187-196, from Point-of-Care Testing, 2nd edition, Jan. 2004, edited by Christopher P. Price, Andrew St. John, and Jocelyn M. Hicks, AACC Press, Washington DC, USA.
Price, Christopher P.; St. John, Andrew; and Hicks, Jocelyn M.; Point-of-Care Testing: VVhat, Why, When, and Where? Chap. 1, pp. 3-9, from Point-of-Care Testing, 2nd edition, Jan. 2004, edited by Christopher P. Price, Andrew St. John, and Jocelyn M. Hicks, AACC Press, Washington DC, USA.
Pugia, Michael J. and Price, Christopher P.; Technology of Handheld Devices for Point-of-Care Testing, Chap. 2, pp. 13-30, from Pointof-Care Testing, 2nd edition, Jan. 2004, edited by Christopher P. Price, Andrew St. John, and Jocelyn M. Hicks, AACC Press, Washington DC, USA.
Rebec, Mihailo V.; Houlne, Michael P.; Benson, Thomas P.; Carpenter, Scott E.; Parker, Donald R.; and Ripley, Paul M.; Noninvasive Technology for Point-of-Care Testing, Chap. 4, pp. 47-60, from Point-of-Care Testing, 2nd edition, Jan. 2004, edited by Christopher P. Price, Andrew St. John, and Jocelyn M. Hicks, AACC Press, Washington DC, USA.
Saiki, Randall K.; Bugawan, Teodorica L.; Horn, Glenn T.; Mullis, Kary B.; and Erlich, Henry A.; Analysis of Enzymatically Amplified ß-Globin and HLA-DQ-a DNA with Allele-Specific Oligonucleotide Probes, Nov. 13, 1986, Nature, vol. 324, pp. 163-166.
Saiki, Randall K.; Gelfand, David H.; Stoffel, Susanne; Schraf, Stephen J.; Higuchi, Russell; Horn, Glenn T.; Mullis, Kary B.; and Erlich, Henry A.; Primer-Directed Enzymatic Amplification of DNA with a Thermostable DNA Polymerase, Jan. 29, 1988, Science, vol. 239, pp. 487-491.
Saiki, Randall K; Schraf, Stephen; Faloona, Fred; Mullis, Kary B.; Horn, Glenn T.; Erlich, Henry A.; andArnheim, Norman; Enzymatic Amplification of ß-Globin Genomic Sequences and Restriction Site Analysis for Diagnosis of Sickle Cell Anemia, Dec. 20, 1985, Science, vol. 230,pp. 1350-1354.
Schmiechen, Nathan J.; Han Caroline; and Milzman, David P.; ED Use of Rapid Lactate to Evaluate Patients with Acute Chest Pain, Nov. 1997, Annals of Emergency Medicine, vol. 30, pp. 571-577.
Silman, Israel H. and Katchalski, Ephraim; Water-Insoluble Derivatives of Enzymes, Antigens, and Antibodies, Annual Review of Biochemistry, 1966, vol. 35, pp. 873-908.
Woodman, Anthony C. and Fend, Reinhard; Electronic-Noise Technology: Potential Applications in Point-of-Care Clinical Diagnosis and Management, Chap. 5, pp. 61-70, from Point-of-Care Testing, 2nd edition, Jan. 2004, edited by Christopher P. Price, Andrew St. John, and Jocelyn M. Hicks, AACC Press, Washington DC, USA.

* cited by examiner

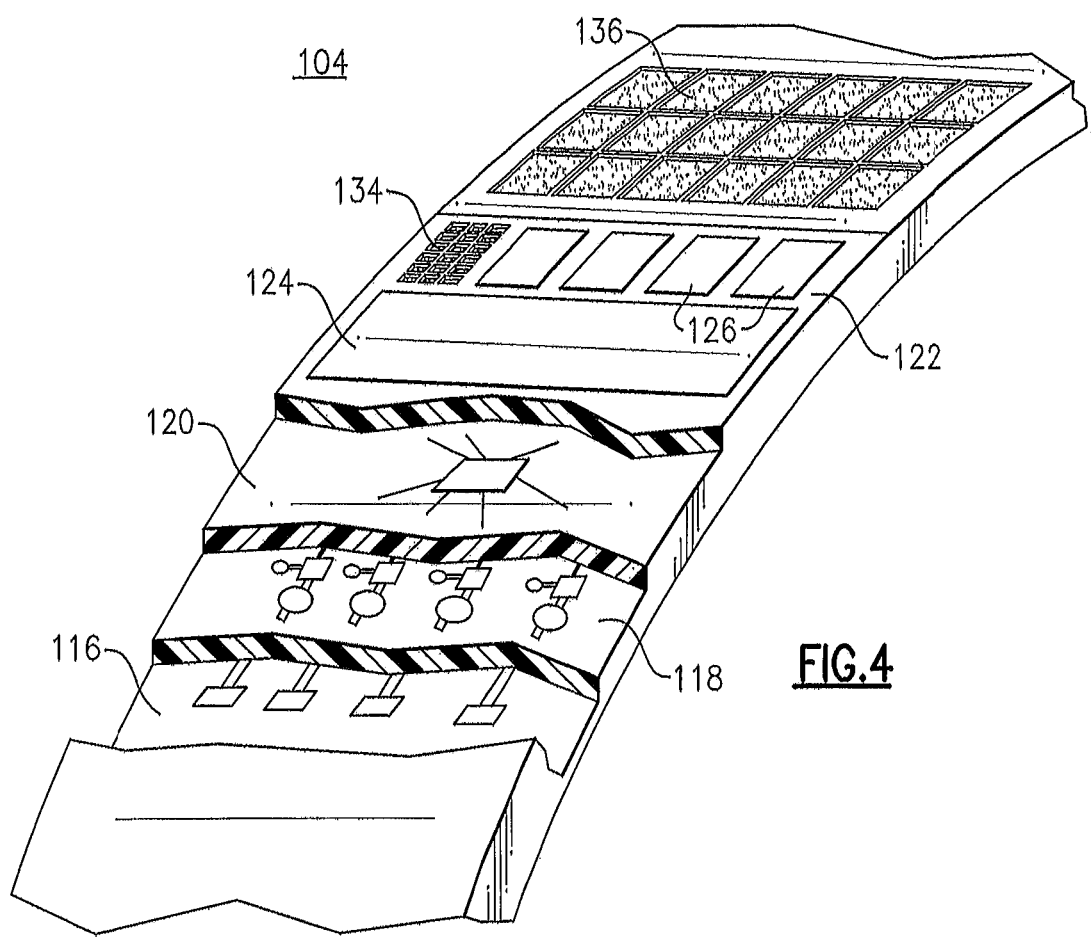

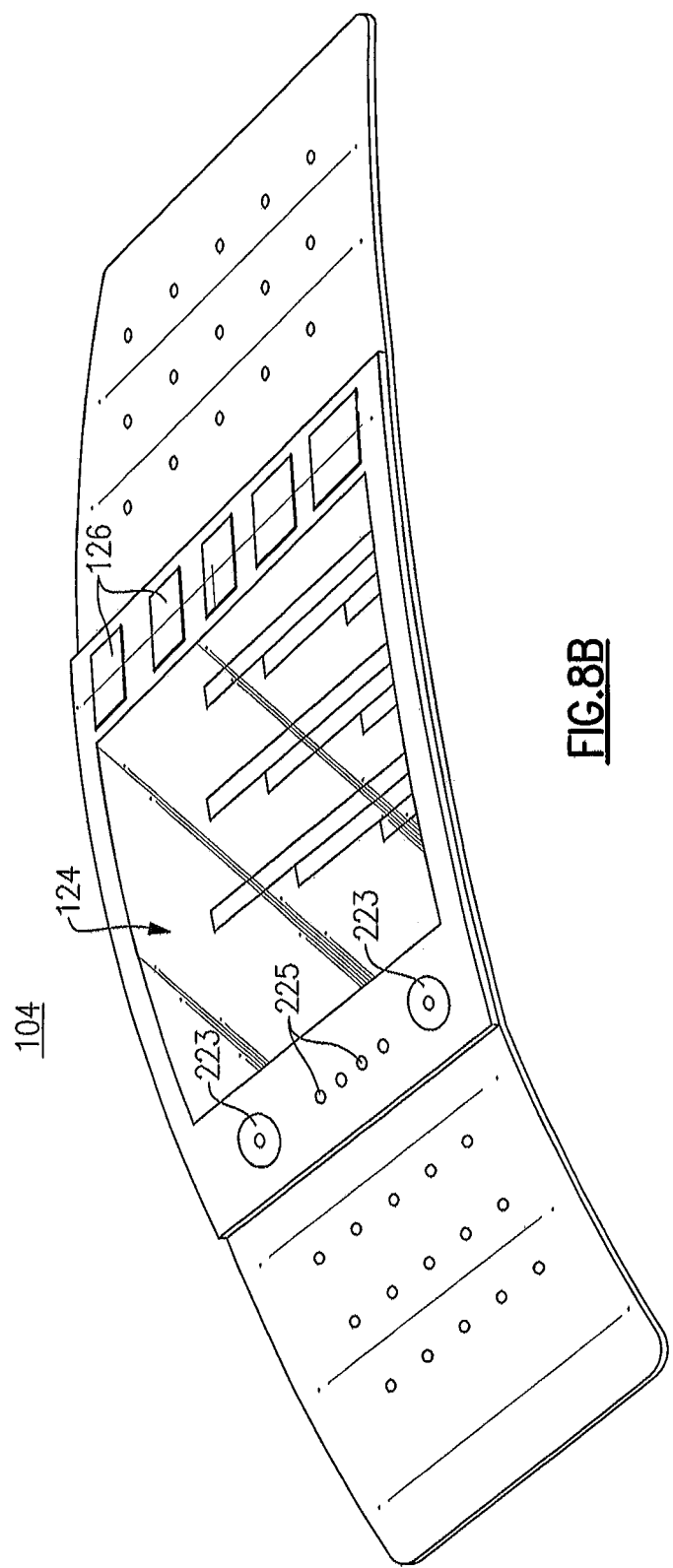

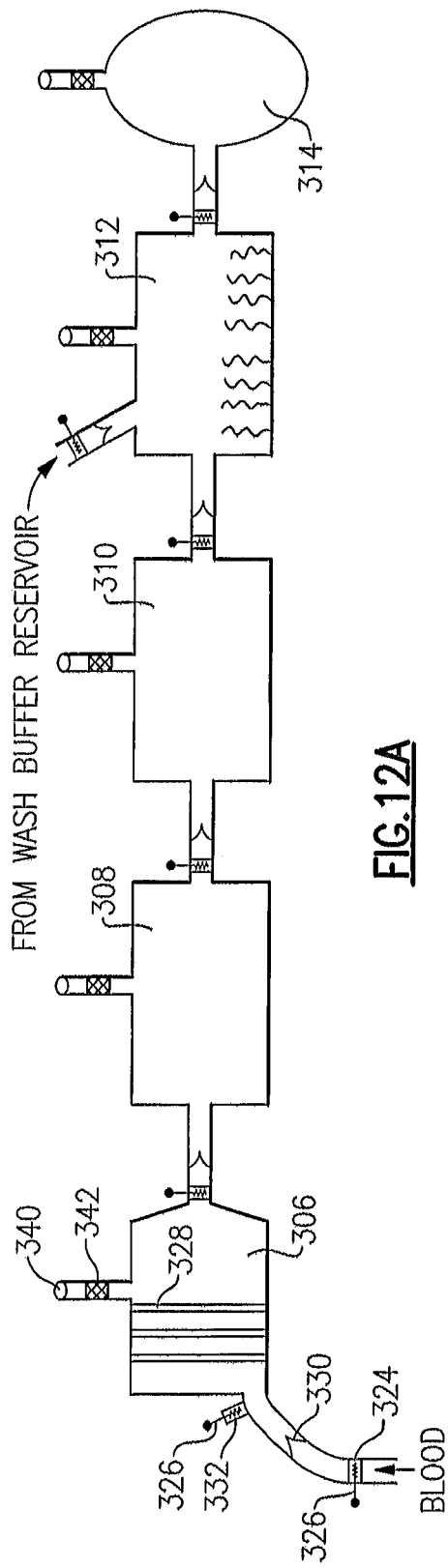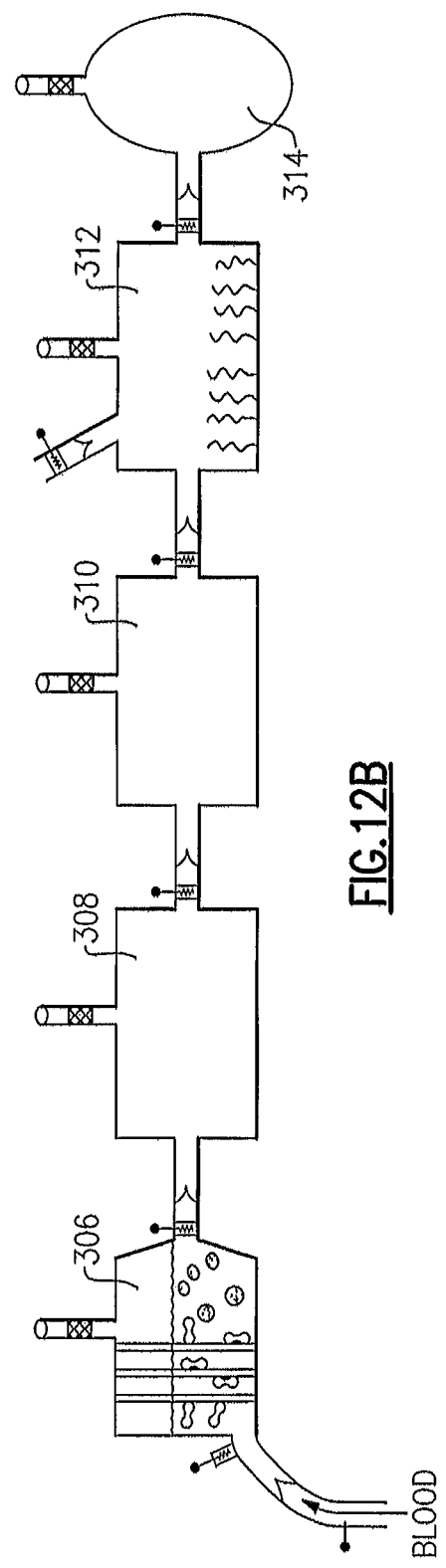
FIG.12A
FIG.12B

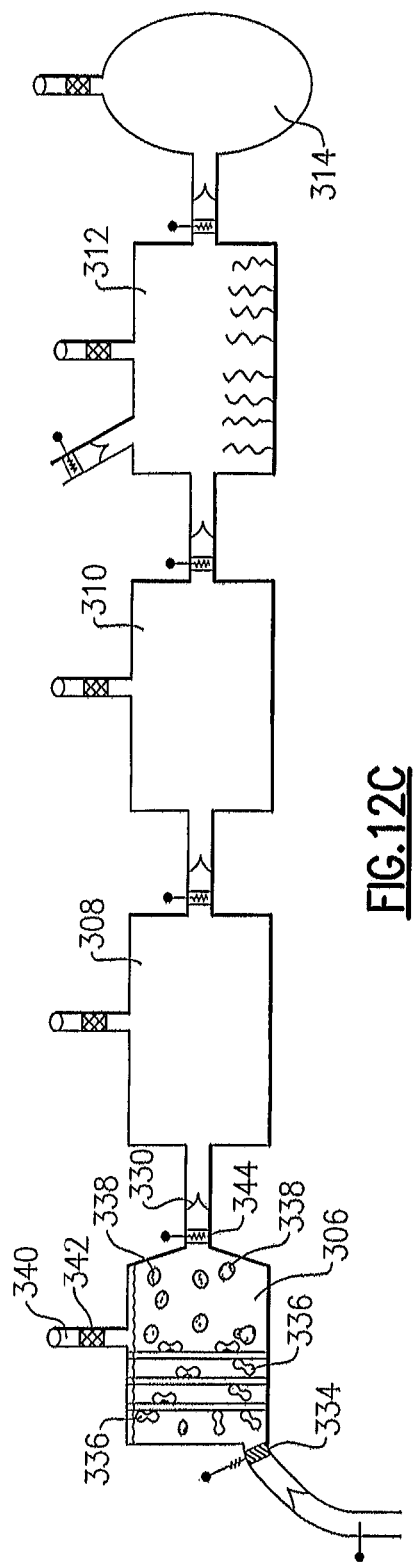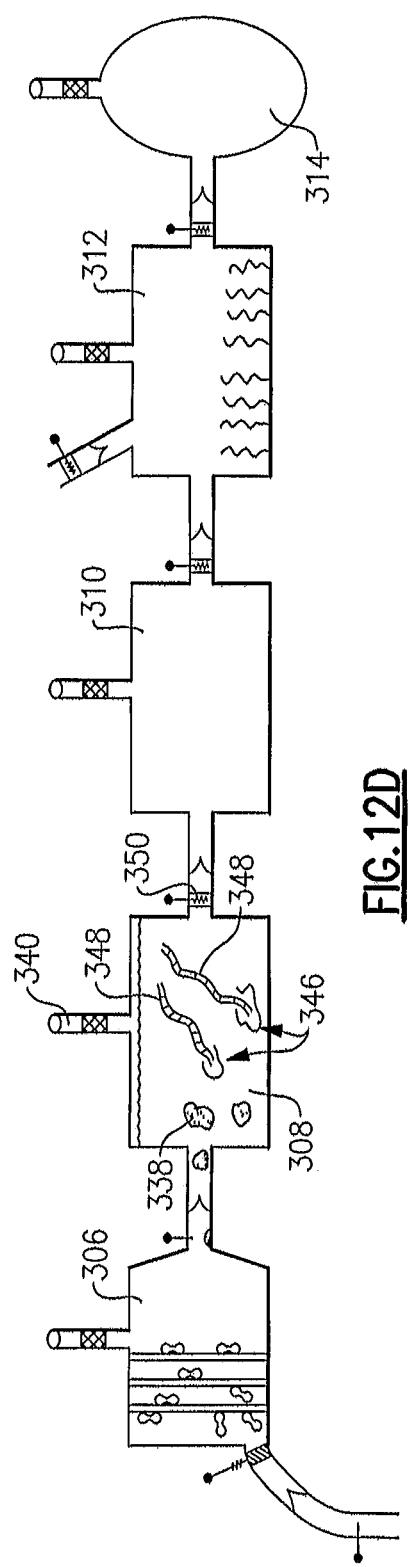

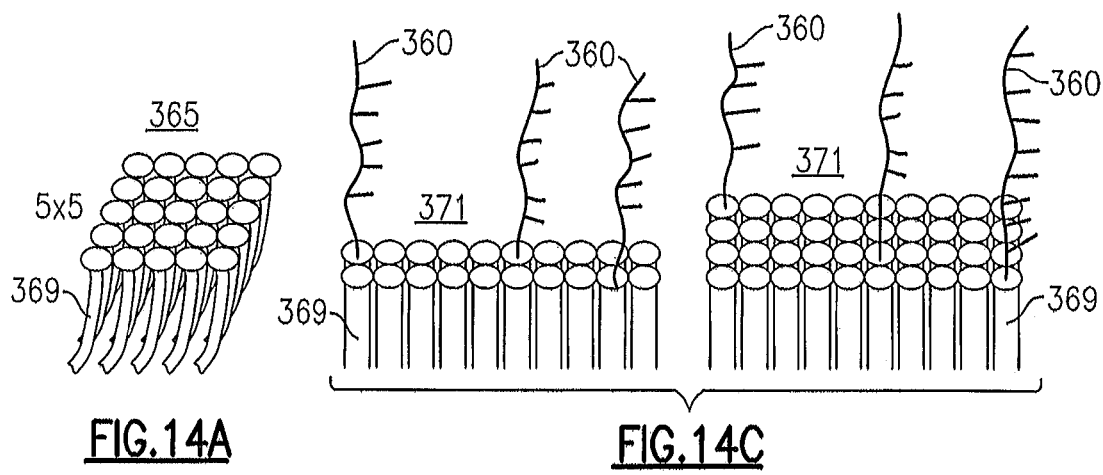
FIG.14A
FIG.14C
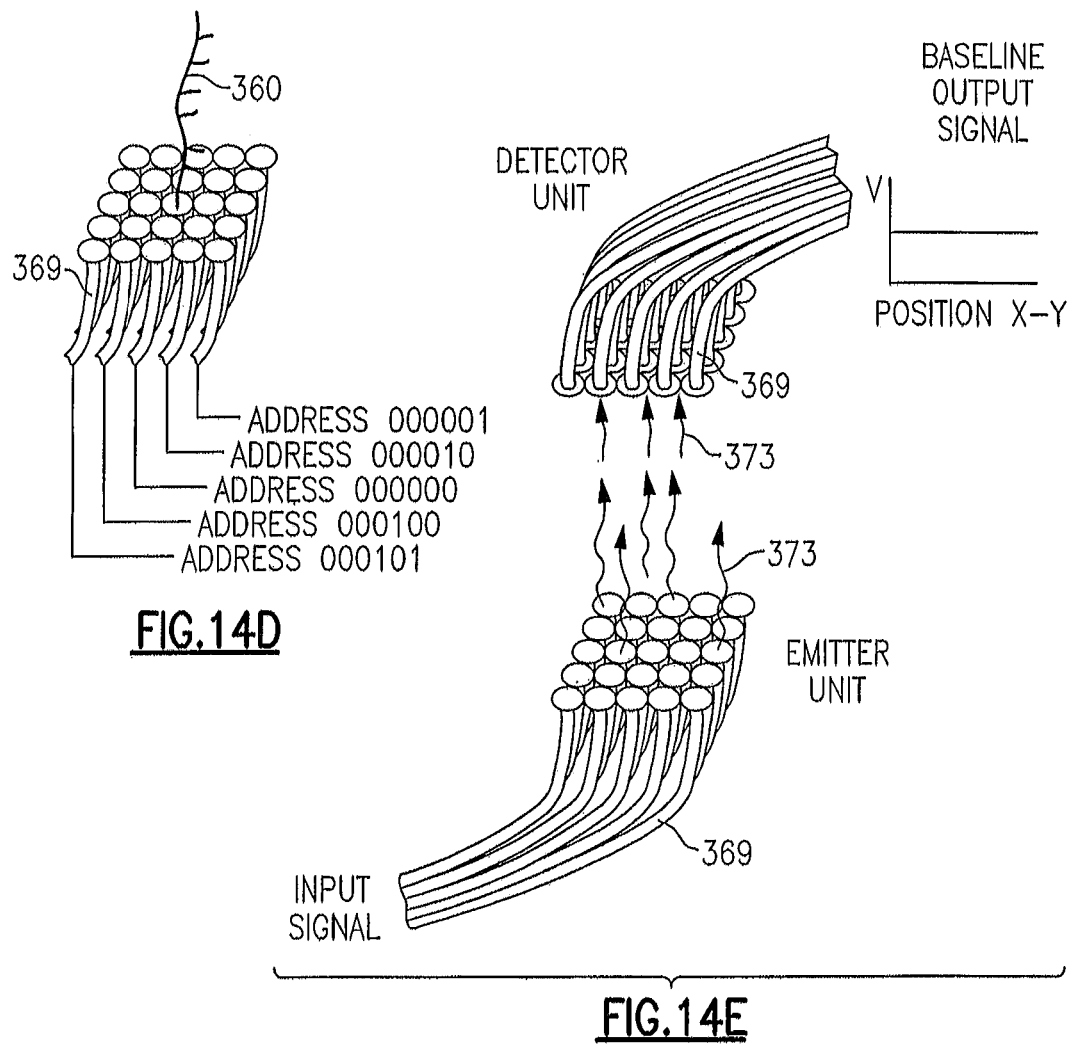
FIG.14D
FIG.14E

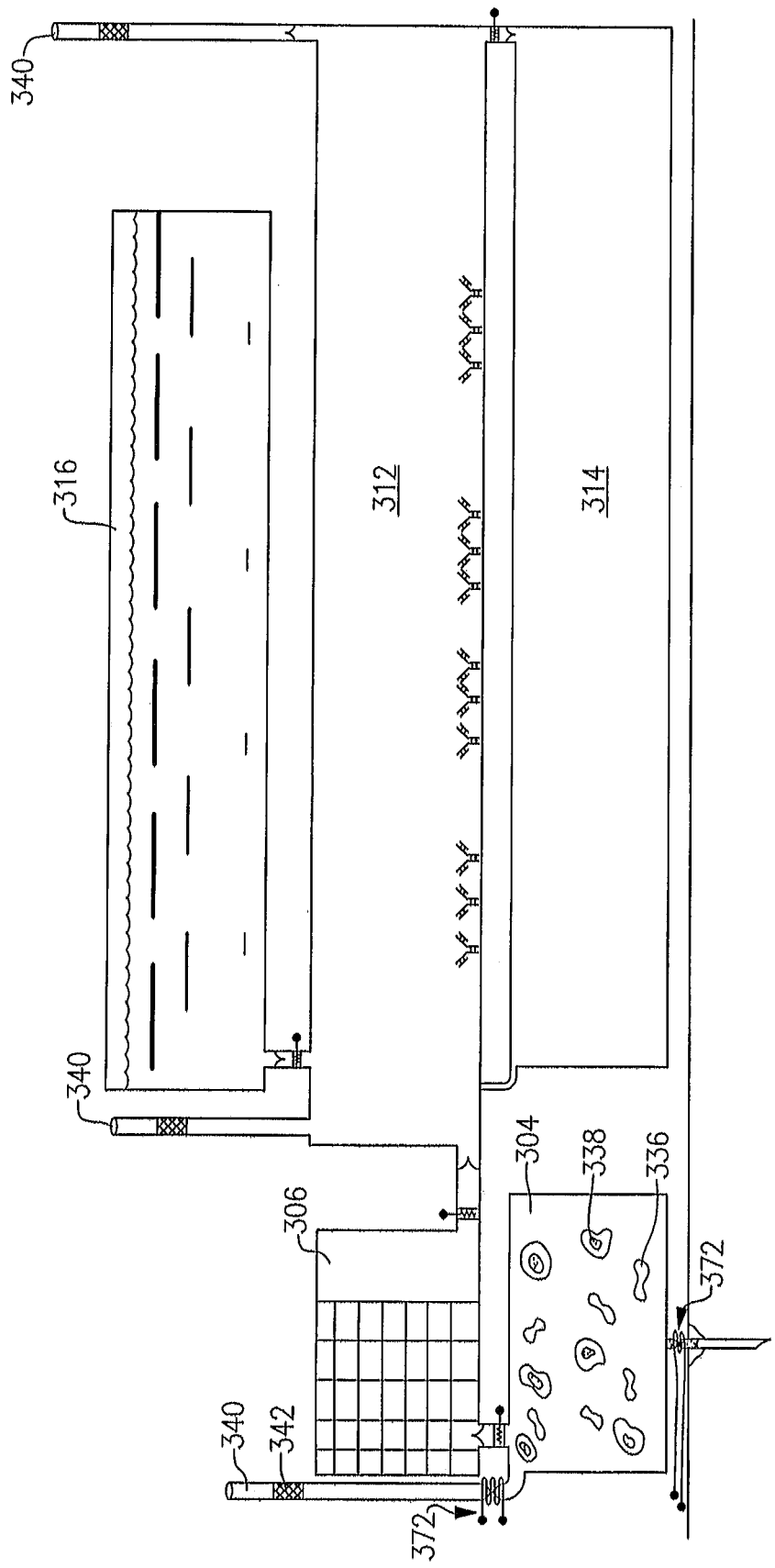

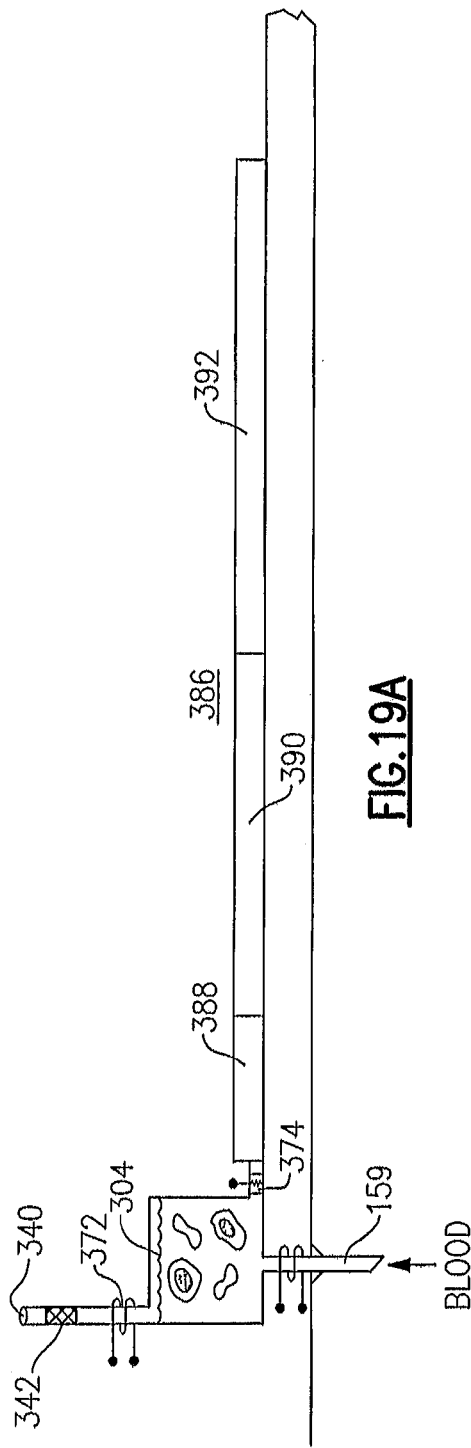
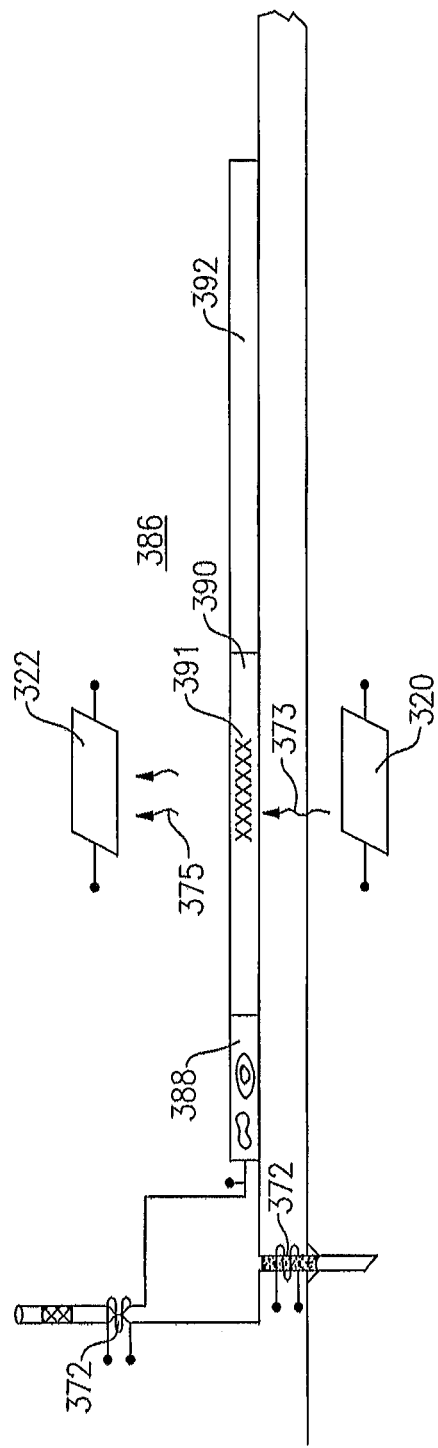

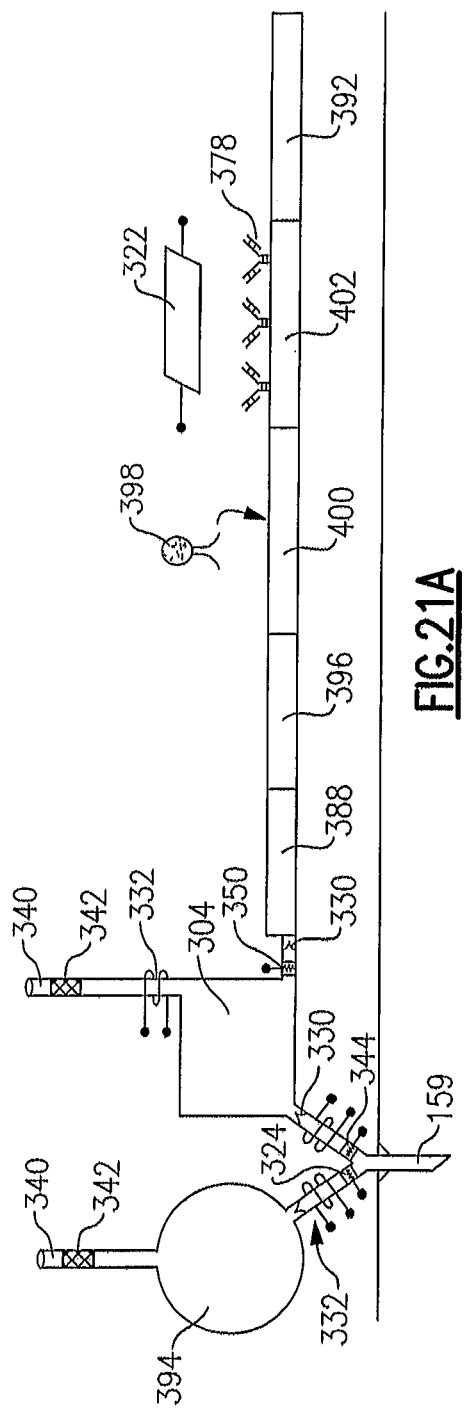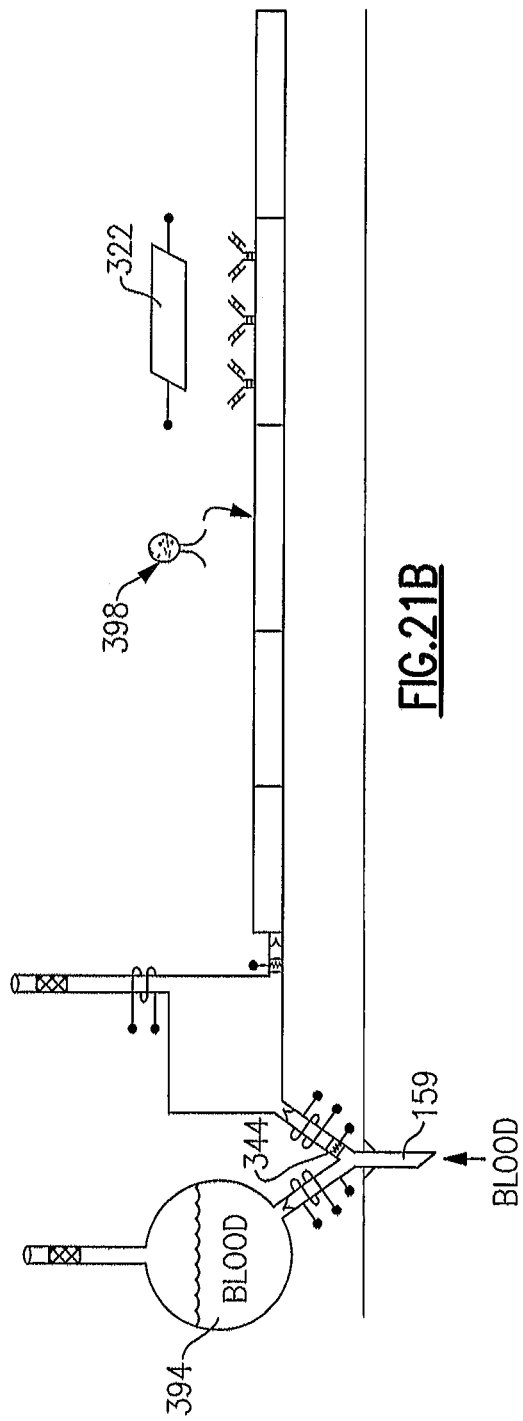

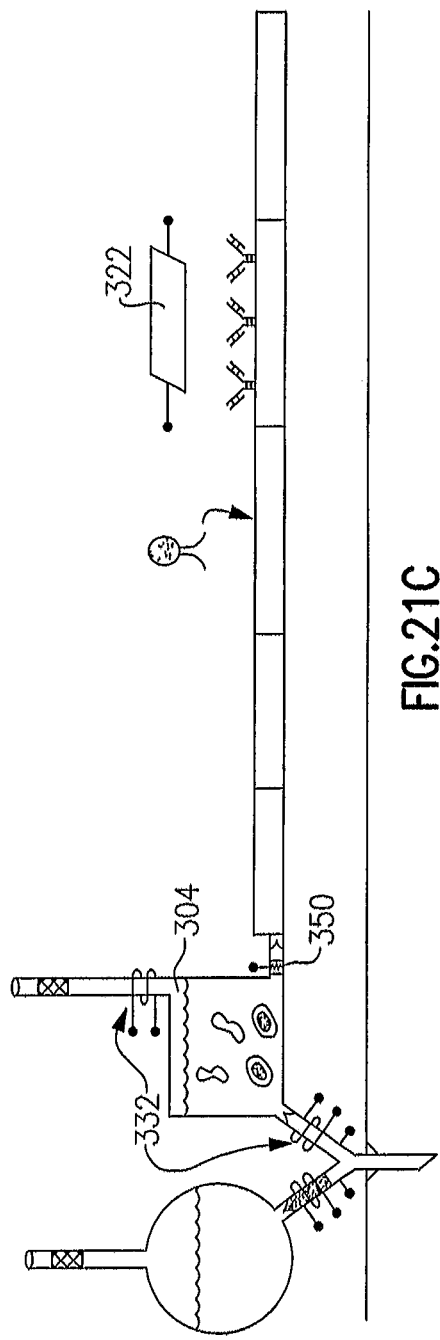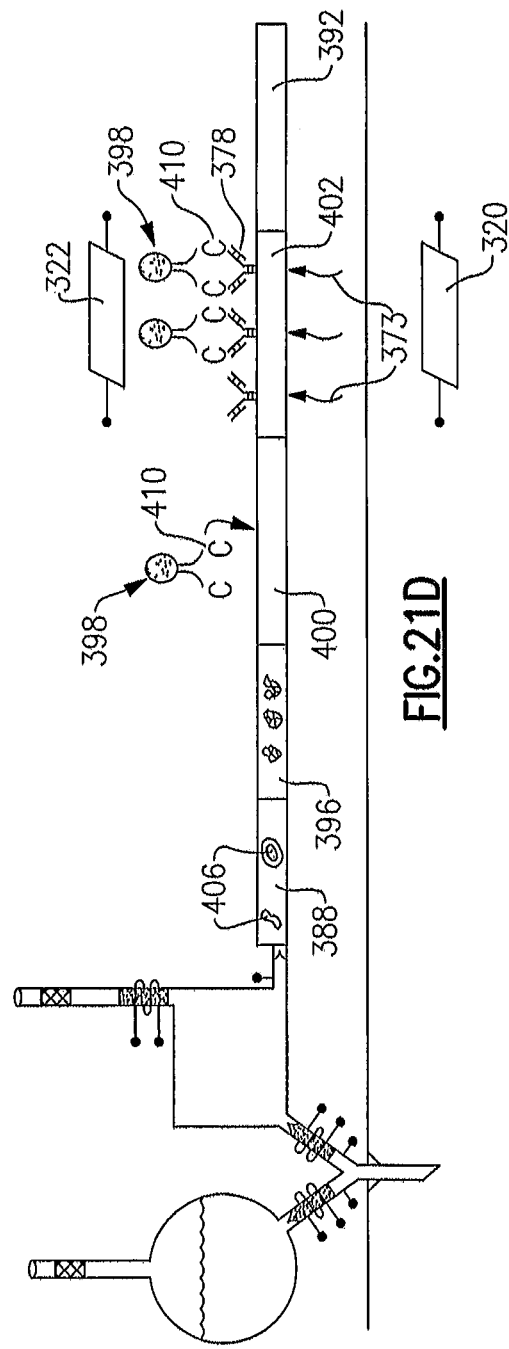

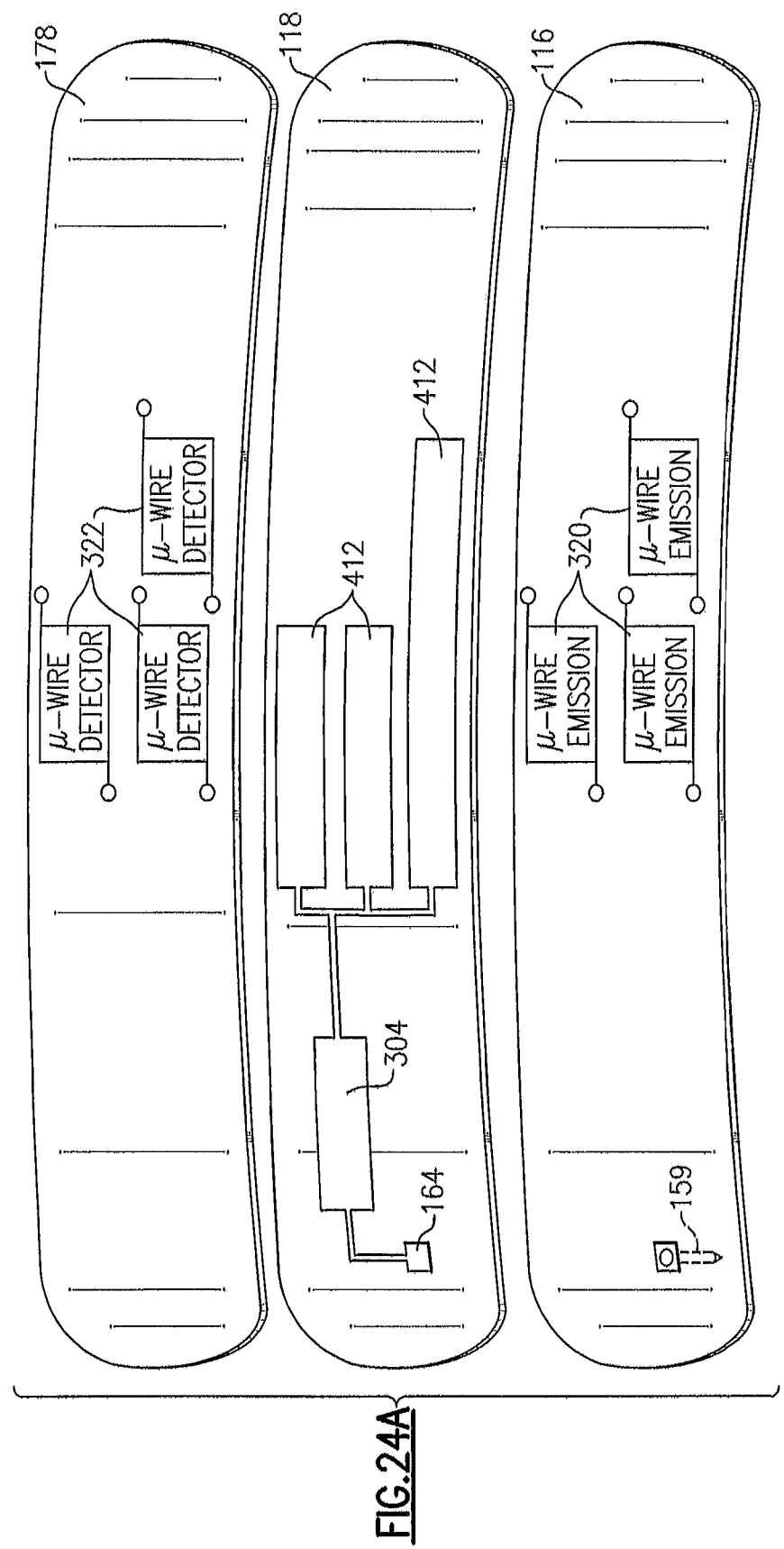

PERSONAL DIAGNOSTIC DEVICE HAVING A PLURALITY OF TUBULES

RELATED APPLICATIONS

Any and all applications for which a foreign or domestic priority claim is identified in the Application Data Sheet, or any correction thereto, are hereby incorporated by reference into this application under 37 CFR 1.57. This application is a continuation application of U.S. application Ser. No. 14/853,523, filed Sep. 14, 2015, now U.S. Pat. No. 9,993,189, issued on Jun. 12, 2018, which claims the benefit of U.S. patent application Ser. No. 10/934,665, filed Sep. 2, 2004, now U.S. Pat. No. 9,133,024, issued on Sep. 15, 2015, which claims the benefit of U.S. Provisional Application No. 60/510,769, filed on Oct. 11, 2003, and U.S. Provisional Application No. 60/500,102, filed on Sep. 3, 2003, each of which is incorporated herein by reference in its entirety.

STATEMENT REGARDING COPYRIGHTED MATERIAL

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all U.S. and foreign rights whatsoever relating to the copyright material contained herein.

BACKGROUND OF THE INVENTION

Field of the Invention

This invention relates in general to personal diagnostic devices such as dermal patches or diagnostic bracelets and, in particular, to interactive adhesive dermal patches and medical diagnostic bracelets. More specifically, but without restriction to the particular embodiments hereinafter described in accordance with the best mode of practice, this invention relates to interactive adhesive dermal patches and personal diagnostic bracelets including a skin/patch interface, at least one analysis or processing layer, and a user output and/or input interface.

Description of the Related Art

Prior hereto, typical dermal patches have been employed essentially as passive drug release devices for use on the human body. Examples of such devices include the nicotine patch used for cigarette smoking cessation and the sea-sickness patch employed to administer predetermined amounts of Dramamine, for example, to relieve the effects of sea-sickness.

Medical monitoring devices for diagnostic purposes are numerous. Such well known devices include, for example, x-ray machines, ultra sound devices, computerized axial tomography scanners (CAT scanners) which produce a tomograph that constructs a 3-D model of an object by combining parallel planes, electrocardiograms (ECG/EKG) monitoring systems for the electrical recording of the heart and use in the investigation of heart disease, electroencephalogram (EEG) systems for brain mapping and neuro-feedback, and Positron Emission Tomography (PET) scanning for brain imaging and related analysis.

More particularly, the arts related hereto have been contributed to by several artisans including, for example, Sarussi et al., Conn et al., and S. Berlin. As an illustration of such contributions, there is the device disclosed in U.S. Patent Application Publication No. 2003/0229276 in the name of Sarussi et al. This publication discloses a device for monitoring blood constituent levels having a microprocessing unit. In one embodiment, the device contains an alarm which is activated when a particular blood constituent falls below a predetermined level. In other embodiments, the device may include a display unit for displaying output signals or indicating the well being of the wearer. The Sarussi device may be contained within a housing which adheres to the surface of the skin. The device may also contain a light source such as a light emitting diode (LED).

U.S. Patent Application Publication No. 2002/0004640 (Conn et al.) discloses a device for measuring the concentration of target chemical analytes present in a biological system which involves application of a sensor device to the skin. In one embodiment, the analyte is extracted by means of iontrophoresis. The analyte is detected by including analyte-specific enzymes in the collection reservoir which react to produce a detectable product. The invention also involves use of a microprocessor.

In the disclosure of U.S. Pat. No. 6,585,646 issued to Stuart Berlin there is presented and discussed a skin patch for use in collecting and detecting specific markers in apocrine sweat which may indicate the existence of various diseases. In one embodiment, the Berlin patch contains monoclonal antibodies or other chemical compounds which produce a visible signal upon reaction with specific markers. In another embodiment, an electronic sensor is utilized.

U.S. Pat. No. 6,251,083 (Yum et al.) discloses a disposable patch for use in body fluid analysis. The patch includes a skin interface layer having an attachment means for attaching to the skin, a plurality of test zones, and an indicating reagent system for detecting the presence or concentration of an analyte by means of a spectrophotometric change. The reagents employed therein may include indicating dyes.

With reference next to U.S. Pat. No. 5,443,080 (D'Angelo et al.), there is disclosed a device having a skin interface membrane layer, a chemical reactant layer, an indicator means which displays a color response, and an electro-optical interpretation means.

U.S. Pat. No. 4,821,733 as issued to Peck discloses a transdermal detection systems for detecting a target substance which migrates to the surface of the skin. An adhesive means is used to attach the system to the skin surface. A detectable signal is produced which may be in the form of a visible color change. In one embodiment, the system is used to detect ethanol on the surface of the skin.

In U.S. Patent Application Publication No. 2002/0091312 in the name of Berner et al., there is disclosed a device and method for measuring the concentration of an analyte in a biological system wherein the device is in operative contact with a skin or mucosal surface. The analyte is extracted transdermally using an iontophoretic sampling means. A sensing means is used to obtain a detectable analyte-specific signal and a microprocessor is used to provide for one or more measurement cycles.

U.S. Pat. No. 4,732,153 issued to Phillips discloses a dosimeter which is attached to the skin for the collection of substances from the surface of the skin. The device produces an observable color change upon reaction of the collected substances with stored chemical compounds in the patch. The assay may be performed in situ in the transdermal dosimeter.

And as a further examples of contributions to the arts related hereto, there is disclosedzzz in U.S. Patent Application Publication No. 2002/0099308 (Bojan et al.) a multiple-layer device for collecting and detecting an analyte in interstitial fluid. This device includes a skin contacting layer and a detecting layer for detecting or measuring an analyte. A light source is utilized to transdermally extract the interstitial fluid. In U.S. Pat. No. 6,479,015 awarded to Long et al., there is disclosed a skin patch having an indicator layer which turns color in the presence of a lactate solution, while EP 1262559 (Deigner et al.) also discloses a dermal patch having an adhering means and a reagent layer.

Notwithstanding the advances in the arts related to the present invention, there has not been proposed a personal diagnostic device in the nature of an interactive dermal patch or bracelet including a skin/patch interface, at least one analysis or processing layer, an integrated micro-processor or computer, and a user output and/or input interface that incorporates the advantages of MEMS, bio-MEMS, or nano-based technologies to provide a wide variety of real-time patient diagnostic information or results directly to the patient user or patient caretaker without necessarily requiring involvement or intervention from medical professionals.

Thus with the advent of MEMS and Bio-MEMS in conjunction with related micro-systems and nano-systems, there is a need for an integrated interactive personal diagnostic device in the nature of a patch or bracelet that may be easily employed by a user to perform a wide variety of real-time clinical diagnostic tests that otherwise require complicated lab-based medical equipment or a visit to the doctor's office and the subsequent delay associated with the processing of blood or urine samples by established laboratories.

As a significant advancement over the prior art and related apparatus or methods, the present invention provides various embodiments of such personal diagnostic devices as embodied in an interactive patch or "bio-patch" that includes a skin/patch interface, at least one analysis or processing layer, and a user output interface integrated with MEMS, Bio-MEMS, and/or related micro-systems or nano-systems to perform a wide variety of desired tests in real-time while dermatologically employed by a patient or user. The bio-patch is implemented in a number of integrated flexible layers to form a light weight adhesively applied interactive dermal patch. The present invention and its various embodiments may also be implemented in a hard or semi-hard case or housing bracelet-type device which is conveniently referred to herein as a "bio-bracelet". Furthermore, the present invention is not limited to use on humans. Certain embodiments hereof are directed to use on animals relative to particular and certain needs of the livestock, breading, or dairy industries for example.

SUMMARY OF THE INVENTION

The present invention is directed to an interactive diagnostic patch or bracelet having a skin interface layer, one or more analysis or processing layers, and a user output interface. According to the invention, the patch or bracelet may perform a variety of in-situ diagnostic tests utilizing Micro Electrical Machine Systems (MEMS) or related micro- and nano-technologies. In one or more embodiments, the patch contains an adhesive layer for attachment to the skin. It may also contain means for collecting a transdermal biological sample such as blood or sweat. The collected sample may undergo one or more real-time qualitative or quantitative analyses to detect or monitor physiological changes in the body. The processing layer of the patch may contain various chemical reagents for reacting with the biological sample in order to produce a detectable signal. Results may be detected by CCD detector, laser emitting diodes (LED), or nano-wires. The signal may be visible via the user output interface layer in the form of a bar code, color change, numeric output, or alphanumeric output which may be color or monochromatic presented on a LED/LCD display, or it may be transmitted to a remote computer. The patch may contain other features including micro-fluidics, audio capabilities, minimally invasive tubules, fiber optic cables, light emitting or detecting nano-wires, cryogenic liquids, and photo emitters.

In another embodiment, the patch or bracelet device may be utilized to detect airborne biological agents that collect on the top surface thereof.

More particularly there is provided a dermal adhesive and/or non-adhesive patch or diagnostic bracelet incorporating any or all of a multitude of features enabling testing, analysis, diagnosis, treatment, input interfaces and output interfaces. The dermal patch or bracelet includes any or all options involving fluidic, micro-fluidic, micro-fluidic valves, reagent testing chambers, sensing equipment, logic processing in fluidic circuits, logic processing in electrical circuits, and connections from processing circuits to input and or output interfaces. The logic processing, and/or the input interfaces, and/or the output interfaces may reside on a reusable application which attaches to the surface of the testing patch or bracelet.

The testing patch and/or the reusable processing/interface may be any of a multitude of shapes including but not limited to rectangular, circular, or any other shape. It may also be of many sizes including but not limited to small over all measurements on the order of 1 millimeter, as large as 30 centimeters in outside dimensions, or any desired combination of lengths, widths, and thicknesses within the range of about 1 millimeter to 30 centimeters.

The testing patch or bracelet is capable of performing qualitative and/or quantitative tests and providing a user output and/or user input and/or processing capabilities in order to generate a logical result of the test.

The interface abilities of optional input and optional output include user viewable quantitative and/or qualitative data presented by any of a number of means including but not limited to LED/LCD flexible or rigid display within or on the device and or the reusable surface. User selectable buttons include, but not limited to, buttons, sliders, pressure switches, and remote input devices such as wireless interfaces and/or connected (wired) interfaces.

The personal diagnostic device of the present invention and its various embodiments may include one or more qualitative or quantitative tests that may be a number of the same test to be performed at intervals determined by logic and/or human input. The testing device may alternatively include a number of different tests each providing a qualitative and or quantitative result.

The present personal diagnostic device may also include cavities which may be employed for pressure testing and/or for providing energy in the form of compressed gasses such as air or vacuum.

More specifically, the present invention is directed to a personal diagnostic device that includes a sample acquisition layer for obtaining a fluid sample from a user; a fluid sample layer for processing the fluid sample obtained from the user, the fluid sample layer being in fluid communication with the sample acquisition layer; means for detecting diagnostic results derived from the processing of the fluid sample; and means for displaying the diagnostic results. The device may include at least one cavity containing a pressurized gas, or at least one cavity containing a vacuum. The device may further include hydrophobic surfaces for retarding fluid flow or hydrophilic surfaces for promoting fluid flow. The device may be equipped with a sound emitter for providing the user with feedback. The device may also include a logic processing system and an Internet Protocol address within the logic processing.

According to another aspect of this invention there is provided a personal diagnostic device including an air sample acquisition member for obtaining an air sample from the ambient environment of a user; means for testing the air sample for at least one specific air born contaminant; a fluid sample acquisition layer for obtaining a fluid sample from a user; a fluid sample layer for processing the fluid sample obtained from the user, the fluid sample layer being in fluid communication with the sample acquisition layer; a detector implemented to detect diagnostic results derived from the processing of the fluid sample; and a display unit that displays the diagnostic result. This device may further include a logic processing system having TCP/IP, and may include separately or in combination therewith a receiver and a transmitter to provide telemetry information regarding location of the user. The device is advantageously provided with a processor for processing the diagnostic results detected by the detector wherein the processor generates output information regarding a medical state of the user. A memory for storing the output information may also be provided in the device or external to the device.

In accordance with another aspect of this invention, the is further provided a method of using a personal diagnostic device. This method may include the steps of applying a respective personal diagnostic device to a user; allowing the personal diagnostic device to obtain a biological sample from the user; processing the biological sample in the personal diagnostic device to obtain medical or health information regarding the user; transmitting the information to a receiving device; and displaying output results associated with the medical information. This may include the further step of storing the information in the personal diagnostic device before the transmitting step is performed. The receiving device may be in the personal diagnostic device or it may be a personal computer, or linked to a communications network.

Various aspects of the present invention, described in detail below in conjunction with the drawing figures, include methods of qualitative and quantitative analysis of biological and chemical test samples carried out in-part or fully within the personal diagnostic device of the present invention. These test samples may include, but are not limited to, whole blood, serum, plasma, saliva, urine, sputum, stool, sweat, tissue samples, tumor or biopsy samples, water and other samples that may contain a chemical or biochemical target of interest. These targets of interest may include for example, specific nucleic acid sequences, proteins, antibodies, toxic chemicals, pollutants, stress indicators, cardiovascular health indicators, tumor markers, cells, bacteria, viruses, biochemical weapons, and other targets of a biological or chemical nature.

It is, therefore, an object of the present invention to improve upon limitations in the prior art. These and other objects are attained in accordance with the present invention wherein there is provided several embodiments of an interactive bio-patch, bio-bracelet, and various methods and processes relating thereto.

BRIEF DESCRIPTION OF THE DRAWINGS

Further objects of the present invention together with additional features contributing thereto and advantages accruing therefrom will be apparent from the following description of preferred embodiments of the invention which are shown in the accompanying drawing figures with like reference numerals indicating like components throughout, wherein:

FIG. 4 is a perspective view of an alternate embodiment of the personal diagnostic devices shown in FIGS. 1-3 including the aspect of a sample collection inlet port on the top surface thereof;

FIG. 8B is a perspective view of the personal diagnostic device according to the present invention as implemented in a bio-patch configuration;

FIGS. 12A to 12G present a series of related cross-sectional side views showing the progression of a test sample through the fluidic processing circuit of the device illustrated in FIGS. 11A and 11B as implemented to perform a DNA assay;

FIGS. 14A to 14K are detailed schematic and diagrammatic isolation views of the semiconductor nano-wire and micro-wire assemblies employed in this invention as light emitters and detectors for illuminating, detecting, and imaging DNA, small molecule, and cellular assay results derived from use of the personal diagnostic devices disclosed herein;

FIGS. 16A to 16F present a series of related cross-sectional schematic side views showing the progression of a test sample through the fluidic processing circuit of the device of FIGS. 15A, 15B, and 15C as implemented to perform a cellular assay;

FIGS. 19A and 19B are two related cross-sectional side views showing the progression of a sample through the fluidic processing circuit of the device of FIGS. 18A and 18B as implemented to perform small molecule assays;

FIGS. 21A to 21D are a series of related cross-sectional side views illustrating the progression of a test sample through the fluidic processing circuit of the device shown in FIGS. 20A and 20B as implemented to perform stress analysis;

FIG. 24A is an exploded perspective view of a sample acquisition layer, fluid processing layer, and results detection layer as employed in another alternate specific embodiment of the personal diagnostic device hereof implemented to perform elderly care monitoring in older patients;

DETAILED DESCRIPTION OF THE PREFERRED EMBODIMENT

The following description is first directed to a discussion of the basic structural and functional components of the personal diagnostic device (PDD) according to the present invention as embodied in bio-patches and bio-bracelets. Next presented is a detailed description of DNA assays and related methods as implemented on the PDD bio-patches and bio-bracelets according to specific embodiments of this invention. Then a detailed discussion of PDD cellular assay implementations and methods is presented. Thereafter, small molecule assay PDD implementations and related methods are discussed in detail. Then stress monitoring implementations and various related methods are presented. Next discussed are certain sports performance monitoring implementations and related methods illustrating various real-time use aspects of the present invention. And lastly, a detailed discussion of elderly care monitoring PDD implementations, applications, and related methods is presented to illustrate in detail certain further aspects of the present invention.

Structural and Functional Components

Figure 1:
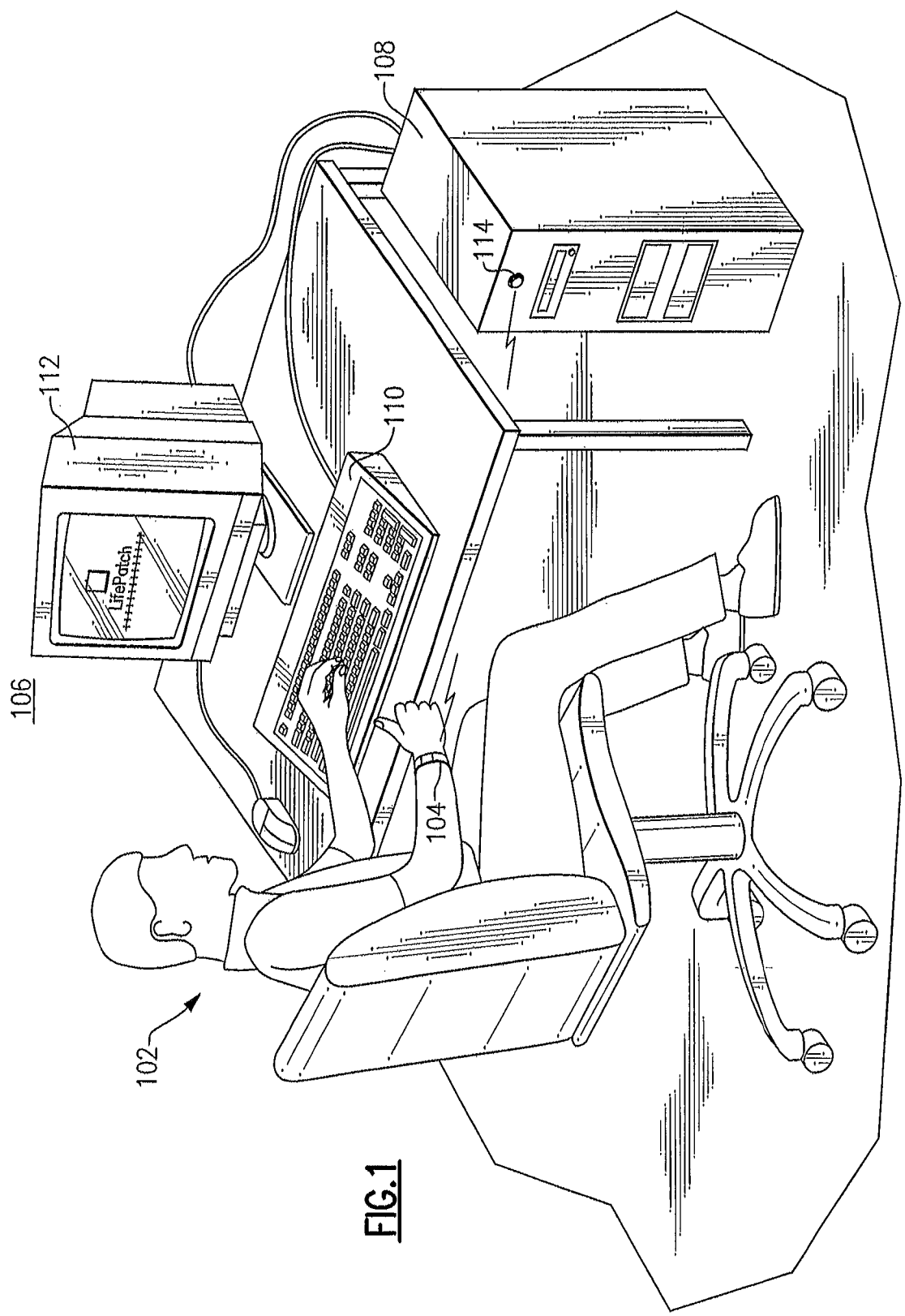
FIG. 1 is a perspective view of a user of the personal diagnostic device of the present invention sitting at a PC which is illustrated down-loading test results wirelessly from the device to the PC for the display of test results on the PC monitor.
Figure 8A:
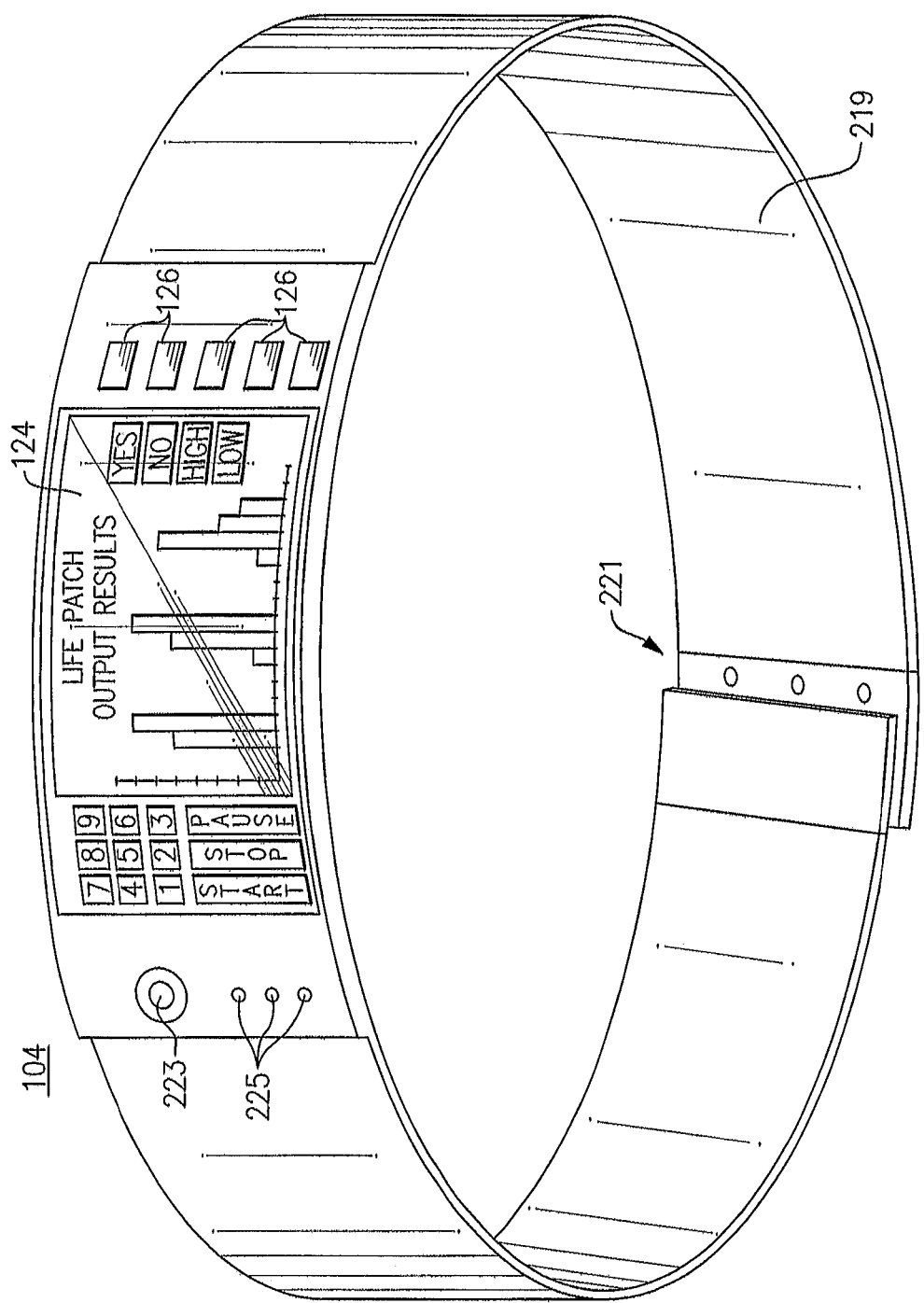
FIG. 8A is a perspective view of the personal diagnostic device of the present invention as implemented in a bio-bracelet configuration.

With reference now to FIG. 1 there is shown a user 102 wearing a personal diagnostic device 104 that may be implemented in either a bio-bracelet configuration (FIG. 8A) or a bio-patch configuration (FIG. 8B). The user 102 of FIG. 1 is seated at workstation 106 which includes a personal computer 108, a keyboard 110, and a display monitor 112. According to one principal embodiment of the personal diagnostic device 104, the device includes a radio frequency transmitter 223 (FIGS. 8A and 8B) which is employed to an transmit electronic signal from the personal diagnostic device 104 to the personal computer 108 which is outfitted with a suitable RF receiver 114. In this manner, diagnostic test results processed by and stored in the device 104 may be wirelessly transmitted to the personal computer 108 and then conveniently displayed on the display monitor 112.

Figure 2:
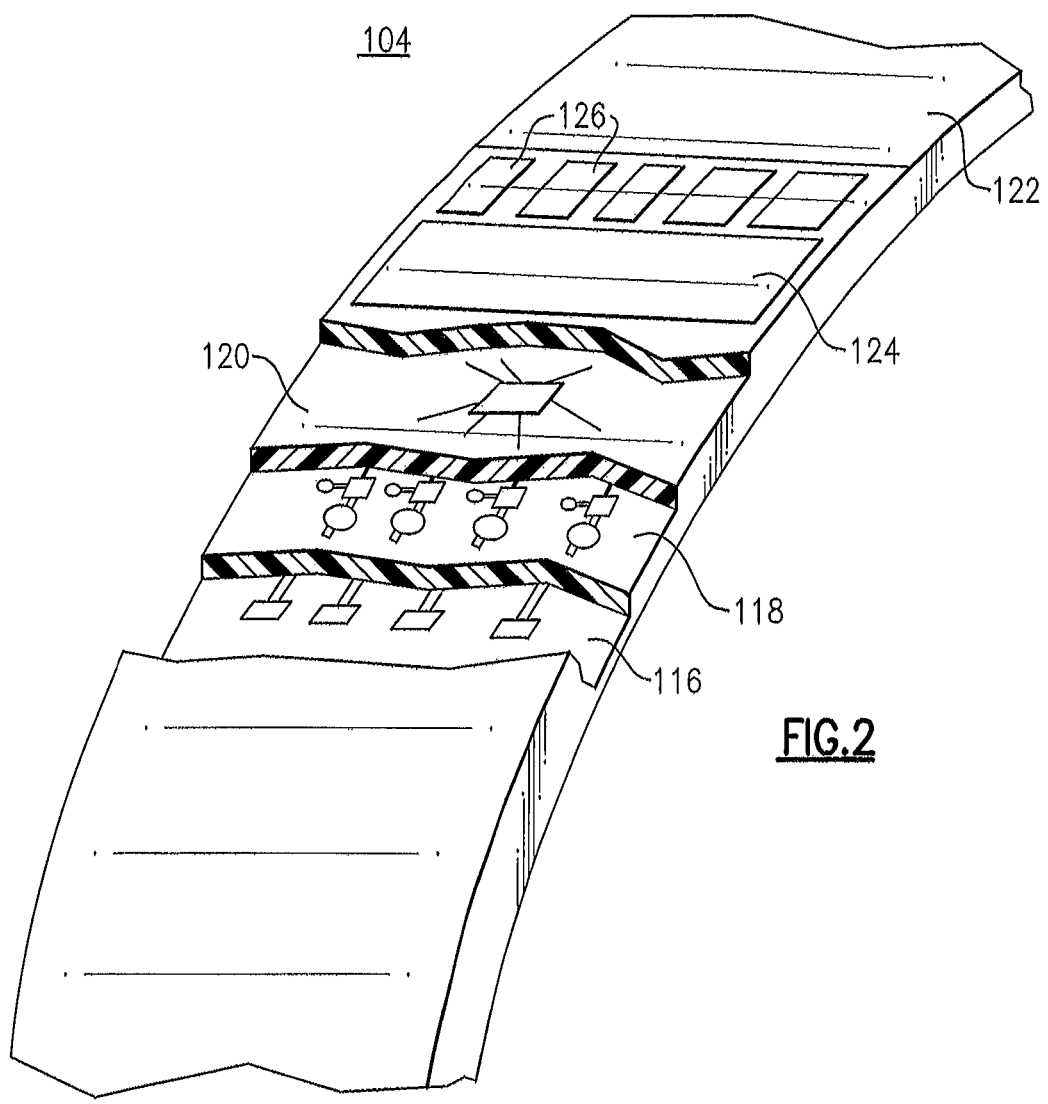
FIG. 2 is a perspective view of one embodiment of the analytical personal diagnostic device shown in FIG. 1 including cut away sections to reveal the components of each of the principal layers associated therewith.

Referring next to FIG. 2 there is shown a prospective view of one embodiment of the analytical personal diagnostic device 104 including cutaway sections to reveal the various components in each of the principal layers associated herewith. This embodiment of the device 104 includes a sample acquisition layer 116, a fluid processing layer 118, a results processing and control layer 120, and an output layer 122. The output layer 122 is illustrated with a video display monitor 124 and individual fixed-display results windows 126. The video display monitor 124 may display real time video information in the nature of a PC monitor or a television monitor. The fixed display result windows 126 are one time use result display windows that display in a fixed permanent manner the various results of a particular assay or assays performed in the device 104. The results displayed on the monitor 124 and the windows 126 may be qualitative, quantitative, or semi-quantitative.

Figure 3A:
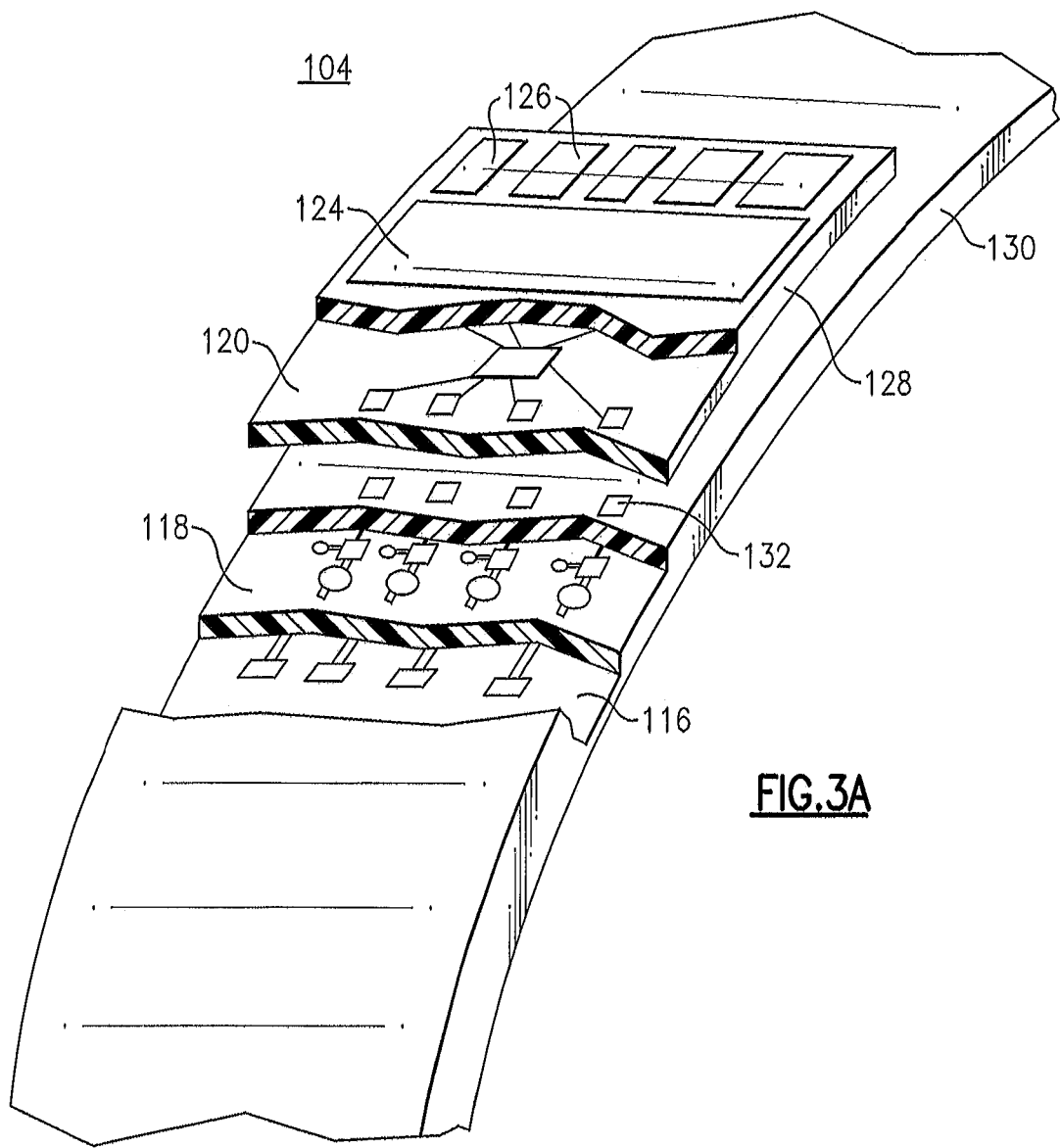
FIG. 3A is an exploded perspective view of an alternate embodiment of the analytical diagnostic device shown in FIG. 1 including removable and interchangeable portions illustrated with cut away sections to reveal the components of each of the principal layers and interchangeable portions.
Figure 3B:
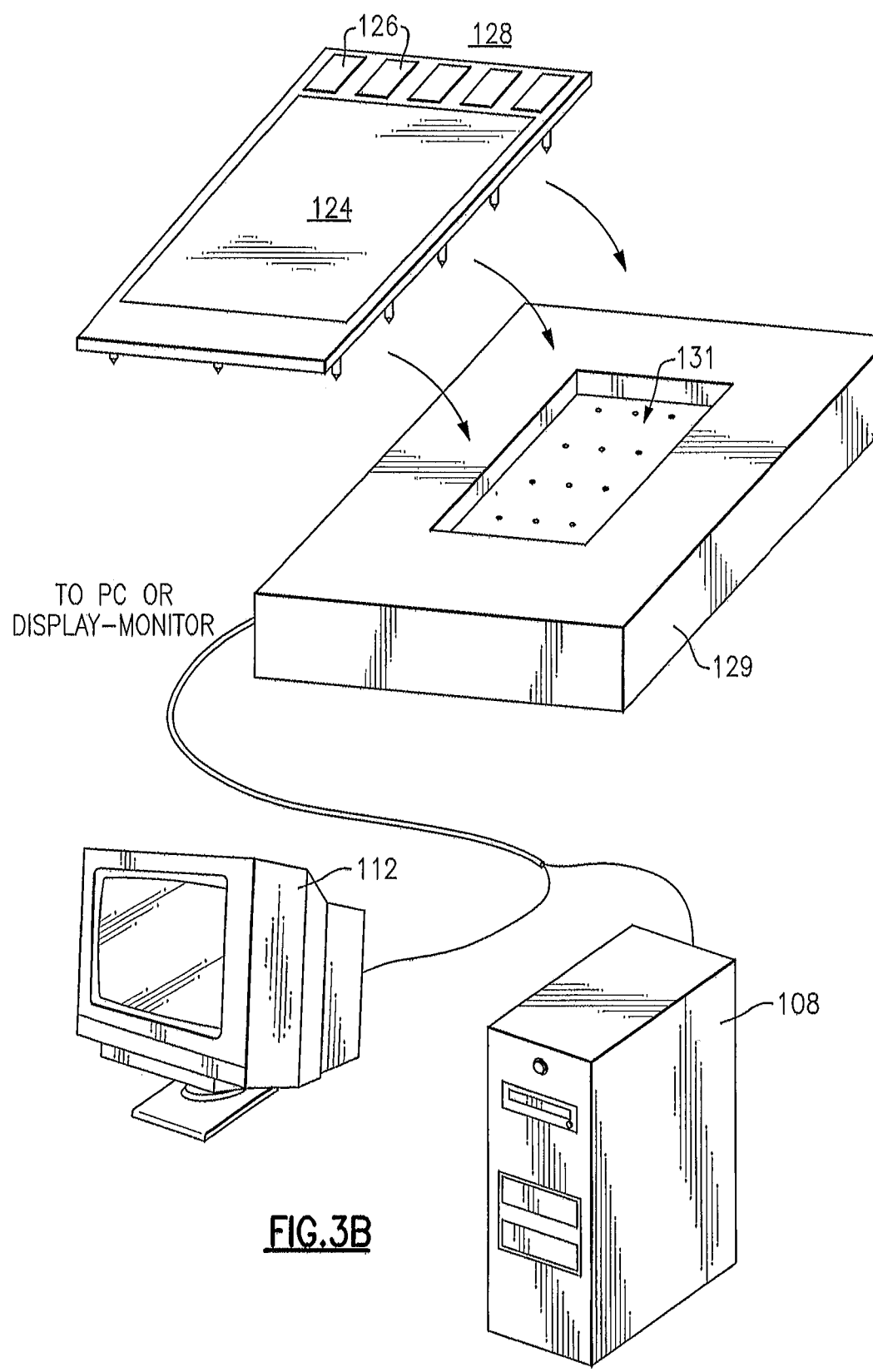
FIG. 3B is a perspective view of a reader device used in one embodiment to down-load results stored in the removal top portion of the device illustrated in FIG. 3A.

FIG. 3A is an exploded perspective view of an alternate embodiment of the analytical diagnostic device 104 including a removable and interchangeable top portion 128 as illustrated. FIG. 3A includes cutaway sections to reveal the components of each of the principal layers and interchangeable portions. More specifically, the device 104 shown in FIG. 3A includes the removable cap portion 128 which is provided with the processing and controlling layer 120, the video display monitor 124, and the fixed results display windows 126. The device 104 illustrated in FIG. 3A further includes a bracelet or base portion 130 which is provided with the sample acquisition layer 116 and the fluid processing layer 118. In the bio-bracelet embodiment hereof, the bracelet or base portion 130 may be made of a rigid material such as aluminum while in the bio-patch embodiment hereof, the bracelet or base portion 130 is made up of a flexible plastic layers. The base portion 130 further includes interface connectors 132 so that the removable cap portion 128 may be readily mounted and disconnected from the base portion 130. Thus in this implementation the present invention, a user may apply the base or bracelet portion 130 with a first removable cap portion 128 to receive and process results within a first time period. Thereafter, the user may then remove the first removable cap portion 128 and replace it with second removable cap portion 128 to continue to collect and process diagnostic information from the user's acquired biological samples. In an alternate embodiment, the individual removable cap portions 128 may be inserted into a receptacle 131 of a reader device 129 that down-loads the collected diagnostic information from the removable top portion 128 in a secured manner as illustrated in FIG. 3B. In this embodiment, the patient may not be allowed access to the collected information. The reader device 129, for example, would be in the custody of an attending doctor or caretaker in the doctor's office or hospital and the results then analyzed by the attending physician or medical professional rather than directly by the patient by interactive use of the PC 108 and monitor 112 as represented in FIG. 3B. Thus in various applications of this embodiment, the removable cap portion 128 may not include the device video display monitor 224 and/or the display windows 126. Alternatively, the device video display monitor 224 and/or the display windows 126 may be only partially operative so that certain test results are made available to the patient user while other test results are restricted to only doctor analysis via the down-loading aspect hereof.

With reference now to FIG. 4, there is shown a perspective view of alternate embodiment of the personal diagnostic device 104 of the present invention including air sample collection inlet ports or detectors on the top surface thereof. As illustrated in FIG. 4, the device 104 includes the sample collection layer 116, the fluid processing layer 118, the results processing and control layer 120, and the output layer 122 further alternatively including the video display monitor 124 and the fixed results displays 126. In addition thereto, the embodiment of the device 104 illustrated in FIG. 4 is further provided with a first air sample collection member, detector, or unit 134 and a second air sample collection member, detector, or unit 136. In this embodiment the air sample collection units 134 and 136 are intended to receive, capture, and detect various airborne particles that may be in the ambient environment in which a user is working or otherwise present. Such applications would include firemen fighting house fires, building fires, or forest fires; health care workers working in hospitals or research laboratories; employees and inspectors working in various chemical processing plants, oil refineries, or similar types of processing and power generating plants wherein exposure to airborne chemicals or other particular matter is a health and safety issue. In another implementation hereof, military personal and police officers may utilize such an airborne PDD system to detect potentially harmful biological, viral, or chemical particulate matter that has been accidentally or intentionally released into the environment. Thus the user of this embodiment of the personal diagnostic device 104 will be informed in the event there are any harmful levels of airborne particulate matter present in the surrounding environment. In addition thereto, the various sample acquisition, processing, and assaying aspects of the device 104 are then employed to monitor the user's biological and physiological responses to any such airborne particular matter that has been detected and identified by the first and/or second air sample collection units 134 and 136.

Figure 5:
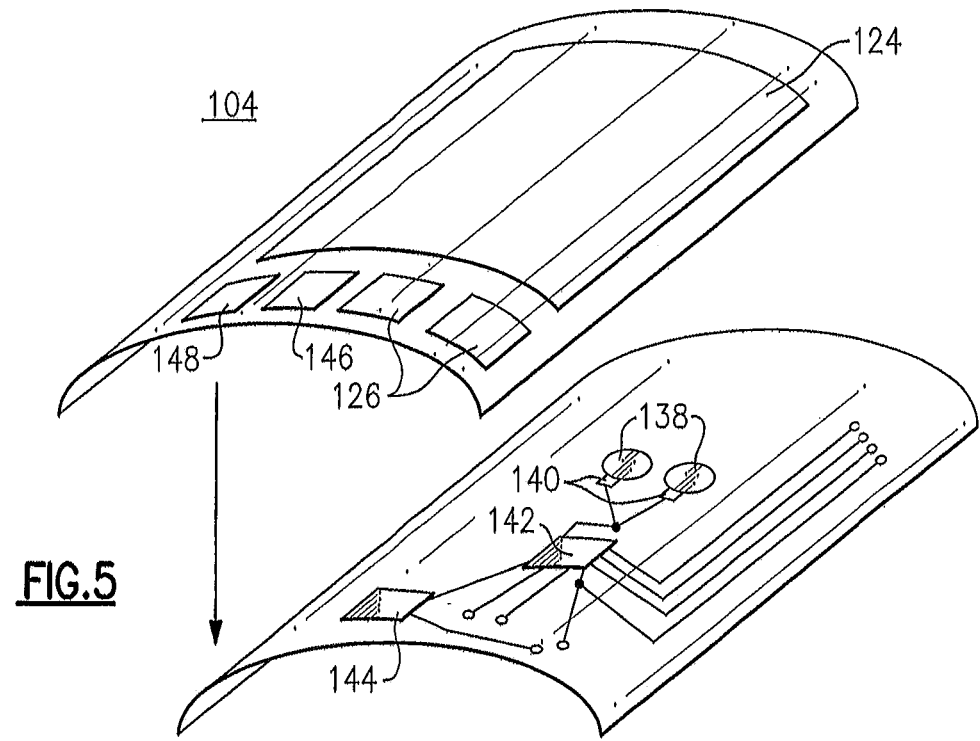
FIG. 5 is an exploded perspective view of another alternate embodiment of the personal diagnostic device shown in FIG. 1 including sound chambers and acoustic sensing microphones implemented for audio input/output applications.

FIG. 5 shows an exploded perspective view of yet another alternate embodiment of the personal diagnostic device 104 according to the present invention. The device 104 illustrated in FIG. 5 is provided with sound chambers 138, microphones 140, and a signal processing unit 142. The system elements including the sound chamber 138, microphones 140, and signal processing unit 142 are provided operating power by a small battery 144 preferably implemented in an integral manner in the bottom layer as illustrated. As an alternative to the battery 144 as the internal power source, the device 104 may be equipped with a solar cell type power source that converts incident light to electrical power for internal device use. As another alternative thereto, the device 104 may be provided with internal reactive chemicals that upon a controlled command react to thereby generate needed electrical power internally.

The top layer of the device 104 illustrated in FIG. 5 may include the video display monitor 124 and the fixed results display windows 126. In addition thereto, the top layer of the device 104 illustrated in FIG. 5 may further include an input selection switch 146 and an on/off swith 148. In this manner, the personal diagnostic device 104 illustrated in FIG. 5 includes both output capabilities as well as input capabilities. The one or combination of the principal elements of the device illustrated schematically in FIG. 5, may be combined with any other embodiments or subsystems of the various PDDs disclosed herein for specific application implementations.

Figure 6:
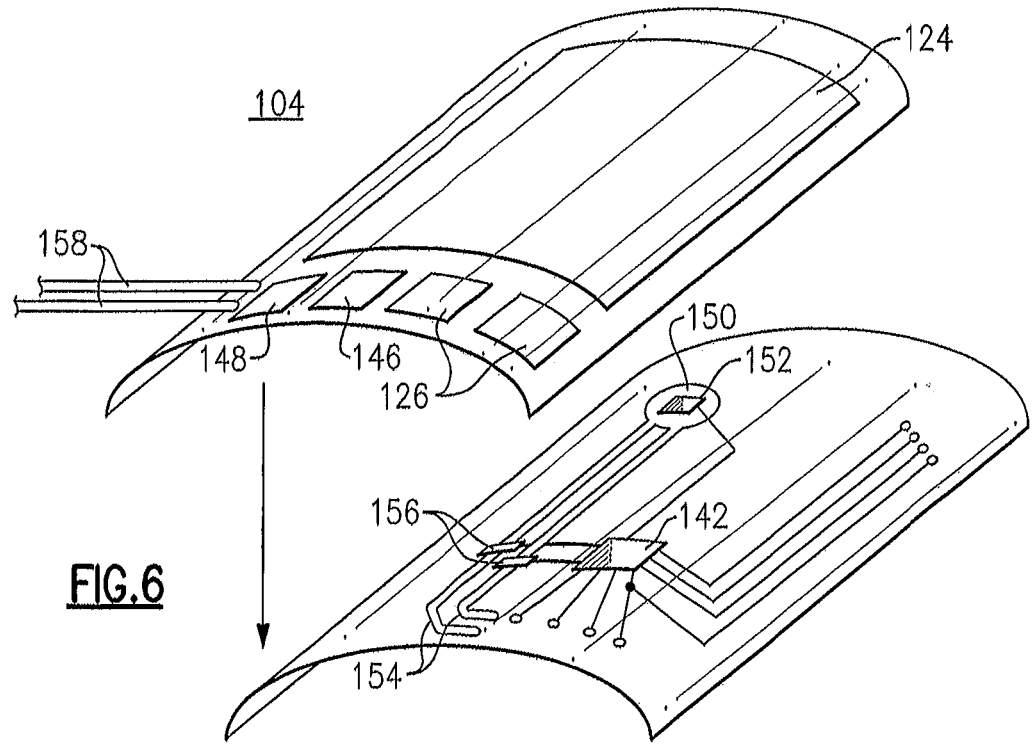
FIG. 6 is an exploded perspective view of yet a further alternative embodiment of the personal diagnostic device shown in FIG. 1 including a cryogenic tumor treatment assembly with a CCD for imaging the progress of treatment.

FIG. 6 schematically illustrates an example of an implementation of the PDD 104 for use in the treatment of skin lesions. More particularly, FIG. 6 is a perspective view a personal diagnostic device 104 including a cryogenic tumor treatment assembly with imaging capability to visually monitor progress of the treatment. The device 104 illustrated in FIG. 6 similarly includes the video display monitor 124, the fixed results display windows 126, the input selection member 146, and the on/off switch 148. The device of FIG. 6 is then further provided with a cryogenic chamber 150, a charge couple device (CCD) 152 for imaging, and cryogenic micro-fluidic channels 154. The flow of a cryogenic fluid such as liquid nitrogen is controlled in the channels 154 by employment of a series of valves 156 which may be electronically controlled by the signal processing unit 142 to direct flow in a pre-determined and timed manner. Cryogenic fluid such as liquid nitrogen may be supplied to the device 104 by means of input supply lines 158. It is contemplated that use of this implementation of the present invention would be in a doctor's office or other professionally supervised setting. The device is applied to an appropriately diagnose location on the skin lesion, cryogenic fluid such as liquid nitrogen is applied, and various steps in the lesion treatment are monitored in real time and displayed on the video monitor 124 as treatment progresses. In this implementation, the fixed display windows 126 may be utilized to take various diagnostic readings at desired intervals throughout the entire time duration of the skin lesion treatment process.

Figure 7A:
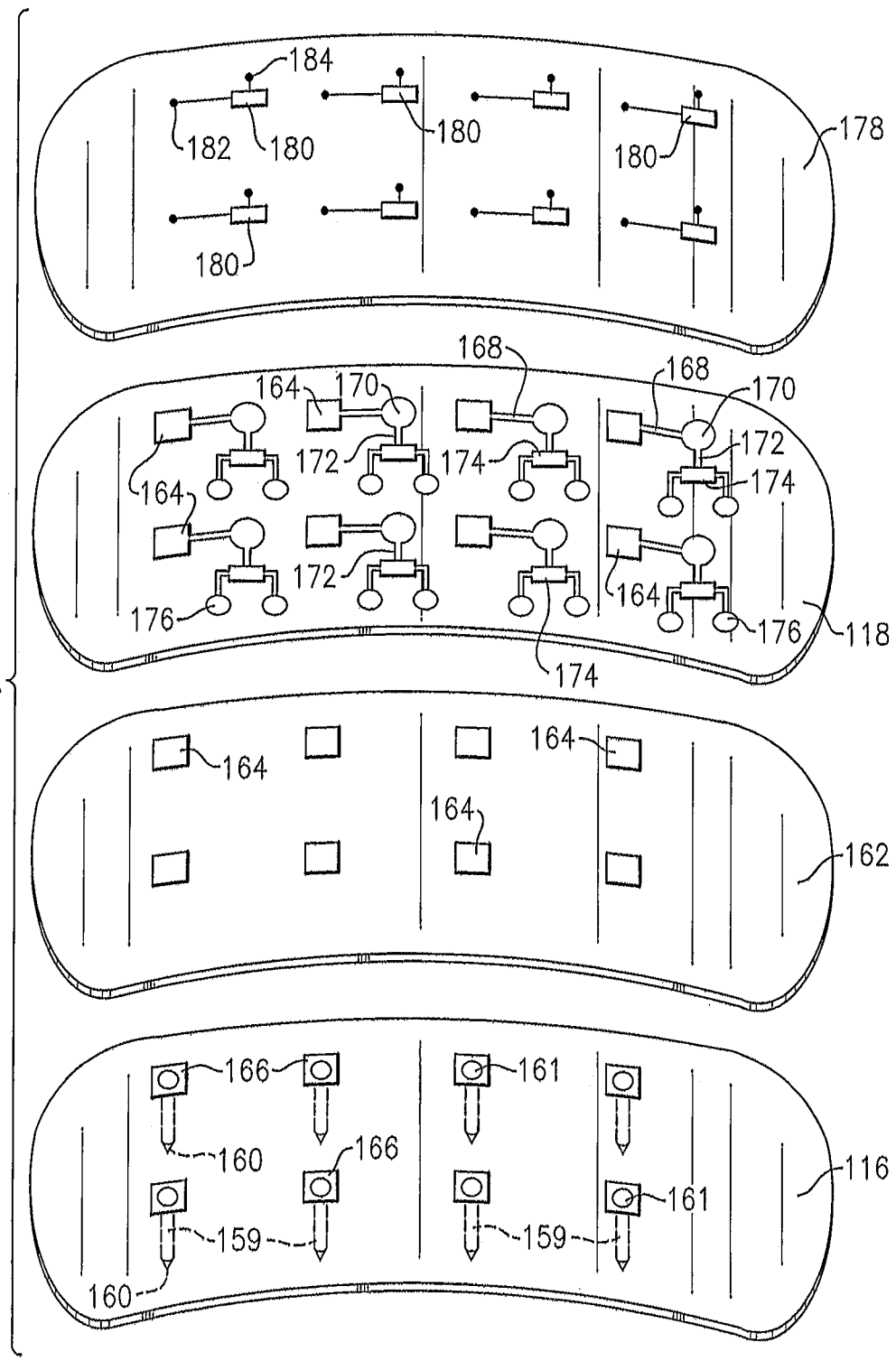
FIG. 7A is an exploded perspective view of the principal sample acquisition, fluid processing, and assay results detection layers of the personal diagnostic device according to the present invention.

With reference now to FIG. 7A, there is shown an exploded perspective view four of the principal layers of one preferred embodiment of the personal diagnostic device 104 according to the present invention. More specifically, FIG. 7A shows the sample acquisition layer 116 which is provided with minimally invasive tubules, lancets, or micro-probes 159 that penetrate the skin surface to acquire blood samples from capillaries near the epidermis. Alternatively, the tubules, lancets, or micro-probes 159 may be non-invasive and then implemented to acquire sweat or perspiration form the skin surface of a user. In this specific embodiment illustrated in FIG. 7A, the lancets or micro-probes 159 are implemented to transdermally draw blood or interstitial cell fluid (ICF) from the user. The tubules, lancets, or micro-probes 159 include a piercing end 160 and a discharge end 161. The piercing end 160 is implemented to penetrate the epidermis of a user and draw blood by capillary action up through the micro-probe or lancet 159 and into the device as further described in detail below.

Next provided is a spacing layer 162 as shown in FIG. 7A. The spacing layer 162 may be formed from any suitable flexible plastic material such as polymethylmethacrylate (PMMA), polycarbonate, polytetrafluoroethylene (TEFLON™), polyvinylchloride (PVC), polydimethylsiloxane (PDMS), polysulfone, and the like. The spacing layer 162 may be of a thickness on the order of 25 microns to 500 microns depending on the sample acquisition volume requirements and other assay specific requirements. As illustrated in FIG. 7A, the spacing layer 162 is provided with reservoir openings 164. The reservoir openings 164 are cutouts in the layer 162 which are positioned to be in register with corresponding inlet formations 166 integrally formed in the sample acquisition layer 116. The inlet formations 166 may be achieved by recessed areas, hollows, or dimples formed in the top surface of the sample acquisition layer 116 around the lancet or micro-probe discharge end 161 but which do not penetrate through to the bottom surface thereof. Thus in this manner when the microprobes 159 penetrate the user's skin, blood begins to flow by capillary action and then fills the sample collection chamber 224 (FIGS. 9 and 10) formed by a respective reservoir opening 164 and its corresponding inlet formation 166. Thus the sample collection chamber may be formed to collect a metered amount of blood of a specific or desired volume. As further illustrated in FIG. 7A, the fluidic processing layer 118 similarly includes the reservoir openings 164 which are formed and positioned in register with the corresponding reservoir openings 164 formed in the spacing layer 162. In this manner the reservoir openings 164 in the spacing layer 162 combined with the corresponding reservoir opening 164 in the fluidic processing layer 118 in further combination with the inlet formations 166 to create the sample collection chamber 224 illustrated schematically in FIGS. 9 and 10.

The fluid processing layer 118 may be similarly formed from any suitable flexible plastic material such as polymethylmethacrylate (PMMA), polycarbonate, polytetra-fluoroethylene (TEFLON™), polyvinylchloride (PVC), polydimethylsiloxane (PDMS), polysulfone, and the like. The fluid processing layer 118 may also be on the order of anywhere between 25 microns and 500 microns depending on the assay application and related volumetric and flow requirements within the fluidic processing circuits formed therein. More specifically in the embodiment of the fluidic processing layer 118 illustrated in FIG. 7A, there is shown a first fluidic channel 168 which is in fluid communication with the sample collection chamber 224, FIGS. 9 and 10, formed by the reservoir openings 164 and the inlet formations 166 as described above. The first fluidic channel 168 is in fluid communication with a fluidic chamber 170. To continue flow through the fluidic circuit, the fluidic chamber 170 is in fluid communication with a second fluid channel 172 which in turn is in fluid communication with a reaction zone 174. The reaction zone 174 may be utilized in differing embodiments in a wide variety of assay applications described below in conjunction with FIGS. 11A to 25D including DNA, cellular, small molecule, or other similar types of assays which are performed in conjunction with blood samples, DNA samples, or sweat samples obtained from or through the skin surface of the user. The reaction zone 174 may be in fluid communication with at least one waste chamber or collection chamber 176 to promote fluid flow and/or to collect wash buffer after the capture agents, for example, have captured, bound, or otherwise identified targets in the reaction zone 174.

The last principal layer illustrated in FIG. 7A is an assay results detection layer 178 which includes results detectors 180 each having an input 182 and output 184. The detector 180 may be embodied in any number of suitable types of detection formats including by way of example and not limitation, CCD imaging devices, electrical sensing or detecting electrodes, optical fibers, silicon-based sensors and bio-sensors, and individual or bundles of semi-conductor nano-wires or semi-conductor micro-wires which are implemented herein in various combinations as illuminating sources, detector devices, and/or imaging devices as discussed in further detail herein below. The detectors 180 are each respectively positioned over a corresponding reaction zone 174 as illustrated. In this manner, after assay results are manifest in the reaction zone 174, the detector 180 may be activated to detect, identify, or otherwise determine the existence, presence, or absence of expected, unexpected, desired, undesired, anticipated, or unanticipated assay results. One implementation of the results detector 180 according to the teachings hereof, includes the use of individual or bundles of semi-conductor nano-wires or micro-wires of the type currently being developed by Nanosys Inc. of Palo Alto, Calif. Further details, aspects, and implementations of the types, uses, and functions of the various detection and illumination systems employed herein according to various embodiments of the present invention are discussed with further specificity herein below.

Returning now to the principal component layers illustrated in FIG. 7A, it should be understood that when the sample acquisition layer 116, spacing layer 162, the fluid processing layer 118, and the assay results detection layer 178 are assembled and the inlet formations 166 thereby positioned in register with the reservoir openings 164; the sample collection chamber 224 (FIGS. 9 and 10) is closed at the top by the bottom surface of the results detection layer covering and sealing around the reservoir openings 164 formed in the spacing layer 162 and the fluid processing layer 118. In one embodiment hereof, the surfaces of the various layers include an adhesive to thereby obtain adhesion and sealing of the layers to each other. In other embodiments, the layers may be assembled together in a fluid tight manner by employing suitable plastic melting or micro-welding techniques. Similarly, when the sample acquisition layer 116, spacing layer 162, the fluid processing layer 118, and the assay results detection layer 178 are assembled, the results detectors 180 are each thereby respectively positioned in register with a corresponding reaction zone 174.

Figure 9:
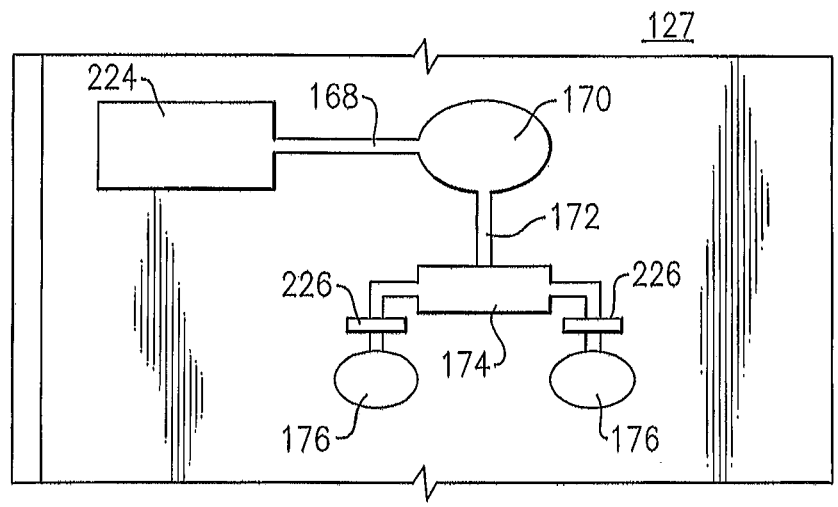
FIG. 9 is an enlarged detailed plan view of a single micro-fluidic circuit which may be employed in conjunction with various embodiments of the interactive analytical personal diagnostic device of the present invention.
Figure 10:
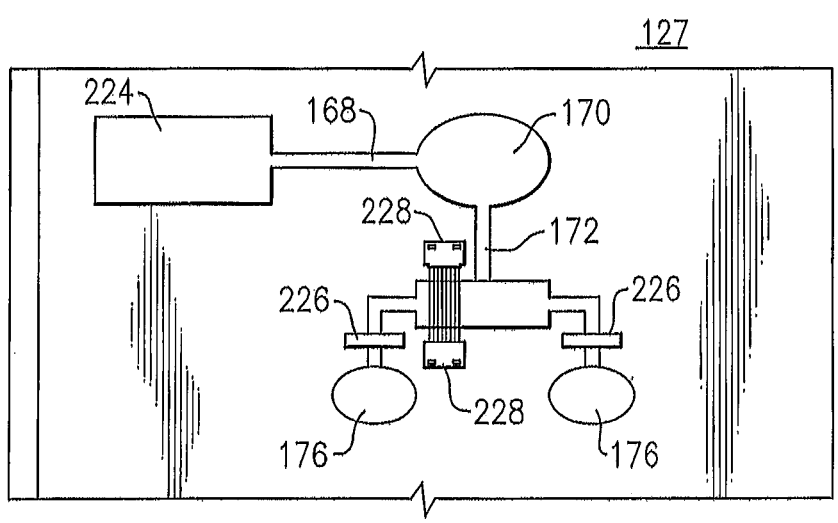
FIG. 10 is a view similar to FIG. 9 including an emitter and detector assembly implemented in conjunction with the illustrated micro-fluidic circuit.

The thickness of the fluid processing layer 118 relative to the thickness of the spacing layer 162 may be varied to achieve any desired volumetric relationship between the sample collection chamber 224, FIGS. 9 and 10, and the various components of the fluidic circuit represented in the fluid processing layer 118. For example, in a specific assay implementation it may be desired to have a relatively large sample volume collected in the chamber 224 while having the fluidic circuit of relatively smaller dimensions. In this case, for example, the spacing layer may be 500 microns thick while the fluid processing layer is, for example, 25 microns thick. Furthermore, the sample collection layer 116 may be, for example, 100 microns thick while the inlet formations formed therein may be, for example, 25 microns deep. Thus when the sample acquisition layer 116, spacing layer 162, the fluid processing layer 118, and the assay results detection layer 178 are assembled and the inlet formations 166 thereby positioned in register with the reservoir openings 164, the sample collection chamber 224 will have a height of 550 microns (500+25+25) while the fluidic circuit elements will have a height of 25 microns. Alternatively, for example, the fluid processing layer 118 may be 150 microns thick, the spacing layer 162 not utilized, the sample acquisition layer 116 also with a thickness of 150 microns with the inlet formations made 50 microns deep. In this case, the sample collection chamber 224 will have a height of 200 microns (150+50) while the fluidic circuit elements will have a height of 150 microns. In yet still alternate combinations hereof, both the spacing layer 162 and the inlet formations may not be utilized. In this case, the sample collection chamber 224 (FIGS. 9 and 10) will be formed only by the reservoir opening 164 in the fluid processing layer 118 and thus the fluidic circuit elements formed therein will have the same height as the sample collection chamber 224. Thus in view hereof, it should be understood that any desired combination of relative volumes and/or heights between and among the sample collection chamber 224, the first and second fluid channels 168 and 172, the fluid chamber 170, and the waste chambers 176 may be achieved by utilizing desired thicknesses of the spacing layer 162 and the fluid processing layer 118 with corresponding cutouts in the spacing layer 162 to add depth to any, all, or any combination for the fluid circuit elements in the fluid processing layer 118. Similarly, the inlet formations 166 as achieved by recessed areas, hollows, or dimples formed in the top surface of the sample acquisition layer 116 around the lancet or micro-probe discharge ends 161 may be utilized at any desired depth, or alternately not so employed to add volume to the sample collection chamber 224. Furthermore, additional volume may be selectively added to discrete circuit elements in the fluid processing layer 118 by utilizing recessed areas, hollows, or dimples formed in the bottom surface of the assay results detection layer 178.

Figure 7B:
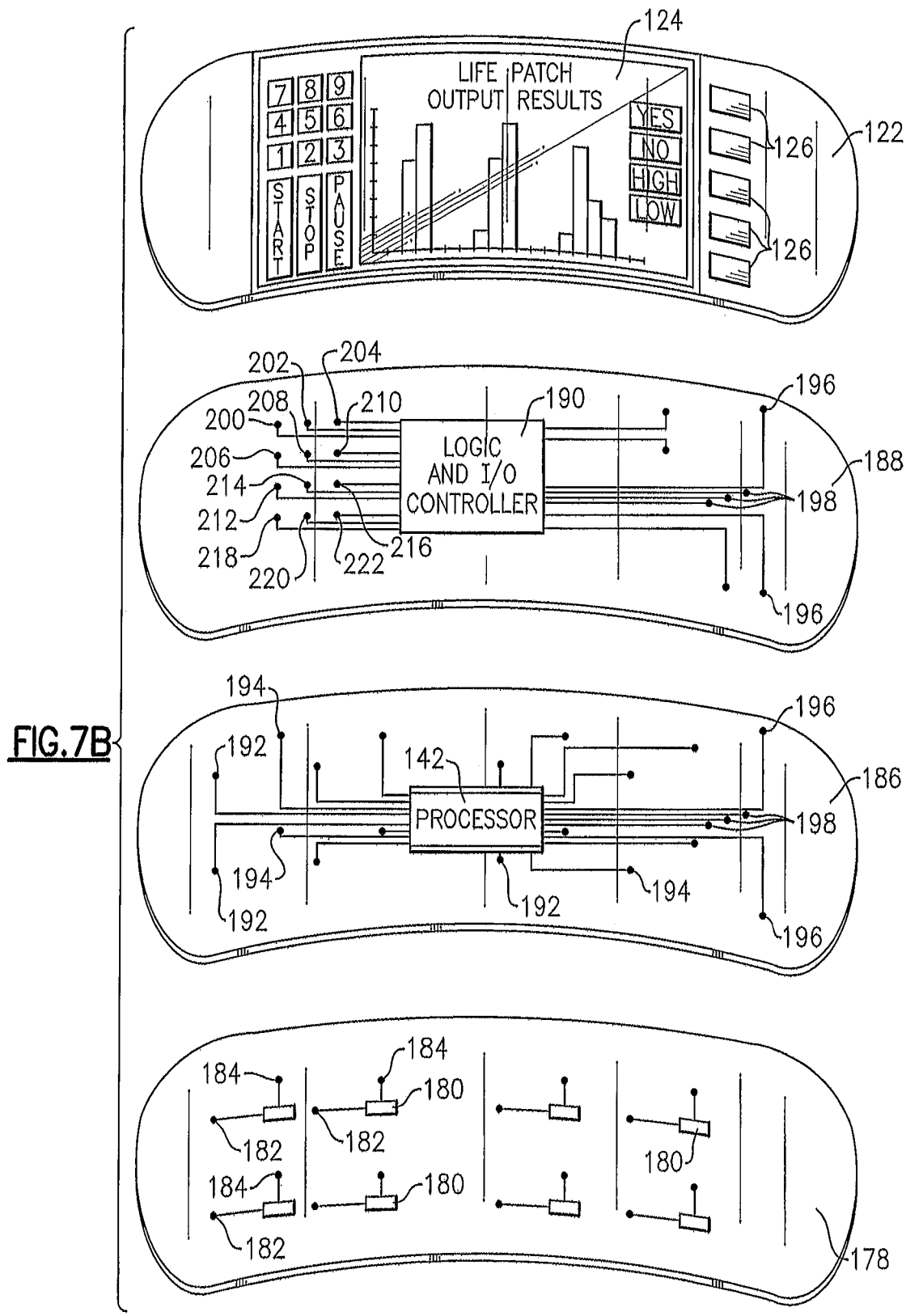
FIG. 7B is an exploded perspective view which illustrates the principal assay results detection layer, electronic processing layer, logic control layer, and input/output layer of the personal diagnostic device according to the present invention.

FIG. 7B is a view similar to FIG. 7A illustrating further principal layers of the personal diagnostic device 104 according to the present invention. More particularly, FIG. 7B shows again the assay results detection layer 178 of FIG. 7A, next a separate signal processing layer 186, a separate logic and input/output controller layer 188, and then the output layer 122 as described above in conjunction with FIGS. 2 and 4-6. The assay results detection layer 178 includes the results detectors 180 each with their respective input 182 and output 184. As illustrated, the signal processing layer 186 includes the processor 142 and the logic and input/output controller layer 188 includes a logic and I/O controller 190 hereinafter simply referred to for convenience as "controller 190". As shown, the processor 142 has a variety of electrical connection lines which each connect either to the inputs 182 and outputs 184 of the results detector 180 in the results detection layer 178 or to circuit connections associated with the controller 190. The processor 142 includes corresponding connections 192 and 194 as illustrated. More specifically as shown, each of the input connectors 182 and output connectors 184 of the results detector 180 are in register and connect respectively to a corresponding connection 192 or 194 associated with the processor 142. Similarly, the processor 142 includes output connectors 196 and input connectors 198 which upon assembly of the various layers illustrated in FIG. 7B correspond to and connect respectively with output connectors 198 and input connectors 196 associated with the controller 190 in the controller layer. In the embodiment of the device illustrated in FIG. 7B, the controller 190 further includes several input connectors which are referenced 200, 202, 204, 206, 208, 210, 212, 213, 216, 218, 220, and 222. As indicated in FIG. 7B, the input connector 202 of the controller 190 is situated for connection with the input key number "7" in the output layer 122. Similarly, the input connector 202 is positioned to make a connection with the number "8" key, the input connector 204 is situated to make a connection to the number "9" key, the input connector 206 is placed to make a connection with the number "4" key, the input connector 208 is positioned to make a connection to the number "5" key, the input connector 210 is located to make a connection with the number "6" key, the input connector 212 is situated to make a connection to the number "1" key, the input connector 214 is placed to make a connection with the number "3" key, the input connector 218 is situated to make a connection to the "start" key, the input connector 220 is positioned to make a connection with the "stop" key, and the input connector 222 is located to make a connection to the "pause" key. As further illustrated, other connections from the controller 190 are provide to facilitate desired communication between the input/output layer 122, the processor 142, and the controller 190. These connections and communication networks will be described in further detail below in connection with the discussion of specific assay implementations. Thus in this manner, the personal diagnostic device 104 is provided with both input capability as well as output capability for interactive use by a patient wearing the device as intended.

As represented in the input/output layer 122 of FIG. 7B, assay results may be displayed in either the video display monitor 124 or the fixed results windows 126. These results may be qualitative and in the form of a "Yes" or "No" result display, or a "Positive" or "Negative" result display; quantitative and in the form of calibrated bar graphs as shown; or semi-quantitative giving an indication such as "High" or "Low" depending on the particular assay implementation and desired results.

With reference now to FIG. 8A, there is illustrated a perspective view of the personal diagnostic device of the present invention as implemented in a bio-bracelet configuration. In this configuration, the is provided with the radio frequency transmitter 223 as discussed above. The device 104 as shown also includes connection indicator lights 225 which may be enabled to blink or otherwise emit light to indicate a proper wireless connection between the device 104 and the PC 108 via the RF receiver 114, FIG. 1. The bio-bracelet 104 of FIG. 8A is provided with a band 219 and a clasp 221 so that a user may wear the bans around the wrist or ankle, for example. The band 219 may be made of a flexible, stretch material to provide good holding force between the device and the user, or may be made of a hard material such as stainless steel or aluminum. FIG. 8B is a perspective view of the personal diagnostic device 104 according to the present invention as implemented in a bio-patch configuration. In this particular embodiment, the device 104 includes the video display monitor 124, the individual fixed-display results windows 126, a pair of RF transmitters, and the connection indicator lights 225. As with any of the embodiments of the device 104 discussed herein, the RF transmitters 223 may include both transmission capabilities as well as receiving capabilities to thereby establish two-way communication between the device 104 and the PC 108, and to further establish interactive two-way communication with any networks to which the PC 108 may be connected or otherwise linked.

Turning now to FIGS. 9 and 10, there is shown an enlarged detail schematic representation of a single microfluidic circuit 123 which may be employed in conjunction with the various elements and layers of the personal diagnostic patch 104 of the present invention. The micro-fluidic circuit 123 shown in FIGS. 9 and 10 includes the sample collection chamber 224 which may be formed by the reservoir openings 164 and inlet formations 166 as discussed above in conjunction with FIGS. 7A and 7B. As represented in FIGS. 9 and 10, the sample collection chamber 224 is in fluid communication with the first fluid channel 168 which in turn is fluidly connected to the fluidic chamber 170 which is in fluidic communication with the second fluid channel 172 which is next in fluid communication with the reaction zone 174. As discussed in further detail for the various assay implantations discussed below, a wide variety of assays may be conducted within the reaction zone 174. The reaction zone 174 may be in fluid communication with at least one waste or collection chamber 176. To promote flow control within the fluidic circuit 123 illustrated in FIGS. 9 and 10, the circuit may include micro-valves 226 which may be implemented in a wide variety of different configurations. Additional details regarding the valving and fluid control elements and methods utilized in the various embodiments hereof are presented and discussed herein below in connection with FIGS. 13A-13E and in further connection with specific assay implementations thereafter described.

FIG. 10 is a view similar to FIG. 9 further illustrating an optical emitter 228 and an optical detector 230. In order to detect and image manifest results of a number of different types of assays, the results detector 180 is implemented as the optical detector 230 which may be employed in combination with the optical emitter 228. The various optical and electrochemical phenomena that may be detected with the optical detector 228 or generally the results detector 180 are presented below in Table 1. Further detailed explanation relating thereto may be found in "Point of Care Testing", 2nd edition, edited by Christopher Price, Andrew St John, and Jocelyn Hicks, 2004.

TABLE 1

| Signal Generation | Types |
| --- | --- |
| Optical Detection | Absorbance, Reflectance, Transmission, Fluorescence, Luminescence, Turbidimetry and Nephelometry |
| Electrochemical Signals | Amperometric, Impedimetric, Potentiometric |
| Optical Motion | Light Scattering, Paramagnetic Particles, Interference Pattern, Image Analysis |
| Surface Interrogation | Optical Interference, Pattern Recognition, Surface Enhancement, Diffraction, Ellipsometry, Surface Plasmon Resonance |

The optical emitter 228 and optical detector 230 may be embodied in a variety of different optical devices or formats including for example, but not limited to, charged coupled devices (CCD), fiber optics, nano-wires, micro-wires, semiconductor light emitting and/or detecting materials, or other suitable light emitting and detecting materials or devices.

DNA Assay Implementations and Methods

The ability to detect target nucleic acid analytes of specific nucleic acid sequence using nucleic acid probe hybridization methods has many applications. Among these applications are diagnoses of infectious or genetic diseases or determination of susceptibility to cancer in humans or other animals; identification of viral or microbial contamination of cosmetics, food or water; and identification or characterization of, or discrimination among, individuals at the genetic level, for forensic or paternity testing in humans and breeding analysis and stock improvement in plants and animals. The basis for applications of nucleic acid probe hybridization methods is the ability of an oligonucleotide or nucleic-acid-fragment probe to hybridize, i.e., form a stable, double-stranded hybrid through complementary base-pairing, specifically with nucleic acid segments which have a particular sequence and occur only in particular species, strains, individual organisms or cells taken from an organism.

One of the basic limitations in nucleic acid probe hybridization assays has been the sensitivity of the assays, which depends on the ability of a probe to bind to a target molecule and on the magnitude of signal that is generated from each probe that binds to a target molecule and that can be detected in a time period available for detection. Known detection methods in the assays include methods dependent on signal generated from a probe, as from fluorescent moieties or radioactive isotopes included in the probe, or an enzyme, such as an alkaline phosphatase or a peroxidase, linked to the probe and, after probe hybridization and separation of hybridized from unhybridized probe, incubated with a specific substrate to produce a characteristic colored product. However, the practical detection limit of these assays is about 200,000 target molecules (3 femtomolar concentration in 100 µl), which is not sufficiently sensitive for many applications. Much effort is therefore being expended in increasing the sensitivity of detection systems for nucleic acid probe hybridization assays.

Achieving adequate limits of detection has been one of the difficulties facing the clinical application of nucleic hybridization methods. Several amplification methods have been developed to alleviate this difficulty by increasing either the sample or detection product. The Polymerase Chain Reaction (PCR) is the best known and most widely applied of these methods. With respect to PCR amplification, reference is made to Current Protocols in Molecular Biology, Suppl. 4, Section 5, Unit 3.17, which is incorporated herein by reference, for a basic description of PCR. Other references which describe PCR include Erlich, H. A., (Ed.) 1989, PCR Technology, Stockton Press; Erlich, H. A., et al. (1988), Nature 331:461-462; Mullis, K. B. and Faloona, F. A. (1987), Methods in Enzymology, 155:335-350; Saiki, R. K., et al. (1986), Nature 324:163-166; Saiki, R. K., et al. (1988), Science 239:487-491; Saiki, R. K., et al. (1985), Science 230:1350-1354; U.S. Pat. No. 4,683,195 to Mullis, et al.; and U.S. Pat. No. 4,683,202 to Mullis. All of which are incorporated by reference as if fully repeated herein.

First invented by Kary Mullis, PCR has been widely adopted and adapted for many research purposes, and commercial kits for clinical diagnosis are now available. However, these amplification methods are time-consuming, labor intensive, costly, and susceptible to contamination, resulting in false positives.

Therefore, the development of a quick, easy to use, inexpensive medical devices that allow for the detection of very low level of target nucleic acids without target amplification and probe labeling are of particular interest.

The nucleic acid analysis device implementation of the personal diagnostic device 104 is herein referred to as the DNA patch or bracelet which provides a quick, effortless, and automatic method for nucleic acid detection using only a simple patch or bracelet that interfaces with a personal computer or a data display unit as described above.

Figure 11A:
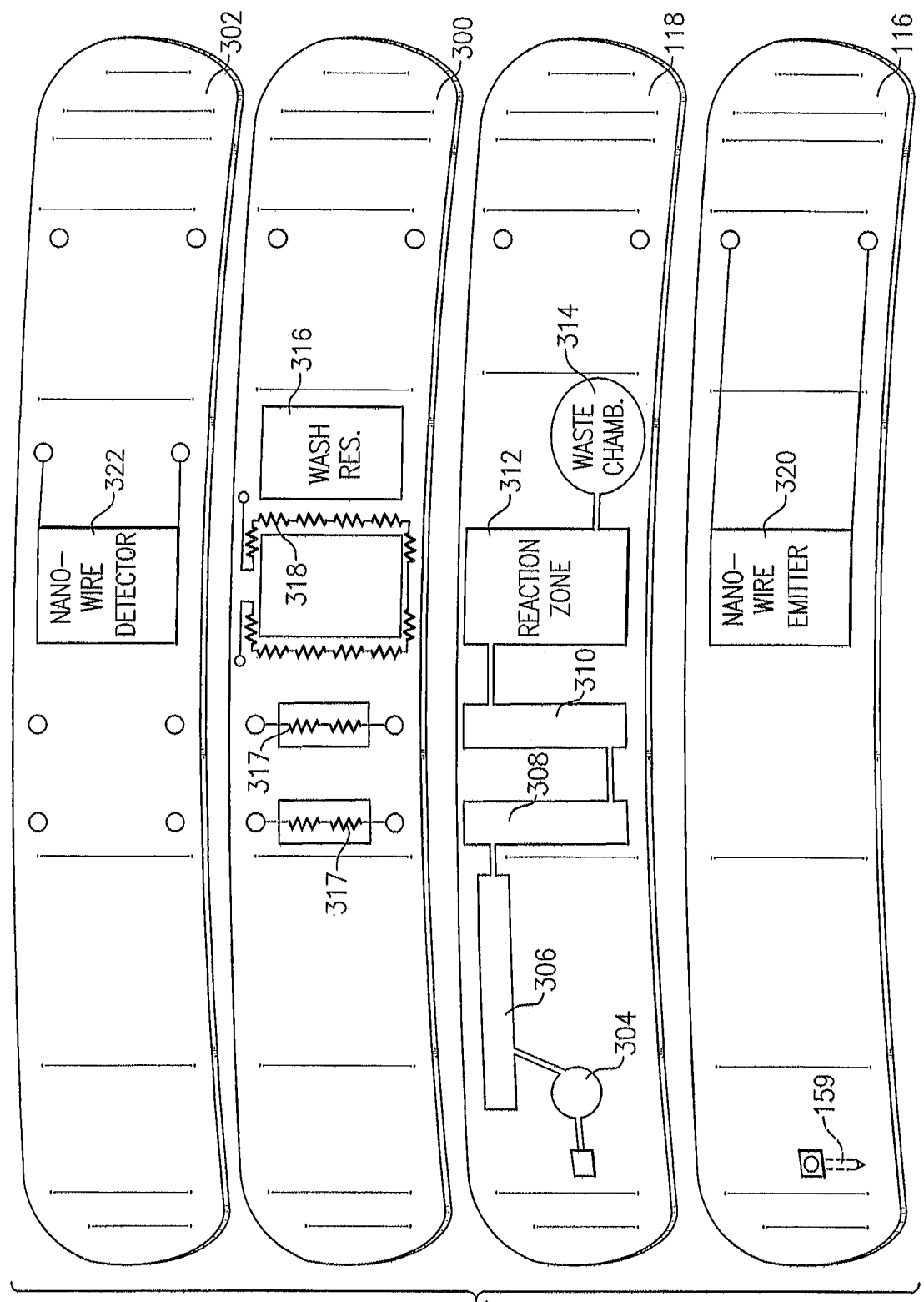
FIG. 11A is an exploded perspective view of a sample acquisition layer, fluidic circuit layer, heat and wash layer, and results detection layer as employed in one specific embodiment of the present personal diagnostic device implemented to perform a DNA assay.
Figure 11B:
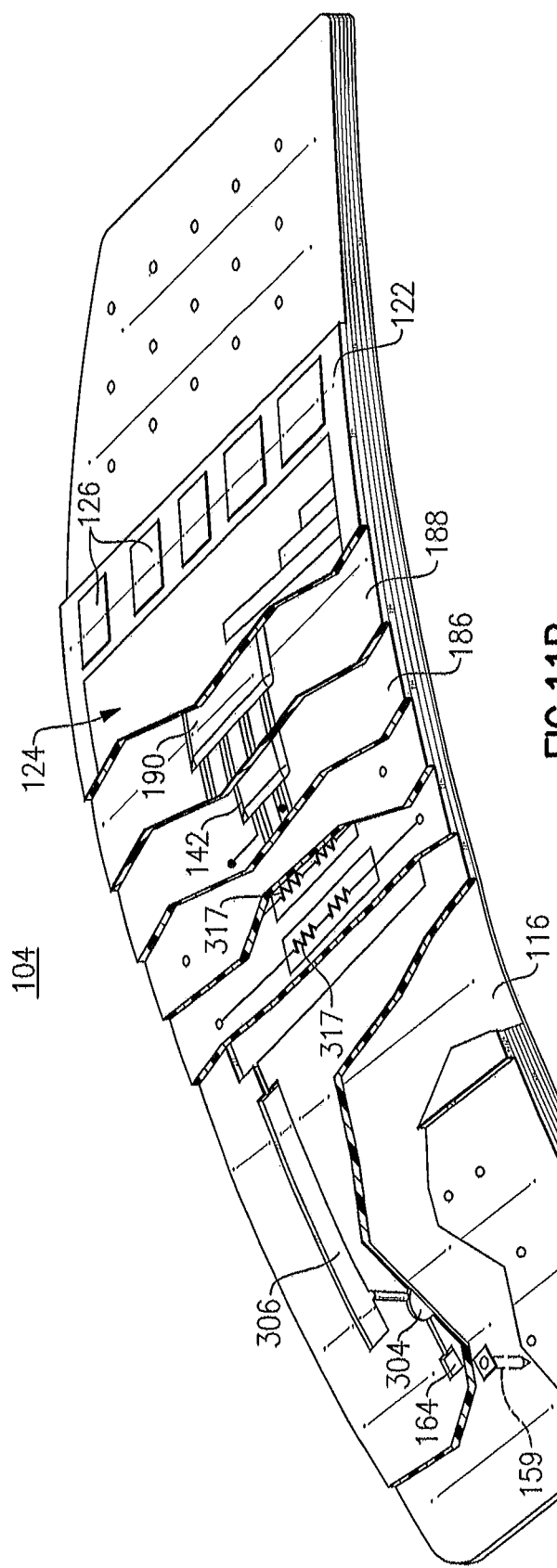
FIG. 11B is a perspective view with cut-away sections showing a fully assembled personal diagnostic device including the layers illustrated in FIG. 11A for performing a DNA assay.

With reference now to FIG. 11A, there are shown layers of an exemplary embodiment of the present invention for nucleic acid analysis including the base or sample acquisition layer 116, the fluidic processing layer 118, a fluid chamber and sample processing layer 300, and a specific assay results detection layer 302. These layers are similar to or a combination of the layers described above in conjunction with FIGS. 2 to 7B. As mentioned earlier, the layers are placed in register with each other such that a fluidic circuit is formed containing different chambers for sample processing, detection, and analysis. The fluidic circuit of the DNA patch may include the lancet or micro-probe 159 operatively connected to a blood metering chamber 304, a red blood cell (RBC) capture chamber 306, a cell lysis and DNA extraction chamber 308, a DNA shearing or DNA nicking and denaturing chamber 310, a capture or analysis or reaction chamber 312, a waste chamber 314, and wash buffer reservoir 316. All of which are operatively attached to each other to form the fluidic circuit. Chamber 308 may alternatively be two separate chambers for cell lysis and DNA extraction. As illustrated, wash buffer reservoir 316 is located in layer 300 which also includes heating elements 317 which are used to heat the sample to aid in cell lysis and denaturation of the DNA in the sample for analysis. Heating elements 317 are accordingly placed in register with lysis and DNA extraction chambers 308 and denaturation chamber 310. FIG. 11A further shows a light source 320 in layer 116 and a detector 322 in layer 302. Light source 320, analysis chamber 312, and detector 322 are in register with each other such that light emitted from source 320 passes through chamber 312 and is detected by the detector 322. The light source 320 and detector 322 are implemented in a nano-wire format described in further detail below FIG. 11B is a perspective view with cut-away sections showing a fully assembled personal diagnostic device 104 including the layers illustrated in FIG. 11A combines with the signal processing lay 186, the controller layer 188, and the input/output layer 122 for performing and reporting the results of the DNA assay described below in further detail.

FIGS. 12A to 12G next illustrate the steps of a method for detection of a nucleic acid sequence of interest using the DNA patch. FIGS. 12A to 12G show a simplified diagrammatic cross-sectional view of the fluidic circuit described above.

More particularly now, the first step is sample collection depicted in FIG. 12A. Blood sample is drawn by the microprobe 159 (FIG. 11A). A wide range of sample sizes, from 1 µl to 200 µl, and preferably 5- to 10 µl can be collected. The blood sample follows the fluidic circuit to the metering reservoir or chamber 304 of pre-determined volume. When the blood level in the metering chamber 304 reaches a pre-determined volume, the connection between the microprobe 159 and the metering chamber 304 is closed using a pinch or melt valve as shown and described below. A liquid sensor may be situated in the metering reservoir 304 such that when blood reaches that sensor, a signal is sent to the processor 142 which in turn closes the pinch or melt valve as described below in conjunction with FIGS. 13A and 13B. Blood from the metering chamber 304 is prevented from entering the RBC capture chamber 306 by a closed valve. This valve may be a dissolvable plug, FIG. 13E, that dissolves when it comes in contact with a liquid or a melt plug 324 (as shown). Melt plug 324 is made of a material that melts when heated such as wax. Plug 324 is preferably formed from inert biocompatible materials that melt when heated. Since heat is needed to open plug 324, a heating element 326 is embedded therein. When the reservoir is filled up to its pre-determined volume, the signal from the above-mentioned liquid also causes the processor to activate the heating element 326 which then melts plug 324. This opens the connection between the metering reservoir the RBC capture chamber 306 as shown in FIG. 12B and in further detail in FIG. 13B.

In order to effectively detect a target nucleic acid, it is usually necessary to isolate that nucleic acid from cellular and other specimen debris. It is also known that many target nucleic acids in whole blood are found in specific cell populations, such as in white blood cells (WBCs or leucocytes) as opposed to the red blood cells (RBCs or erythrocytes). RBC capture may be carried out using a solid support matrix, such as a membrane capable of lateral flow that contains a capture reagent for red blood cells. An example of membrane material which could be used is the high density or ultra high molecular weight polyethylene sheet material manufactured by Porex Technologies Corp. of Fairburn, Ga., U.S.A. This membrane has an open pore structure with a typical density, at 40% void volume, of 0.57 gm/cc and an average pore diameter of 1 to 250 micrometers, the average generally being from 3 to 100 micrometers. The membranes are from about 0.1 mm to 5.0 mm in thickness. While membranes made of polyethylene have been found to be highly satisfactory, membranes made from thermoplastic materials, e.g., polyvinyl chloride, polyvinyl acetate, copolymers of vinyl acetate and vinyl chloride polyamide, polycarbonate, polystyrene, and similar materials can also be used. A sponge-like matrix material, a three dimensional grid or micro-posts that span the height or width of the RBC capture chamber having attached thereto RBC capture agents such as lectin can also be used to remove RBCs from the blood sample. The RBC-binding reagent is immobilized on the solid support matrix using standard techniques, which are well known to those skilled in the art. The RBC capture agent used to immobilize the RBCs that is contained in the solid support matrix, such as those described above, is typically and most preferably an antibody, polyclonal or monoclonal, which is specific for red blood cells. Alternatively, other reagents which are known to bind RBCs, such as lectins or polymeric amino acids, e.g., polylysine and polyarginine, may also be used.

With continuing reference to FIG. 12B, the metered blood then enters the RBC capture chamber 306, the blood sample is prevented from flowing back into the metering reservoir by a detent pressure valve 330 (further described below in conjunction with FIG. 13A). When chamber 306 is filled, it may be sealed off by a melt valve 332, as demonstrated in FIG. 12C showing the melt valve in a closed position 334. Melt valve 332 is similar to valve 324 but is used to close fluidic circuits instead of open them. Melt valves can be controlled as discussed above by the processor using the heating element 326 wherein the valve is melted into the fluidic circuit effectively blocking portions of the circuit at desired time points during the assay process. Each of the chambers in the fluidic circuit may include a vent port 340 that allows air within the chamber to escape thereby preventing air blockages within the fluidic circuit. Vent port 340 may include a filter 342 that prevents contamination of the sample while allowing air to pass through.

Figure 12E:
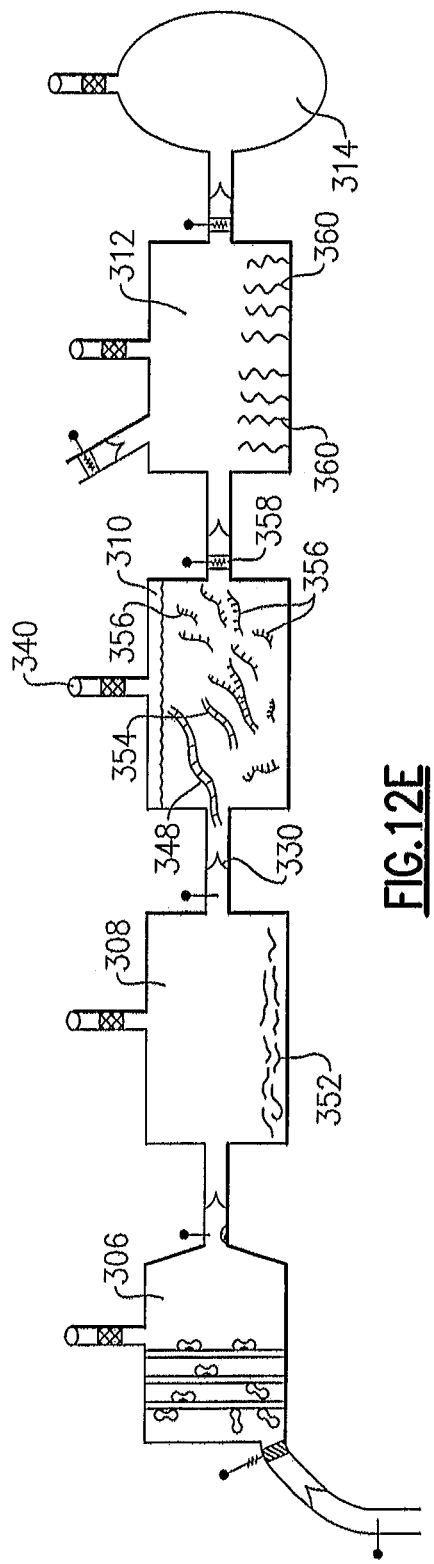

RBCs are separated from the sample within chamber 306. In the illustrated example, RBCs 334 are captured on micro-posts 328 coated with a RBC capture agent. After allowing sufficient time for RBC capture, a second melt plug 344 is opened (FIG. 12D) allowing the WBCs 338 in chamber 306 to flow into the cell lysis and DNA extraction chamber 308. The sample containing WBCs is prevented from flowing back into chamber 306 by a detent pressure valve 330 situated between chamber 306 and 308. The white blood cells which contain genetic material may be moved by capillary action to the lysis chamber 308 which contains pre-immobilized lysing reagent. Various lysing procedures are well known to those skilled in the art, including freezing, treatment with digesting enzymes such as proteases (for example, Proteinase K), boiling, and use of detergents (see for example U.S. Ser. No. 178,202, filed Apr. 6, 1988 by Higuchi, and EP-A-0 428 197, published May 22, 1991). By way of non-limiting example, a lysis reagent containing guanidine isothiocyanate and Triton X-100 detergent, and Proteinase K, which facilitates the release of nucleic acid from lyzed WBCs 346 can be used. Double stranded DNA 348 is released from the lysed WBCs 346 and is extracted from the solution. The extraction of DNA from white cells can be carried out using commercially available magnetic beads that allow extraction of nucleic acids without organic solvents. By way of non-limiting example, Dynabeads DNA Directs that allows for the rapid isolation of DNA from small volumes of blood can be used. In one embodiment hereof, these beads are preloaded into the lysis chamber and upon application or removal of the magnetic field; the DNA is isolated from other cellular materials and eluted (step not shown). After the DNA is extracted or isolated, the solution containing the isolated DNA is then moved into the DNA nicking and denaturation chamber 310 by opening a third melt plug 350 as represented in FIGS. 12D and 12E. FIG. 12E also depicts remaining WBC cell membranes 352 in chamber 308 after the cell lysis and DNA isolation step described above. The double stranded DNA 348 is sheared or nicked in chamber 310 into short double stranded DNA fragments 354 which are then denatured into single stranded DNA fragments 356.

Figure 12F:
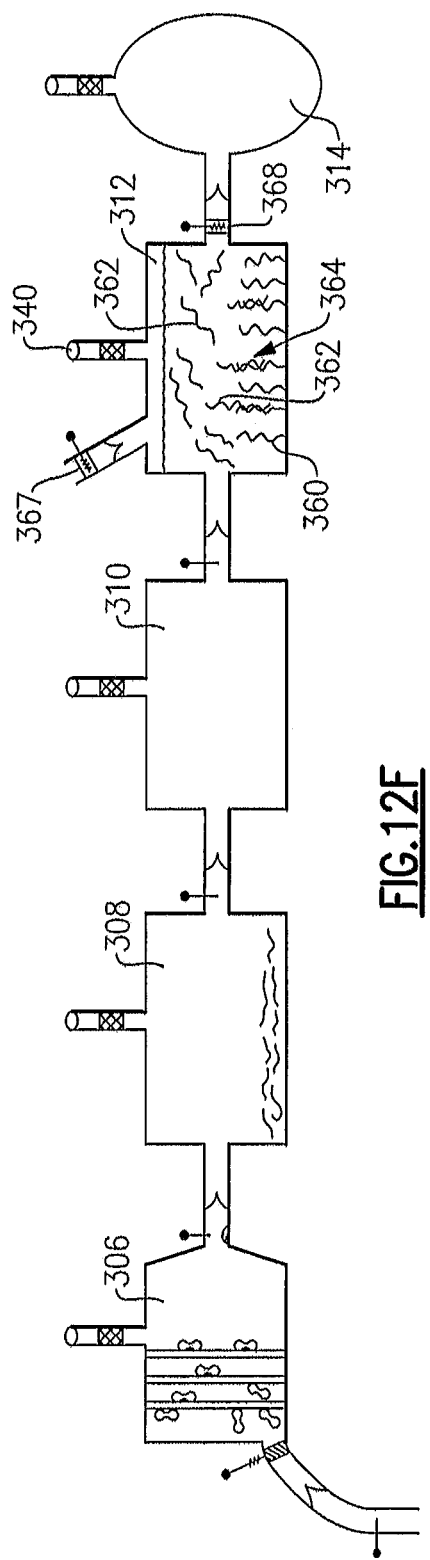

The genomic DNA extracted can be sheared by using restriction enzymes which are preloaded in the nicking chamber 310. The methodologies for genomic DNA digestions are well known to those skilled in the art. The temperature in this chamber can be controlled via heating elements 316. Alternatively, magnetic beads may be used to promote the shearing of the genomic DNA, thus facilitating target capture. The solution in the nicking chamber containing the double stranded DNA fragments 354 may be heated up to between about 65° C. and 75° C. to thereby denature the double stranded DNA 354. After the DNA denaturation step, a fourth melt plug 358 (FIG. 12E) is opened to allow the sample containing the single stranded DNA fragments 356 to enter the analysis chamber 312. The analysis chamber 312 has nucleic acid capture probes 360 which are attached to a capture zone. Each of the probes 360 may be attached to a single capture zone. Any target DNA 362 in the sample is then allowed to hybridize with the capture probe 360 to thereby "capture" the target nucleic acid in the target zone for detection as illustrated in FIG. 12F and later described in further detail in conjunction with FIGS. 14A to 14G. Capture DNA may be single stranded or partially double stranded near its attachment point to the capture zone. The double strand is located at the reactive end, such as the amino end, of the probe where it is attached to a solid support like the capture zone because a double strand has been found to more effectively project the capture probe erectly or upwardly from the active layer as compared to ssDNA in some instances. An extension or spacer including, for example, ssDNA and PEG (polyethylene glycol), may be used to extend the probe further from the surface so as to increase the hybridization efficiency of the capture probe with the target. Furthermore, to prevent the capture probes from collapsing onto the solid phase and to prevent the target and non-target nucleic acid sequences from binding non-specifically onto the capture zone, the capture zone surface can be treated with standard blocking buffers well known to those skilled in this particular art. The sequence of the capture DNA is selected so as to hybridize directly with target DNA or RNA, thereby forming a partially double stranded complex 364 comprising capture DNA, target DNA or RNA (FIG. 12F).

The length of the capture probes can be from 15 to 70 bases long, preferably 25 to 40 bases long. The attachment of DNA probes to the solid support in the capture zone can be achieved by covalent or non-covalent attachment strategies, which are well known to those skilled in this art.

Probe density is a critical factor for the efficiency of target capture as well as the kinetics of the target and probe hybridization. According to studies reported on the effect of surface probe density on DNA hybridization (Nucleic Acid Research, 2001, Vol. 29, number 24, pages 5163-5168), the probe density strongly affects the target hybridization efficiency. The hybridization efficiency is optimal when the probe density is below $2 \times 10^{12}$ probes/cm$^2$, preferably $1 \times 10^{11}$ probes/cm$^2$ to $1 \times 10^{12}$ probes/cm$^2$.

Figure 14B:
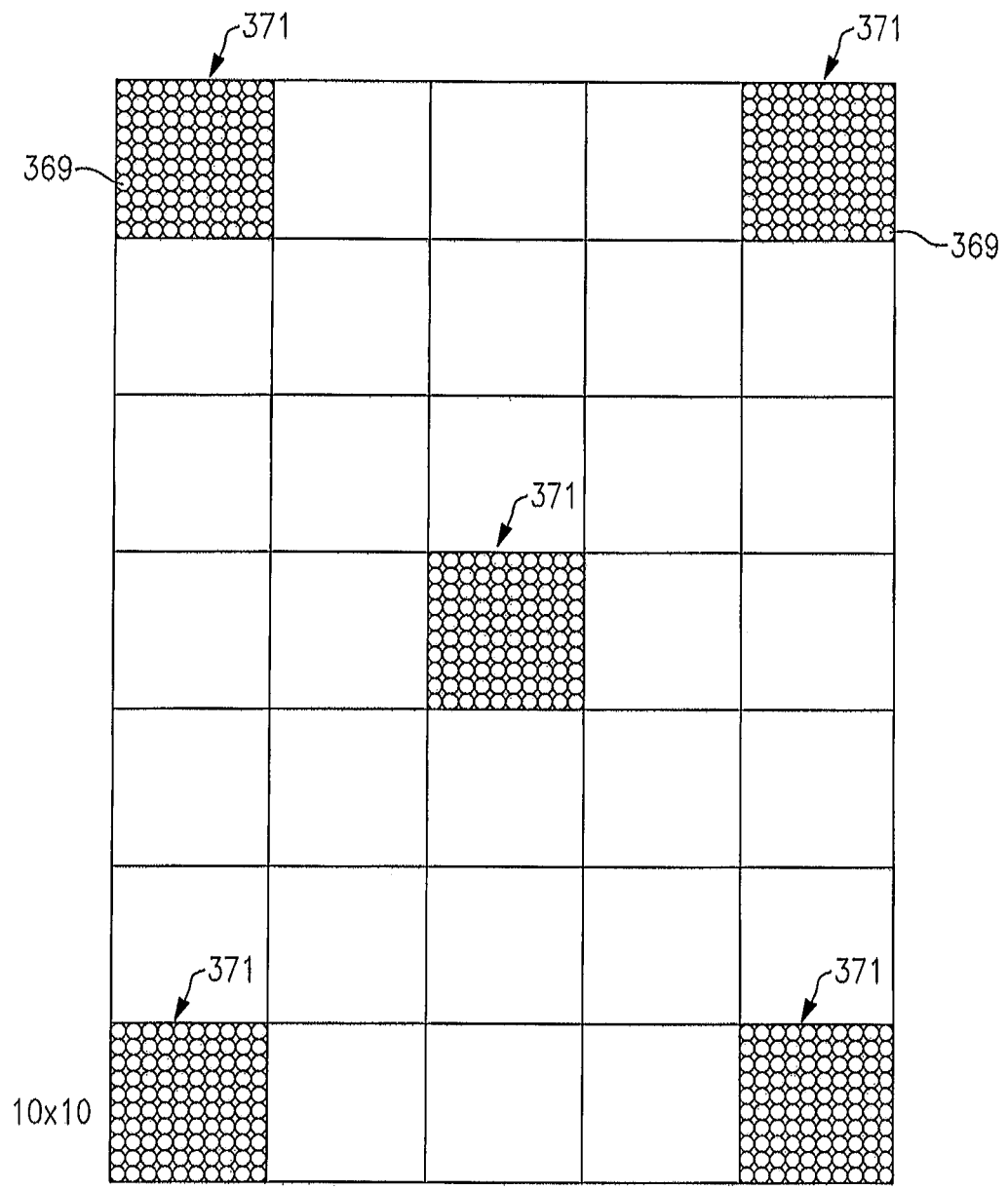

The capture probes can be immobilized on the nano-wires directly in the format of a capture unit 371, FIG. 14B. Each capture unit 371 may consist, for example, of one hundred 5 nm diameter nano-wires for an area of 50 nm×50 nm, as illustrated in FIG. 14B. The probe density on each capture unit may vary from 1 to 100 probes per capture unit, and preferably about 10 capture probes/capture unit of area 50 nm×50 nm. The total number of capture units per reaction zone in the assay area may vary from $10^6$ to $5 \times 10^6$, and preferably about $10^6$. The capture units may be distributed over an area from about $10^{-4}$ cm$^2$ (for example a square of dimensions 0.1 mm by 0.1 mm) to about $10^{-2}$ cm$^2$ (1 mm by 1 mm), and preferably about $10^{-4}$ cm$^2$. The spacing between the capture units on the capture area can vary from none to 10 as represented in FIG. 14B. The total number of capture probes in the entire reaction zone 312, FIG. 11A, may range from about $10^6$ to about $5 \times 10^7$, and preferably on the order of about $10^7$.

When target RNA or DNA of a specific sequence is present in the test sample, the target RNA or DNA hybridizes with the capture DNA. In this manner, the target DNA is retained within the reaction zone 312, as discussed above. The hybridization step can be performed at room temperature or higher in any standard buffer well known to those skilled in the art. By way of non-limiting example, a standard buffer containing 5×SSC, 0.1% (w/v) N-lauroyl-sarcosine, 0.02% (w/v) SDS, 1% Blocking Reagent can be used for this purpose. Hybridization may be further facilitated by heating the analysis or reaction chamber 312. The hybridization procedure can be performed from a few minutes up to several hours.

Figure 12G:
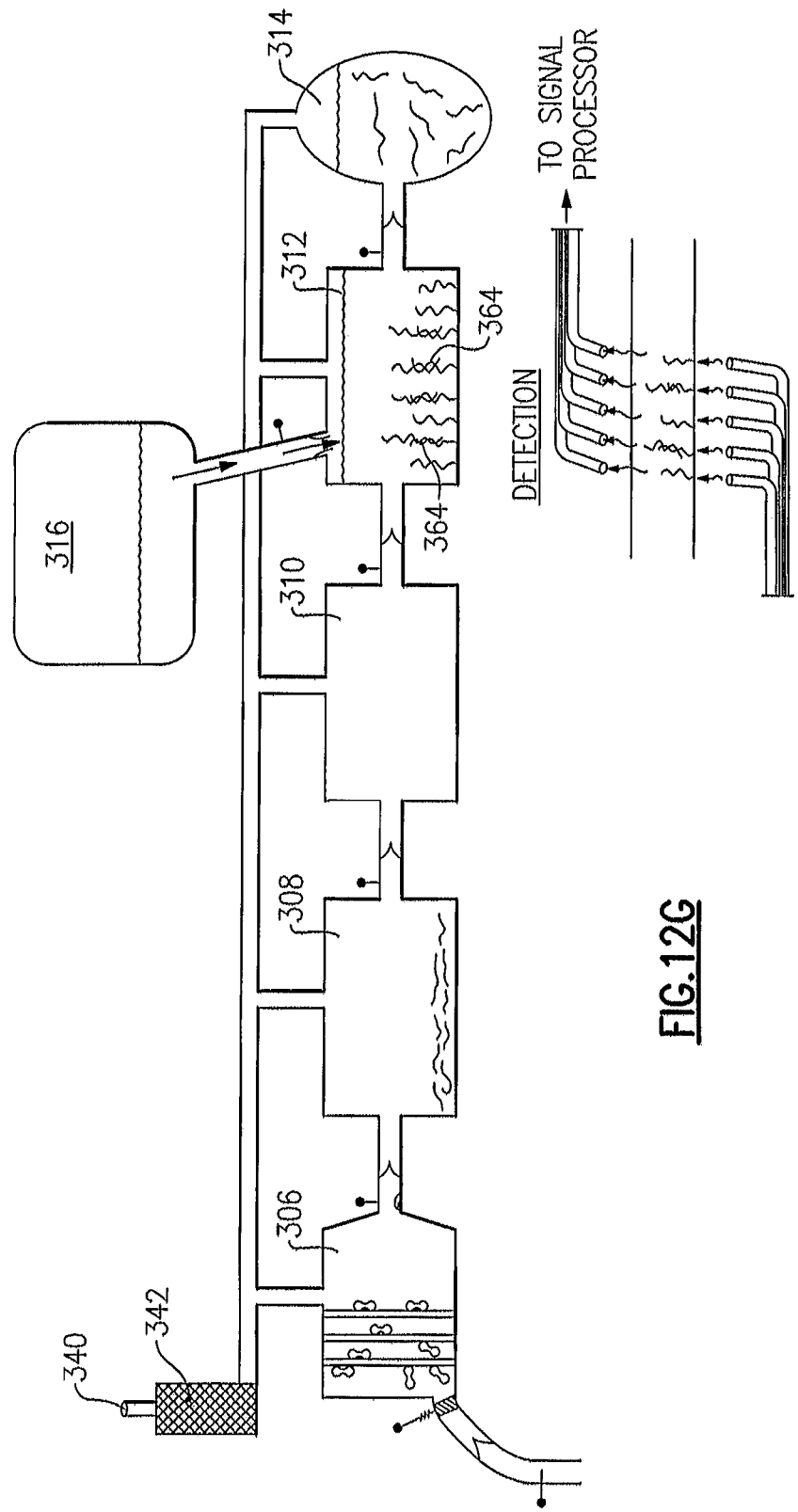

With reference now to FIG. 12G, there is shown the last steps of the analysis method. After hybridization, the reaction zone 312 may be washed to get rid of any unattached single stranded nucleic acid sequences. The wash process may be initiated by a time-controlled opening of a fifth melt plug 367 connecting the wash reservoir 316 to the analysis chamber 312 (FIG. 12F). Wash buffer 366 stored in the wash reservoir 316 is released into the analysis chamber, as shown, to wash the capture zone of unbound DNA or RNA. The wash can be performed at high temperature to minimize or eliminate any non-specific binding. A fifth melt plug 368 (FIG. 12F) is opened allowing the wash buffer and sample to be emptied into the waste chamber 314 (FIG. 12G) removing unbound nucleic acid sequences from the analysis chamber 312.

With continuing reference to FIG. 12G, an alternate embodiment of the fluidic circuit described in conjunction with FIGS. 12A to 12F is shown. In the embodiment of FIG. 12G, the vents from each chamber are interconnected as shown. Quantification of the complex 364 can be carried out by image analysis, pattern recognition, or optical interference as presented in Table 1 above. The required resolution to distinguish the double stranded DNA resulted from target capture from the single stranded capture probe can be achieved using the nano-wire technology of the present invention described below in more detail connection with FIGS. 14A to 14G. FIG. 12G also illustrates nano-wire bundles associated with each capture probe used as a light source and a detector. As shown, the nano-wire bundle on the bottom emits a focused light through the capture or reaction zone containing a single capture probe or complex 364, since complex 364 is significantly larger than the single stranded probe, the optical motion or the surface interrogation pattern of the double stranded DNA 364 as detected by the nano-wire detectors will be distinct from those of a single probe. This difference can thus be detected and the number of complexes 364 quantitated.

Figure 13A:
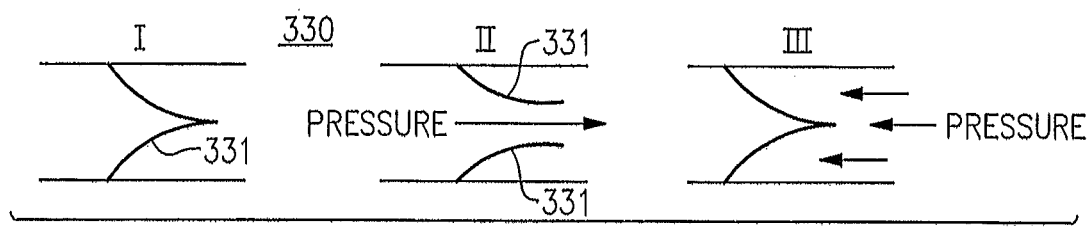
FIG. 13A is a diagrammatic representation of a pressure valve utilized in the fluidic circuits of the present invention to control the flow of fluids.

Referring now to FIGS. 13A to 13E, there are shown several flow control elements and related methods as employed herein to direct and control fluid flow in a timed and pre-determined manner as may be centrally controlled by the signal processing unit 142 and the logic controller 190 illustrated, for example, above in FIGS. 7B and 11B. More specifically, FIG. 13A is an enlarged detailed diagrammatic representation of the detent pressure valve 330 utilized in the fluidic circuits of the present invention to control the flow of fluids. As illustrated the detent pressure valve 330 includes a pair of detent lips 331 which are each provided with a pre-stressed to hold them together in a normally closed position as shown in FIG. 13A-I. When the down stream pressure in the flow channel is less that the pressure upstream of the pair of detent lips 331, and the pressure difference therebetween is greater than the pre-stressed force holding the detents 331 in a normally closed condition, the detents 331 will open and allow flow as illustrated in FIG. 13A-II. After the pressure normalized up stream and down stream of the detents 331, the pre-stress force will close the valve as illustrated in FIG. 13A-III. As further illustrated, the detents 331 are shaped to prevent back flow in the channel.

Figure 13B:
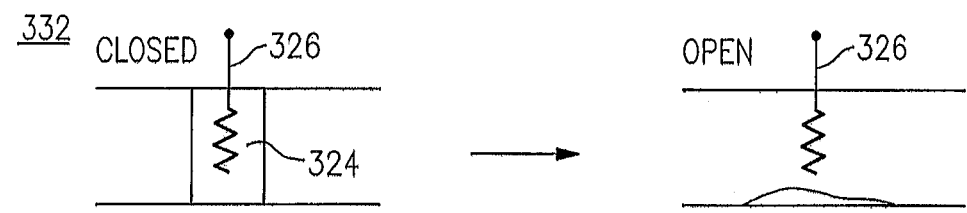
FIG. 13B is a schematic presentation of a normally closed melt valve employed in the fluidic circuits of the present invention to control and direct the flow of fluids therein.

FIG. 13B is a schematic presentation of a normally closed melt valve 332 employed in the fluidic circuits of the present invention to control and direct the flow of fluids therein. The normally closed melt valve 332 includes the heating element 326 positioned in the melt plug 324. Upon receiving a signal from the signal processing unit 142 and/or the logic controller 190 illustrated, for example above in FIGS. 7B and 11B, the heating element 326 receives a charge of current, heats to a predetermined temperature, and then melts the melt plug 324 to thereby open the channel and allow flow therein.

Figure 13C:
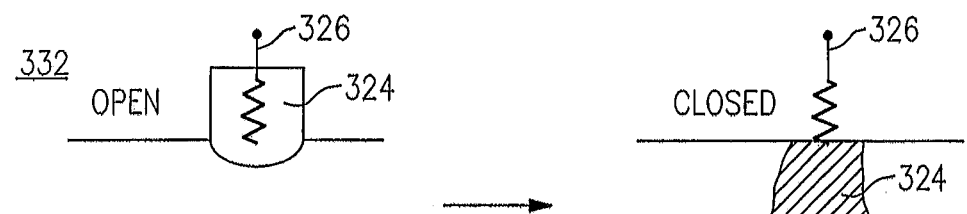
FIG. 13C is a schematic representation of a normally open melt valve used in the fluidic circuits of the present invention to direct and control fluid flow.

FIG. 13C is a schematic representation of a normally open melt valve 332 used in the fluidic circuits of the present invention to direct and control fluid flow. The normally open melt valve 332 includes the heating element 326 positioned in the melt plug 324. As illustrated, the melt plug 324 is positioned above the flow channel to normally allow flow. Upon receiving a signal from the signal processing unit 142 and/or the logic controller 190, the heating element 326 receives a charge of current, heats to a predetermined temperature, and then melts the melt plug 324 to thereby close the channel and prevent further flow therein.

Figure 13D:
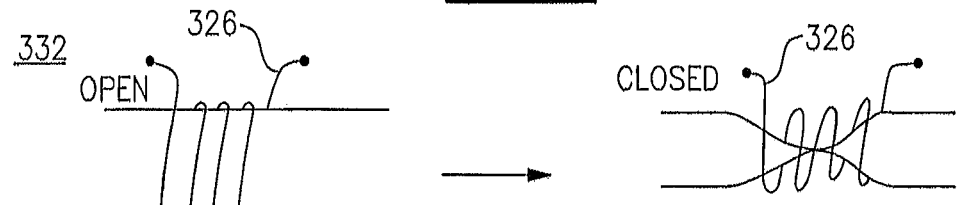
FIG. 13D is a schematic presentation of another normally open melt valve used in the fluidic circuits of this invention to control fluid flow.

FIG. 13D is a schematic presentation of another normally open melt valve or pinch valve 332 used in the fluidic circuits of this invention to control fluid flow. In this embodiment, the heating element 326 is wrapped around the flow channel as illustrated. The flow channel is made of a material that contracts when heated. Thus when the heating element 326 receives a signal from the signal processing unit 142 and/or the logic controller 190, the heating element 326 receives a charge of current, heats to a predetermined temperature, and then causes the channel to collapse and contract to thereby close the channel and prevent further flow therein.

Figure 13E:
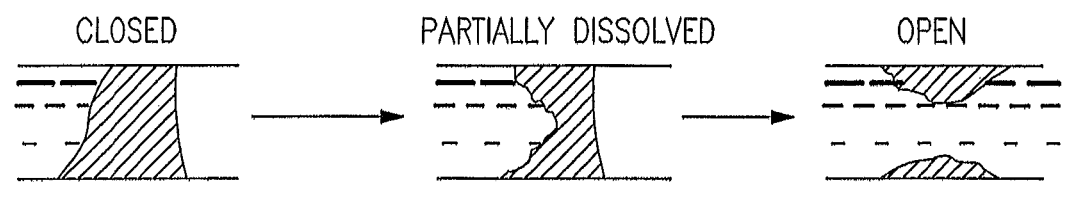
FIG. 13E is a diagrammatic representation of a dissolvable plug used to form a timed fluid valve shown closed, partially dissolved, and then open to allow flow.

FIG. 13E is a diagrammatic representation of a dissolvable plug used to form a timed fluid valve shown closed, partially dissolved, and then open to allow flow. In this embodiment, a biocompatible material that dissolves upon contact with a fluid is pre-loaded in the channel which is dry until use of the device 104 in an intended manner. Upon use of the device, a fluid such as blood, sweat, or interstitial cell fluid (ICF) from the user is introduced into the channel. Once the dissolvable plug is in contact with the fluid in the channel, the plug begins to dissolve. With proper selection of the composition of the plug material, the dissolvable plug may be designed to dissolve after a pre-determined time duration starting from the point of first contact by fluid in the channel. In this embodiment, fluid control is passively achieve, rather than actively achieved by intervention from the signal processing unit 142 and/or the logic controller 190 as in the case of the flow elements discussed above in connection with FIGS. 13B, 13C, and 13D.

Turning now to FIGS. 14A to 14K, there are shown several detailed isolation views of semi-conductor nano-wire and micro-wire assemblies utilized in various embodiment of the present invention as light emitters and detectors for illuminating, detecting, and imaging assay results obtained in the reaction zones or capture zones of the personal diagnostic devices hereof.

Generally, the inventors hereof propose that semi-conductor nano-wires and micro-wires represent a unique material system for investigating low dimensional biochemistry. Such nano-wire elements, components, and systems are anticipated to play increasingly important roles as both interconnects and functional device elements in nano-scale electronics, optoelectronics, MENS, bio-MENS, and nano-scale bio-chemical systems. Such biological and bio-chemical applications are utilized herein. These small wires are made from semi-conductor material. They include silicone (Si) that is doped with all known, traditional, or newly created or discovered dopants to produce different various desired semi-conductor materials. The nano-wire may be used as light tubes or optical fibers with a diameter as small of 5 nm. The wires can conduct current, produce laser light, or detect incident light. The inorganic semi-conductor nano-structures may be custom fabricated with virtually any desired composition, size, shape, crystal structure, doping, and surface chemistry characteristics. The semi-conductor nano-structures currently being developed commercially include three major categories: nano-dots, nano-rods, and nano-wires. In addition, it has been reported that more complex shapes, such as cones, teardrops, and tetra-pods are also possible.

As utilized herein for certain applications, the nano-wires may be employed as nano-piercing probes for intracellular illumination and/or detection. Additionally, the nano-wires and micro-wires may be prepared by chemically treating and functionalizing the surfaces thereof. In this manner, the need for performing the assays in a separate reagent layer or capture layer is eliminated. The nano-wires can be made of a semi-conductor material that is electrochemically responsive. That is, if a chemical reaction takes place, be it exothermic or endothermic, the nano-wire will detect a change in local temperature and measure the heat absorbed or produced. Also, a change in electrical conductivity in an electro-chemical results assay may be detected by a nano-wire or micro-wire implemented as an electrode and then converted to an electrical signal which is processed by the processor 142 and/or the logic controller 190 illustrated in FIGS. 7B and 11B to thereby produce a readable results display on the video display monitor 124 or the fixed results display windows 126 illustrated in FIGS. 2-6 and FIG. 7B.

FIG. 14A shows 5 by 5 a bundle of nano-wires 365 comprised of individual semi-conductor wires 369 on the nano-scale or micro-scale in diameter. For convenience, the individual semi-conductor wires 369 hereinafter are alternatively referred to as either "nano-wires 369" or "micro-wires 369" depending on the specific application.

Figure 14F:
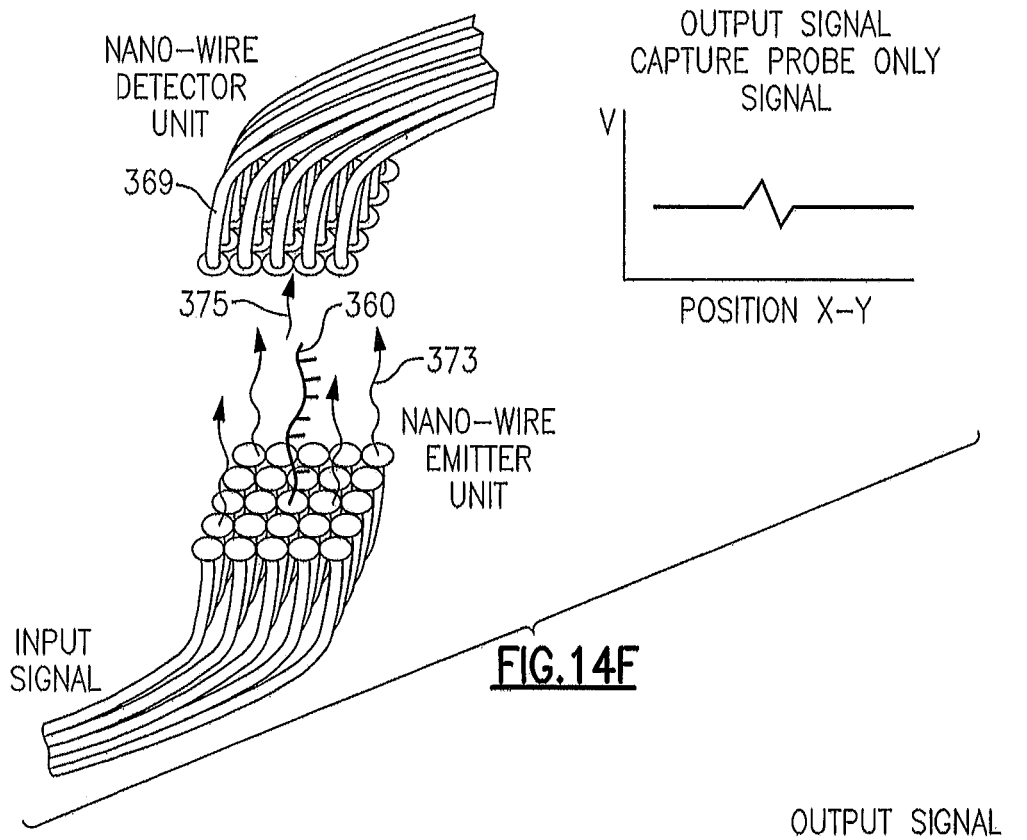
Figure 14G:
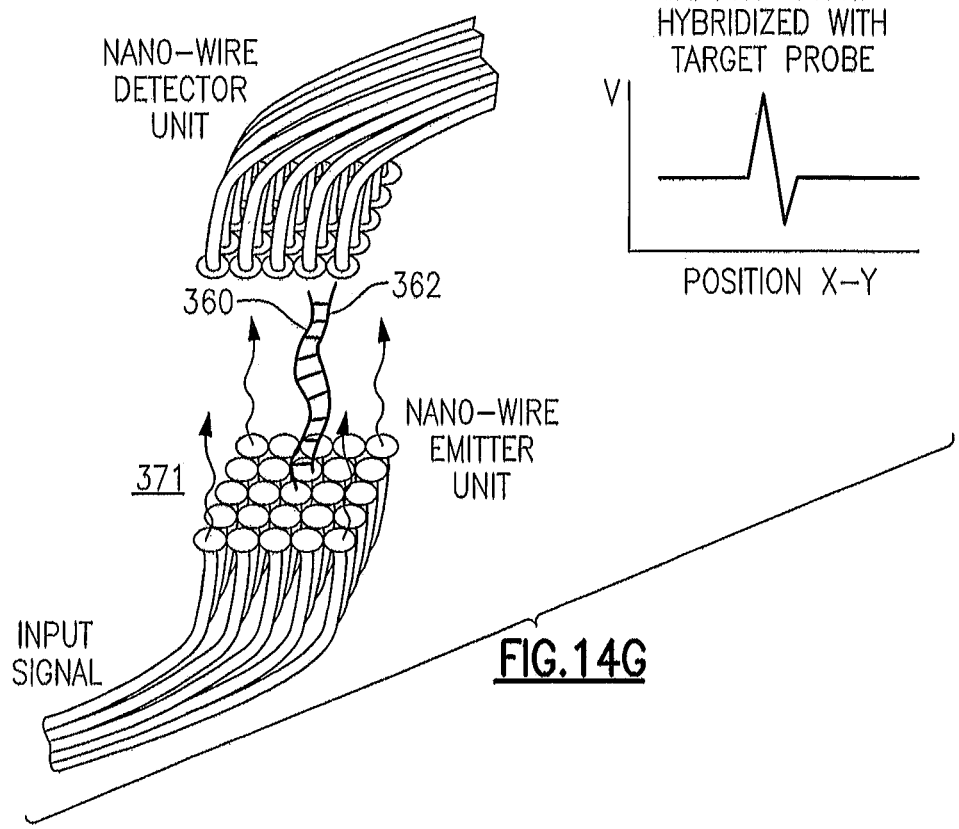
Figure 14H:
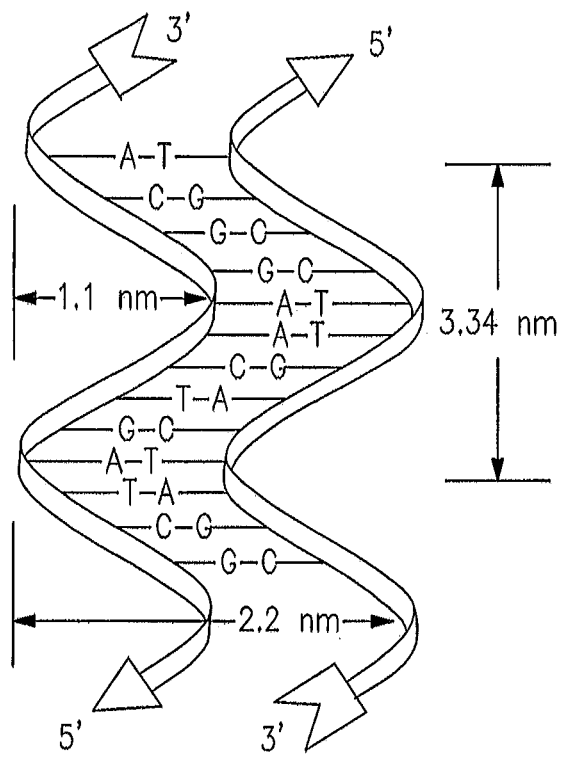

As discussed above, the 5 by 5 bundle 365 may be employed as a capture unit 371, FIG. 14B. The DNA capture probes 360 in the assay discussed above are immobilized on the nano-wires directly to form the capture units 371 as illustrated FIG. 14B. The capture units 371 may include any number of individual nano-wires 369 in any preferred geometric arrangement and any desired number and placement of DNA capture probes 360 as illustrated in FIG. 14C. Each capture unit 371 may consist of, for example, one hundred 5 nm diameter nano-wires for an area of 50 nm×50 nm, as illustrated in FIG. 14B and preferably utilized in the above DNA assay. The spacing between the capture units 371 as arranged in the assay reaction zone may be of any desired or preferred density or distribution. As illustrated in FIG. 14D the individual nano-wires 369 may be individually addressable so that a signal from each nano-wire may be processed by the signal processor 142 and/or the logic controller 190. FIG. 14D shows an emitter unit and a detector unit each formed by a bundle of nano-wires. In this configuration, the individual nano-wires 369 in the emitter unit are enabled to emit an incident beam of light or electro-magnetic energy 373 of a pre-determined wave length. As further illustrated, individual nano-wires 369 in the detector unit are enabled to detect the incident beam 373 and generate an output signal associated therewith. When there is an absence of any matter positioned between the emitter unit and the detector unit, the incident energy 373 on the detector unit may be converted to a baseline output signal in the form of a steady state flat output as illustrated in the graph of FIG. 14E. FIG. 14F shows the nano-wire emitted unit with a DNA capture probe 360 secured in the center thereof. Thus according to one aspect of this invention, when incident energy 373 is applied to the emitter unit by a directed input signal there will be a light/matter interaction between some of the incident electro-magnetic energy 373 and the DNA capture probe 360 to thereby produce electro-magnetic energy that has been modified by this light/matter interaction. Thus a modified electro-magnetic beam 375 will be detected by some of the individual nano-wires 369 in the detector unit as illustrated in FIG. 14F. Thus the output signal generated by the nano-wire detector unit will include a perturbation in the baseline signal as illustrated in the graph of FIG. 14F. After hybridization between a respective capture probe 360 and a complementary target probe 360, a double stranded segment of DNA is formed in the area of the capture unit 371 as illustrated in FIG. 14G. The scientifically determined and reported dimensions of a segment of double stranded DNA are shown in FIG. 14H. Since the nano-wires may be made as small as at least 5 nm and the dimensions of a segment of double stranded DNA are on the same order, FIG. 14H, there will be a detectable difference between the output signal generated by the light/matter interaction associated with ssDNA and that associated with double stranded DNA as represented by a comparison for the graphs of FIGS. 14F and 14G.

Figure 14K:
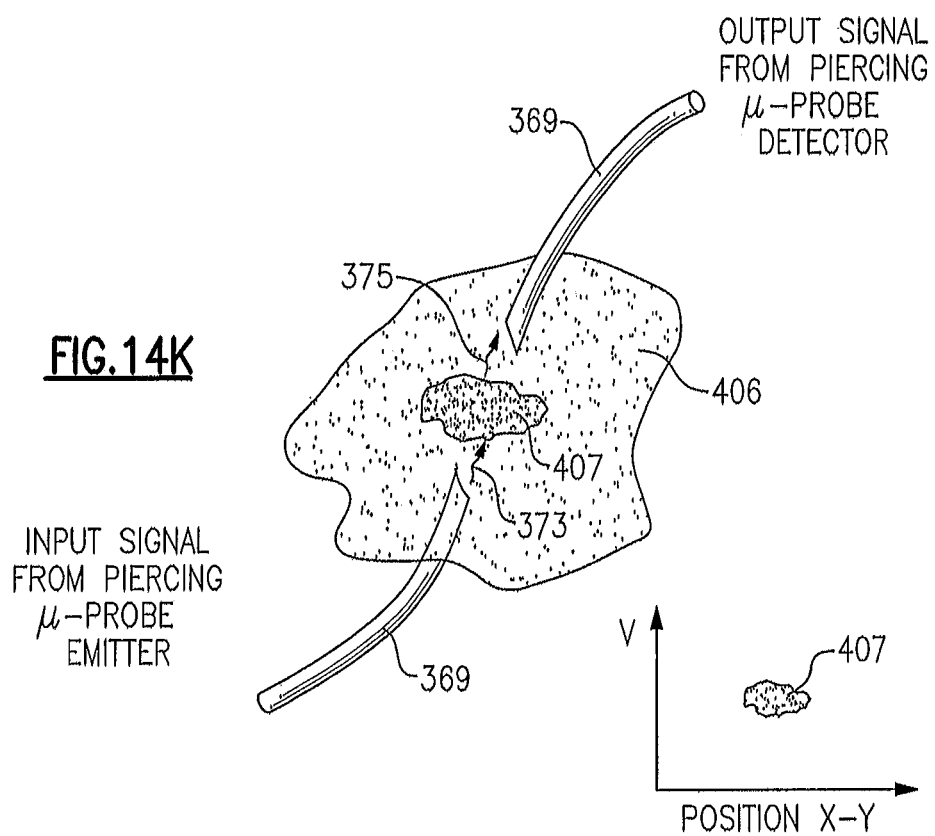
Figure 14I:
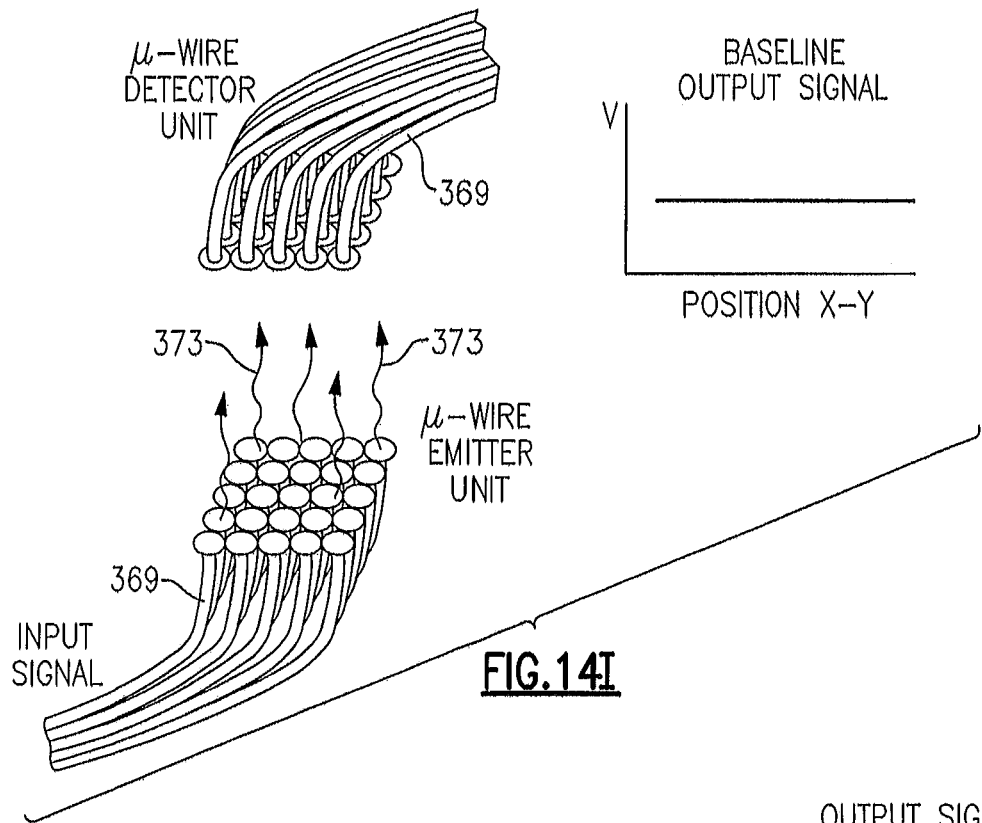
Figure 14J:
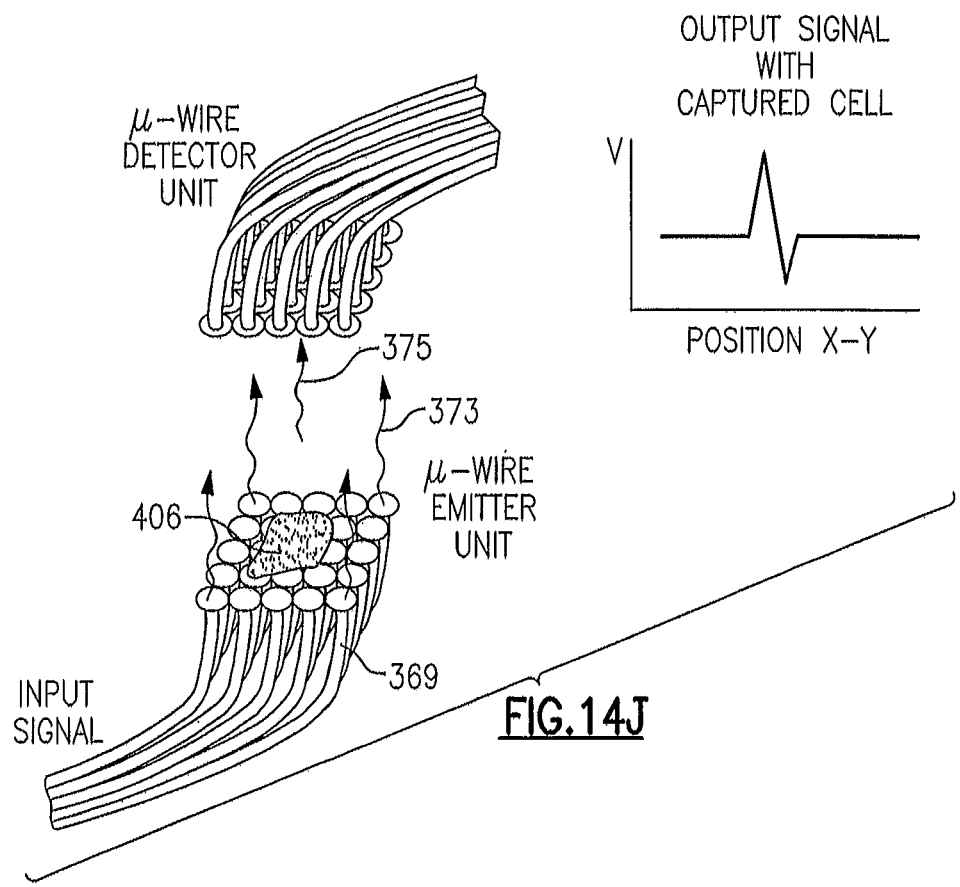

FIGS. 14I and 14J are views respectively similar to FIGS. 14F and 14G. In this embodiment, the individual semiconductor wires 369 are of a diameter on the order of microns, preferably 1 to 5 microns for the intended cellular detection and imaging applications illustrated in FIGS. 14F and 14G, and in further detail herein below. The μ-wire emitter unit shown in FIG. 14I similarly produces incident electro-magnetic energy 373 which may be detected by the μ-wire detector unit to generate a baseline output signal as illustrated. In FIG. 14J, a captured cell 406 is shown bound specifically to the μ-wire emitter unit. As illustrated, the μ-wire emitter unit emits incident energy 373 some of which interacts with the captured cell 406 to produce modified electro-magnetic energy 375. Both the incident energy 373 and the modified electro-magnetic energy 375 are detected by the μ-wire detector unit to produce an output signal indicative of the captured cell 406. Since blood cells, for example, are of a size on the order of microns, (RBCs about 3×5 μm and WBCs about 8 to 15 μm) the sizing of the individual semi-conductor wires 369 on the order of microns is suitable for the purposes intended in the present cellular assays discussed below in further detail.

In FIG. 14K, there is shown a captured cell 406 with a nucleus 407. As a further application of the micro-wires described herein, it is proposed that micro-wires may be designed as piercing μ-probe emitters and piercing μ-probe detectors that penetrate the cell wall and are thus employed to obtain signal information derived by intracellular illumination and detection. In this manner, the piercing μ-probe emitter produces incident energy 373 which is modified by interaction with, for example, the nucleus 407 to produced modified electro-magnetic energy 375 which in turn is detected by a corresponding piercing μ-probe detector to produce an output signal that may be converted to an image as illustrated. In this manner, useful intracellular information such as the morphology of the nucleus 407 may be obtained by the methods and apparatus so described.

Cellular Assay Implementations and Methods

The immune system is made up of cells and organs that protect the human body from outside invaders such as bacteria, viruses, fungi, and parasites (germs) that can cause infection, disease, and even death. The immune system also eliminates abnormal cancerous cells that are growing out of control. When functioning properly, the immune system fights off infection and keeps a person healthy. But when it malfunctions, germs that enter the body can more easily cause disease or death. Two very important cell types that play a significant role in the immune system are Helper T cells (also known as CD4 cells) and suppressor T cells, known as CD8 cells. The human acquired immune deficiency syndrome (AIDS) is characterized by a depletion of Helper T cells (CD4 bearing cells or CD4+ cells). Upon infection with HIV, CD4+T-Helper cells are rendered non-functional and become depleted. The depletion of these CD4+ lymphocytes leads to immunosuppression, with the patient becoming susceptible to a wide range of opportunistic infections and malignancies.

The ratio of the CD4+ and CD8+ cells, and the absolute counts of CD4+T Helper cells are the current standard used to monitor the progression of the HIV infection to AIDS. During the course of an infection, the number of CD8+ cells remains constant, while the number of CD4+ cells present in the blood fall precipitously. The ratios of CD4+/CD8+ and the absolute CD4+ count in patients who are treated with pharmacological agents for the virus can be an important indicator of whether their system has developed drug-resistant viral strains.

Currently, a measurement of the CD4+/CD8+ ratio and the absolute CD4+ count requires the use of a high-priced cell sorting machine, or cytometer. Furthermore, specialized technical personnel with a high degree of expertise are required to operate the cytometer. Therefore, the development of portable, easy to use, and inexpensive diagnostic devices, which are capable of quantifying the CD4+/CD8+ ratio and absolute CD4+ counts in real-time, is of particular interest.

The personal diagnostic device 104 of the present invention may be used for cellular assays such as CD4+ and CD8+ cellular analyses. The cellular analysis device is also herein referred to as a cellular patch or bracelet which could provide a quick, easy-to-use, and inexpensive method for diagnosing and monitoring the progression of an HIV infection using only a simple patch or bracelet that interfaces with a personal computer.

Figure 15A:
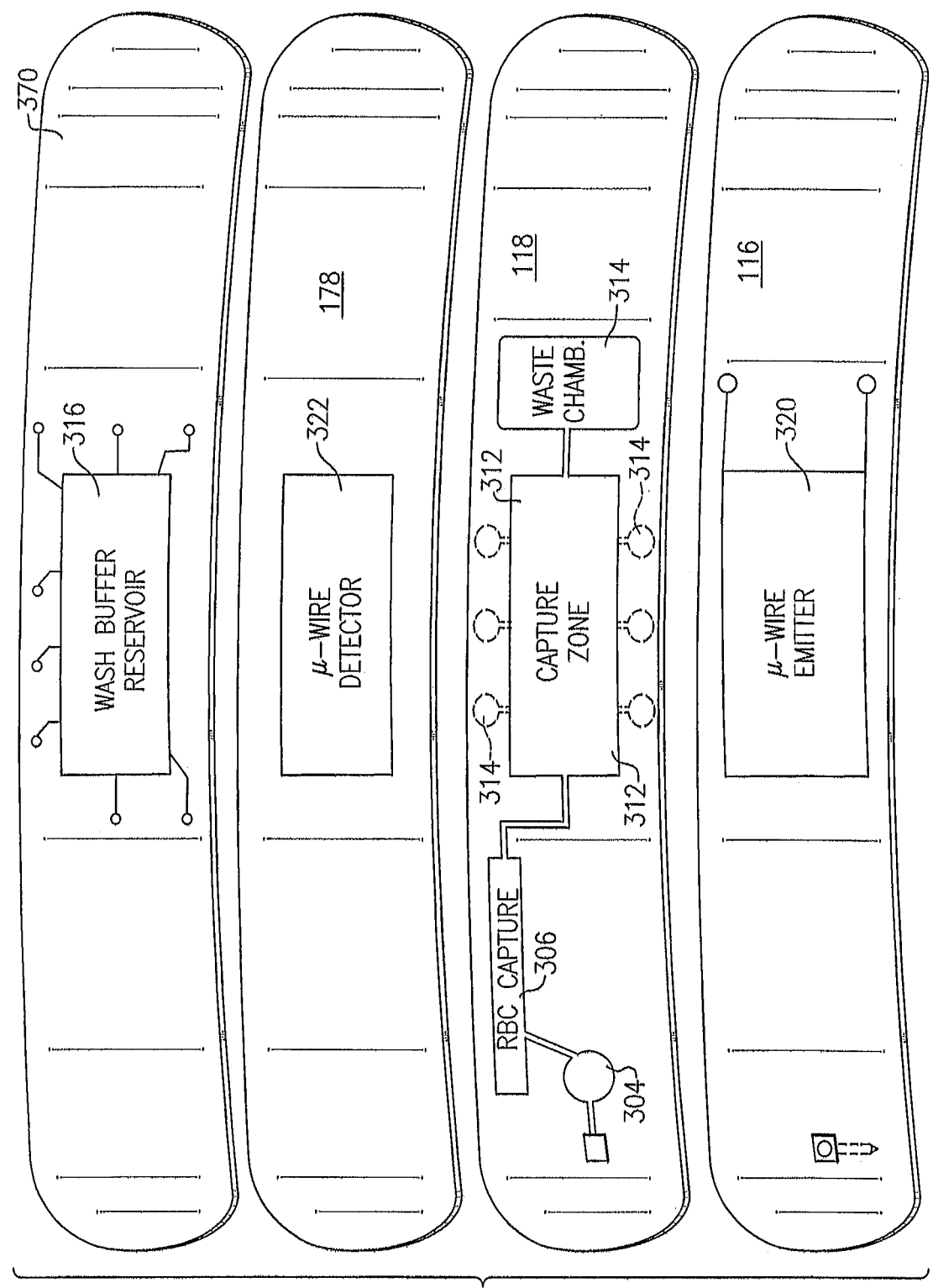
FIG. 15A is an exploded perspective view of a sample acquisition layer, fluid processing layer, results detection layer, and wash buffer reservoir layer as employed in another specific embodiment of the present personal diagnostic device implemented to perform a cellular assay.

Referring now to FIG. 15A, there is depicted an exploded perspective view of a sample acquisition layer 116, fluid processing layer 118, results detection layer 178, and wash buffer reservoir layer 370 as employed in the cellular patch embodiment of the present invention. The fluidic circuit of the cellular patch may include a sample metering chamber 304, and RBC capture chamber 306, an analysis chamber 312, a waste chamber 314, and wash buffer reservoir 316. Each of these reservoirs are operatively connected to each other and may include one or more vents 340 to prevent air blockages with the fluidic circuit as described above. The connections and flow between each chamber may be controlled by melt plugs, detent pressure valves, melt valves, and pinch valves in any desired combination of the valves described above in conjunction with FIGS. 13A-13E that allows controlled movement of the samples and buffers between the different chambers. In one particular embodiment, the capture zone 312 may be provided with several waste cambers 314 disposed around the periphery thereof to aid in the collection of waste fluids.

Figure 15B:
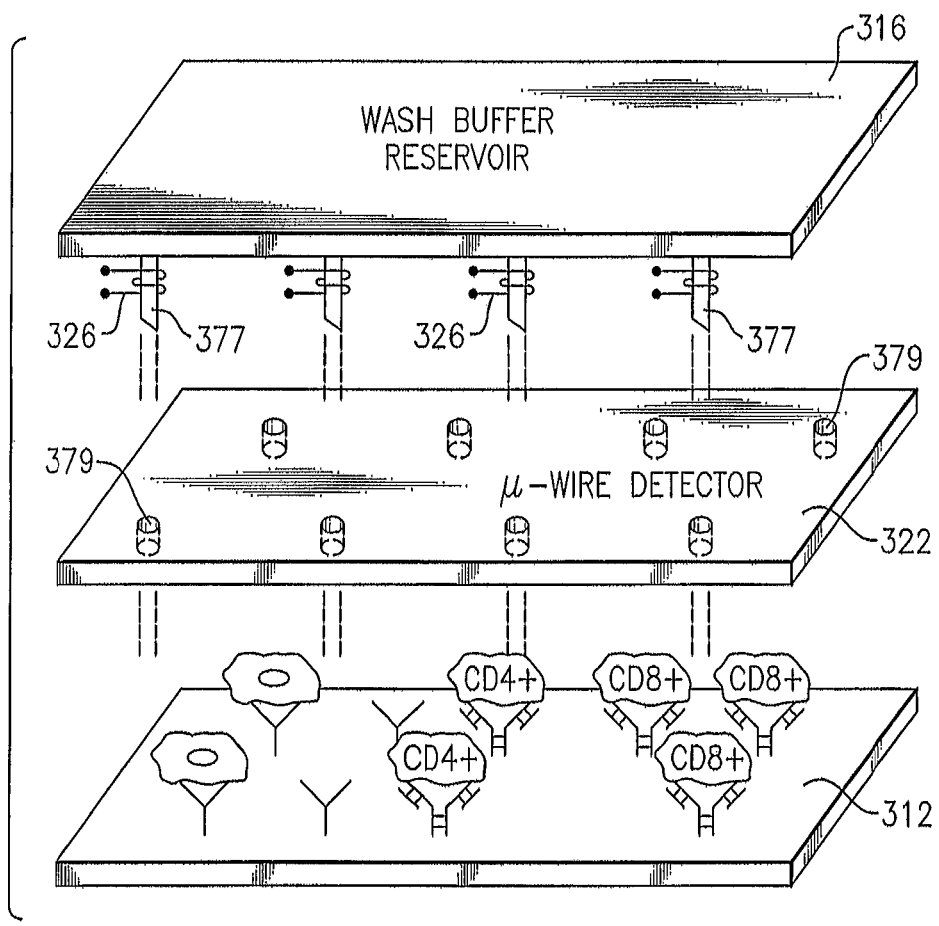
FIG. 15B is an exploded perspective isolation view of the wash buffer reservoir, micro-wire detector, and capture zone layer of the personal diagnostic device of FIG. 15A.
Figure 17A:
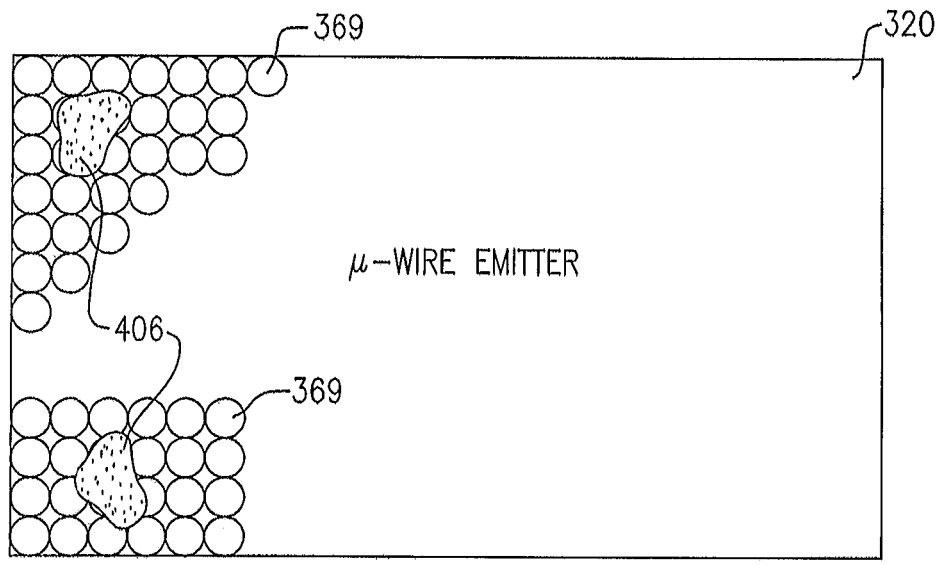
FIGS. 17A and 17B are schematic plan views of the semiconductor micro-wire assemblies employed in this invention as light emitters and detectors for illuminating, detecting, and imaging cellular assay results derived from use of the present personal diagnostic devices.
Figure 17B:
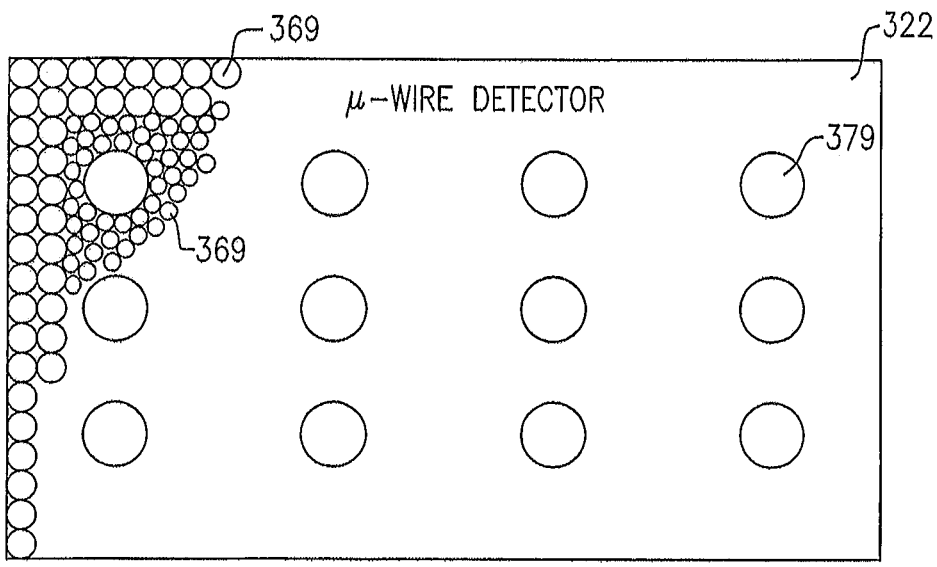

FIG. 15B is an exploded perspective isolation view of the wash buffer reservoir 316, micro-wire detector 322, and capture zone area 312. As illustrated, the wash buffer reservoir 316 is equipped with dispensing nozzles 377 with heating elements 326 that may be activated upon a specific command to open the nozzles 377 and thereby release wash buffer into the capture chamber 312. In this particular embodiment, the is provided with pass through holes so that the nozzles 377 may pass there through and direct released wash buffer directly into the capture camber 312. FIGS. 17A and 17B show in greater schematic detail the arrangement of the micro-wires 369, the pass through holes 379, and the captured cells 406 in the micro-wire emitter and detector assemblies 320 and 322 utilized according to this embodiment of the present invention. As represented in FIG. 17B, the micro-wires 369 may be of different diameters depending on the application and desired wave length.

Figure 15C:
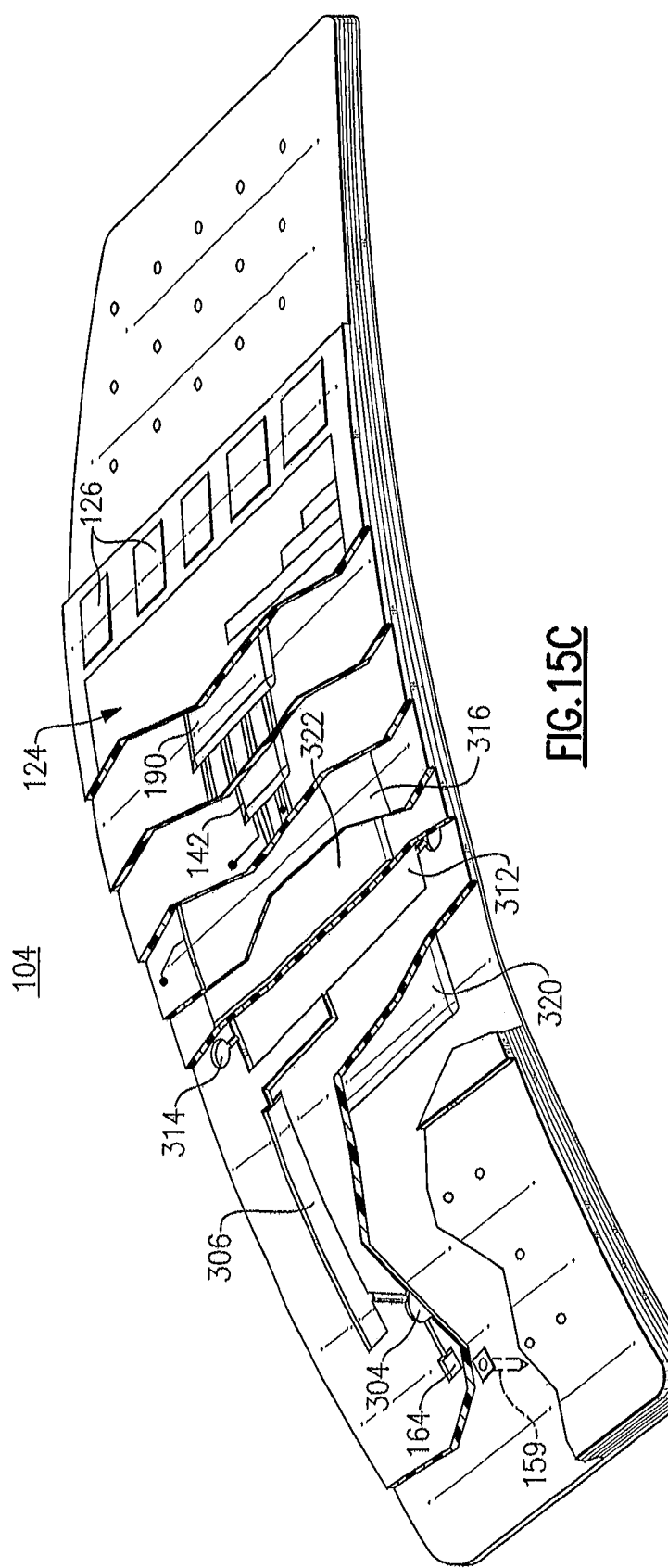
FIG. 15C is a perspective view with cut-away sections showing a fully assembled personal diagnostic device including the layers illustrated in FIG. 15A for performing a cellular assay.

FIG. 15C is a perspective view with cut-away sections showing a fully assembled personal diagnostic device including the layers illustrated in FIG. 15A for performing a cellular assay. In this view, there is thus shown the minimally invasive tubules, lancets, or micro-probes 159, reservoir openings 164, blood metering chamber 304, the RBC capture chamber 306, the micro-wire detector 320, the capture zone 312, an alternative waste chamber 314, the micro-wire detector 322, the wash buffer reservoir 316, the signal processor 142, the controller 190, the output video display monitor 124, and the individual fixed-display results windows 126.

Figure 16A:
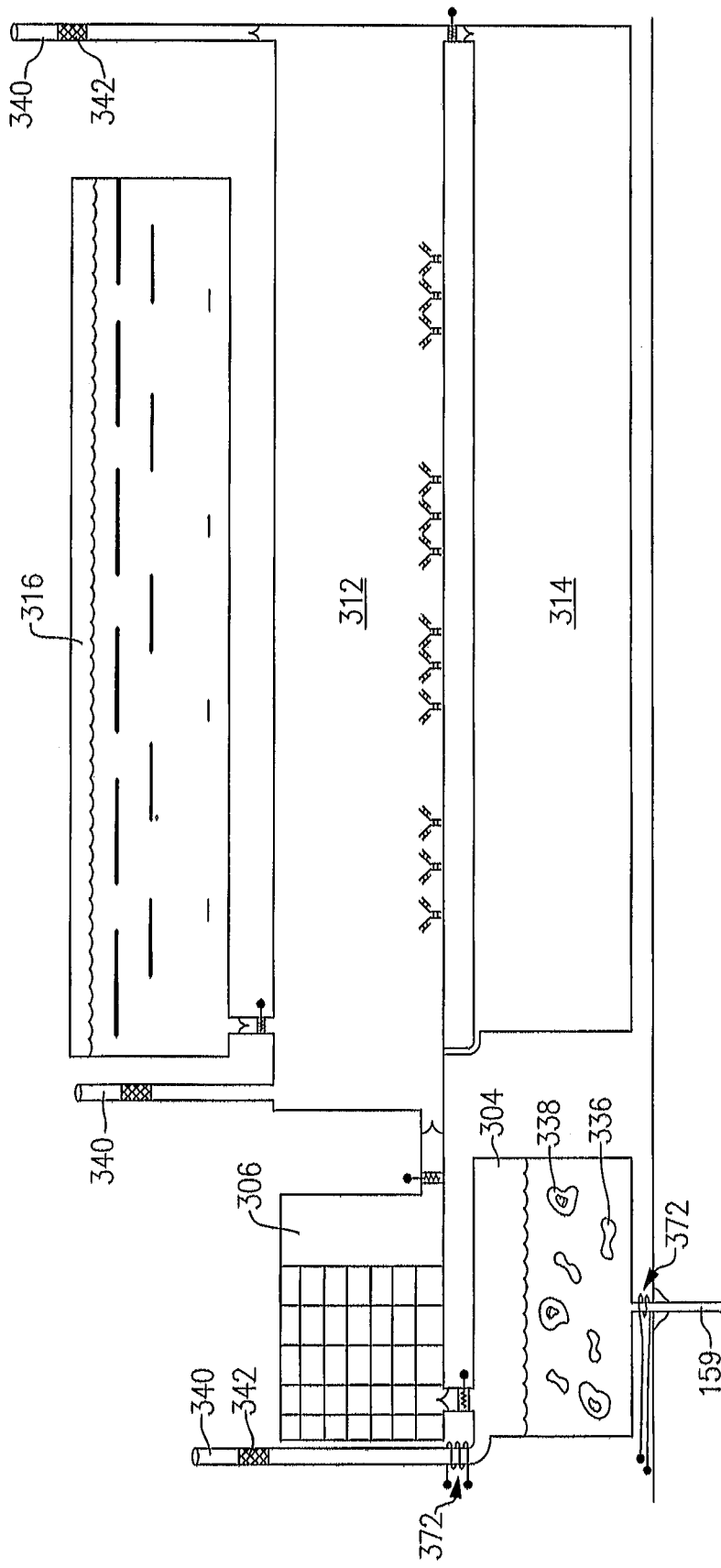
Figure 16C:
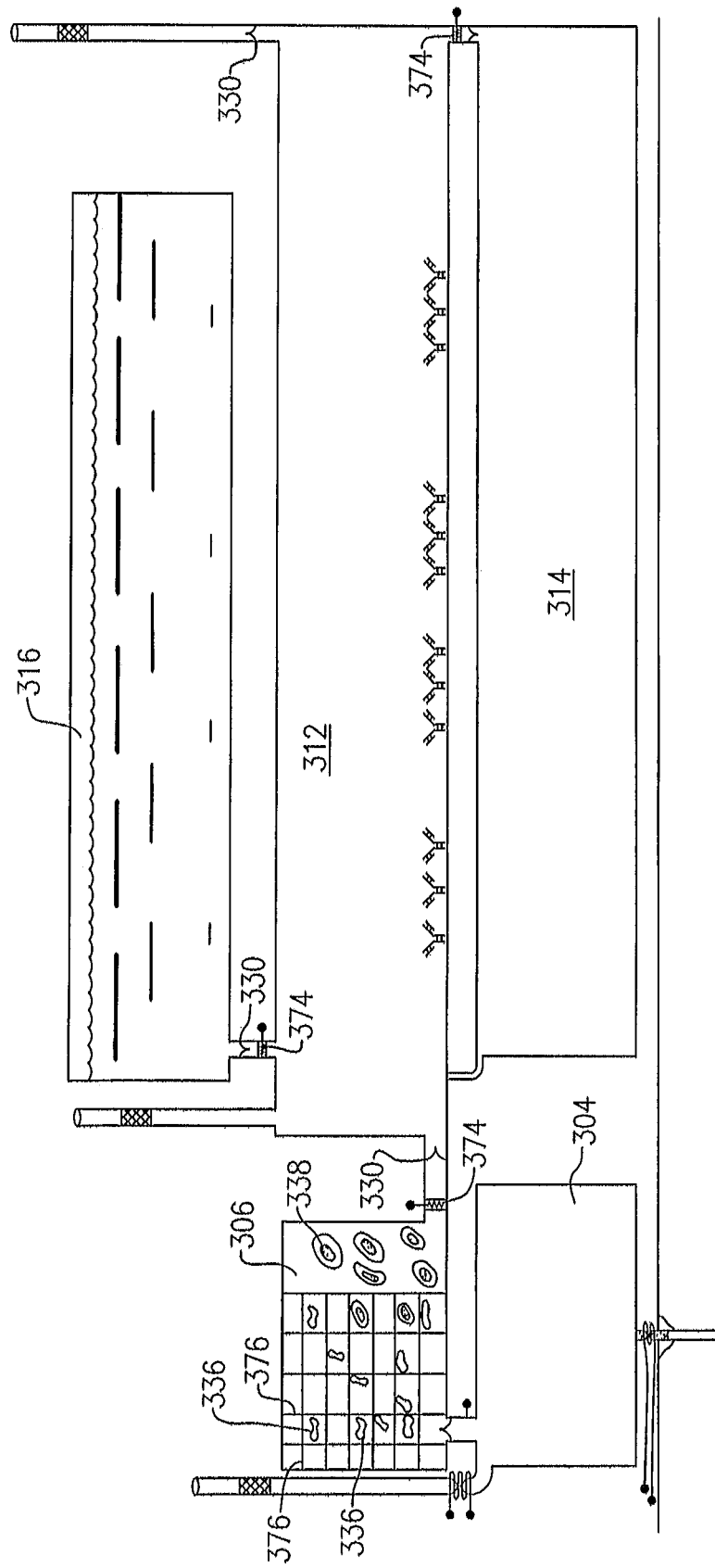

Referring next to FIGS. 16A-16F, there is shown a series cross-sectional side views of the fluidic circuit of FIG. 15 illustrating a method for detection and quantitation of CD4+ and CD8+ cells using the cellular patch. More specifically, FIG. 16A depicts acquisition of a blood sample containing RBCs and WBCs into the metering chamber 304. Blood sample is withdrawn via microprobes 159. A wide range of sample size, from 1 µl to 200 µl, to preferably about 5-10 µl can be collected. Once chamber 304 if filled to a predetermined volume, pinch valves 372 are closed (FIG. 16B). The melt plug between the metering chamber 304 and the RBC capture chamber 306 is opened (FIGS. 16B and 16C) allowing the blood sample to move into the RBC capture chamber 306 where the RBCs 336 are captured. In this illustration, a mesh that allows cells to pass through is coated with a RBC capture agent. RBCs are thus captured on the mesh as illustrated.

Separation of White Blood Cells from Red Blood Cells:

RBCs are captured onto a solid support matrix, such as a mesh or a membrane capable of lateral flow that contains a capture reagent for red blood cells. An example of membrane material which could be used is the high density or ultra high molecular weight polyethylene sheet material manufactured by Porex Technologies Corp. of Fairburn, Ga., U.S.A. This membrane has an open pore structure with a typical density, at 40% void volume, of 0.57 gm/cc and an average pore diameter of 1 to 250 micrometers, the average generally being from 3 to 100 micrometers. The optimum pore diameter for the membrane for use in this invention is about 5 to about 20 µM. The membranes are from about 0.1 mm to 5 mm in thickness. While membranes made of polyethylene have been found to be highly satisfactory, membranes made from thermoplastic materials, e.g., polyvinyl chloride, polyvinyl acetate, copolymers of vinyl acetate and vinyl chloride polyamide, polycarbonate, or polystyrene can also be used.

The RBC-binding reagent is immobilized on the solid support matrix using standard techniques well known to those skilled in the art. The reagent which is capable of binding red blood cells that is contained in the solid support matrix, such as those described above, is typically and most preferably an antibody, polyclonal or monoclonal, which is specific for red blood cells. Alternatively, other reagents which are known to bind red blood cells, such as lectins or polymeric amino acids, e.g., polylysine and polyarginine, may also be used.

Figure 16D:
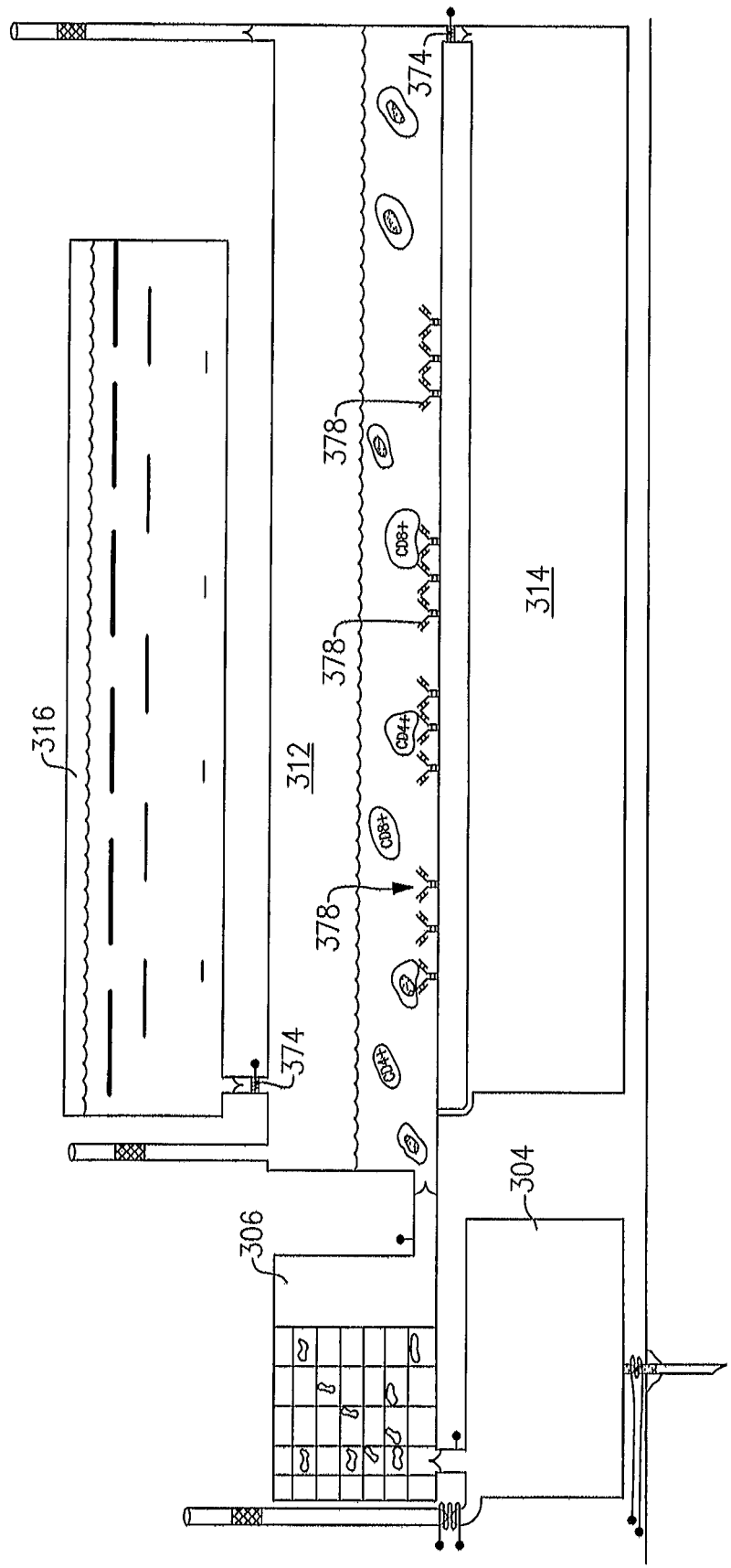

After the RBCs are removed from the sample, a melt plug 374 between the connection of chamber 306 and analysis chamber 312 is melted allowing the sample containing WBCs 338 to enter analysis chamber 312 (FIG. 16D). Chamber 312 contains immobilized capture agents against CD4+ and CD8+ cells which are preferably antibodies (as illustrated) but may include antibody fragments and other substances that specifically bind to CD4 or CD8 markers. Antibodies may be immobilized on a solid phase by a variety of methods known in the art, including covalent coupling, direct adsorption, physical entrapment and attachment to a protein-coated surface. For references describing this methodology, see Silman, I. H. and Katchalski, E. in Annual Review of Biochemistry, Vol. 35, p. 873 (1966); Melrose, G. J. H., in Review of Pure and Applied Chemistry, Vol. 21, p. 83, (1971); and Cuatrecasas, P. and Anfinsen, C. B., in Methods in Enzymology, Vol. 22, (1971). The method of attachment to a protein-coated surface is disclosed by Lai et al. (German OS No. 2,539,657; U.S. Pat. No. 4,066,512).

Specific antibodies against CD4, CD8 may be immobilized on discreet areas within the analysis chamber 312 to capture CD4+ T cells and CD8+ T cells. Positive and negative control zones may also be included within chamber 312. Cell binding in the negative control detects non specific binding. The capture antibodies can be produced in vivo or in vitro. Methods for the production of antibodies are well known to those skilled in this particular art. For example, see Antibody Production: Essential Techniques, Peter Delves (Ed.), John Wiley & Son Ltd, ISBN: 0471970107 (1997). Alternatively, antibodies may be obtained from commercial sources, e.g., Research Diagnostics Inc., Pleasant Hill Road, Flanders, N.J. 07836 and Ortho Diagnostic Systems).

Figure 16E:
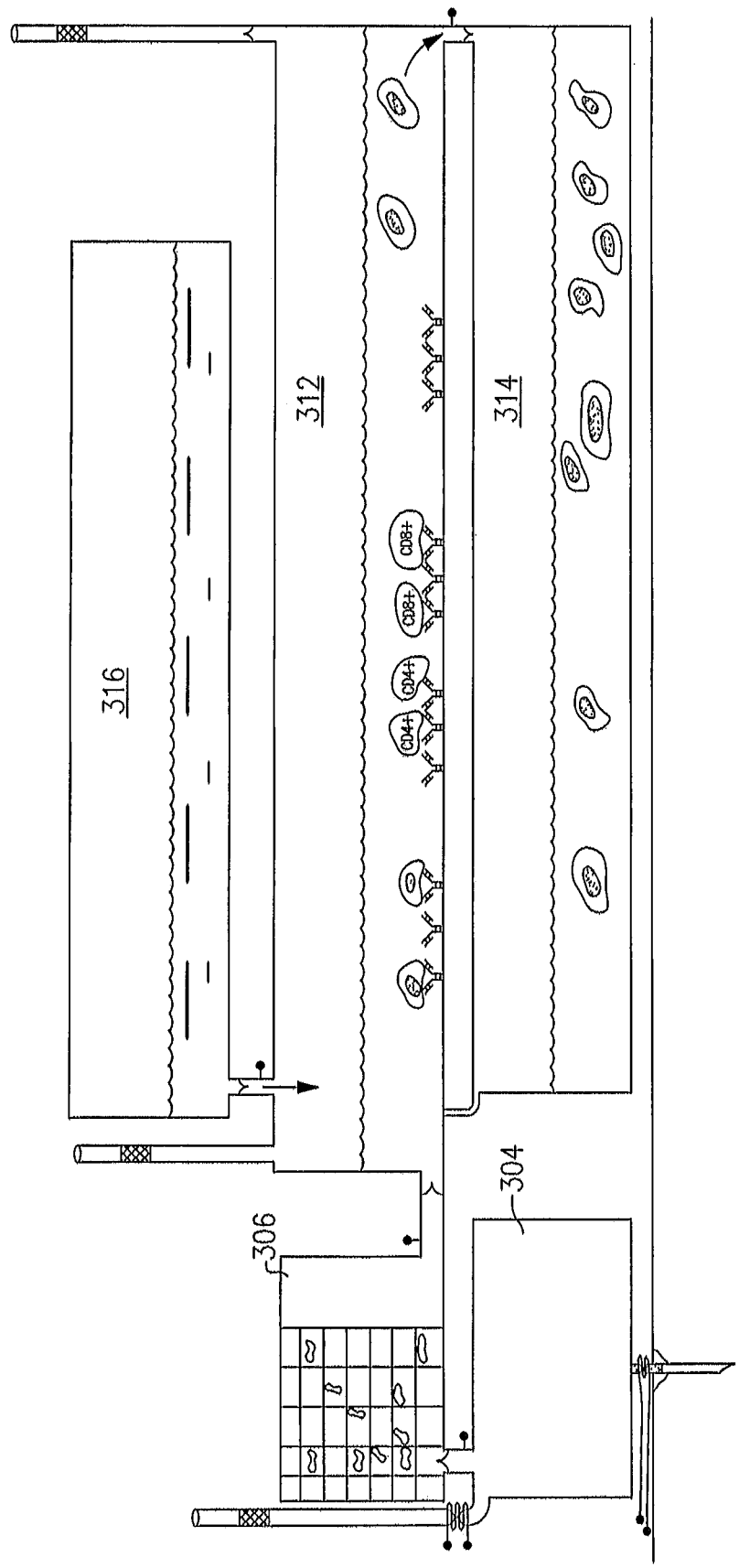
Figure 16F:
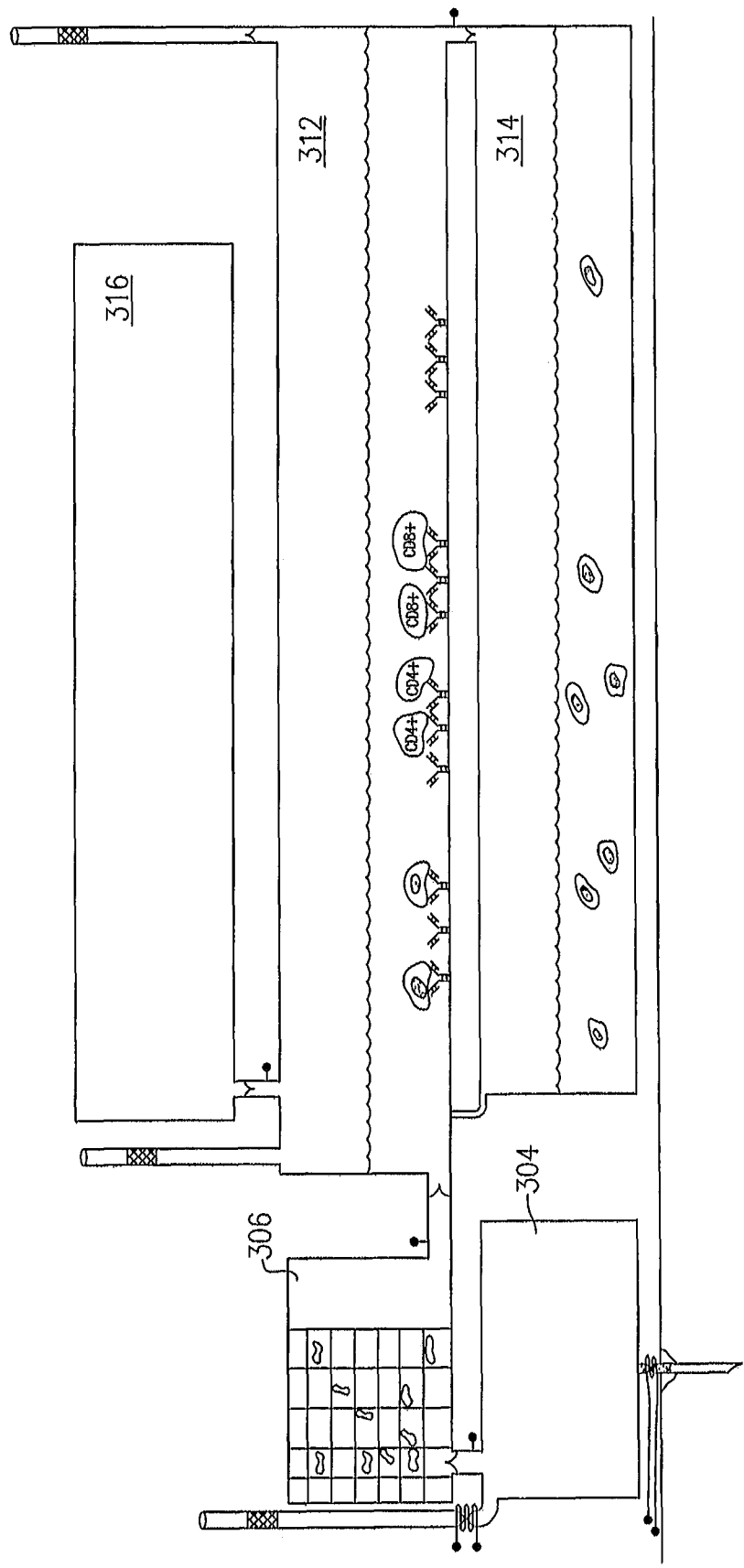

After allowing sufficient time for cells to bind with their respective capture agents, the analysis chamber 312 is then washed to remove unbound cells. Washing is performed by flushing chamber 312 with a wash buffer. As depicted in FIGS. 16D and 16E, melt plugs 274 between reservoir 316, capture chamber 312, and waste chamber 314 are opened and wash buffer from reservoir 316 is moved into chamber 312 which carries unbound cells into waste chamber 314. The wash process can be initiated by a time-controlled opening of the melt plug connecting the reservoir 316 to chamber 312, as well as the melt plugs connecting chamber 312 to the waste chamber 314.

Once the unbound cells are removed (FIG. 16F), the number of CD4+ and CD8+ cells captured can be quantified by image analysis. The program algorithm counts the number of cells in the CD4+ and CD8+ capture zone, calculates the ratio of CD4+/CD8+ and the absolute counts using the volume of whole blood metered prior to red blood cell capture.

Small Molecule Assay Implementations and Methods

The quantification of chemical and biochemical components in colored aqueous fluids, in particular colored biological fluids such as whole blood and urine and biological fluid derivatives such as blood serum and blood plasma, is of ever-increasing importance. Important applications exist in medical diagnosis and treatment and in the quantification of exposure to therapeutic drugs, intoxicants, hazardous chemicals, and the like. In some instances, the amounts of materials being determined are either so miniscule (in the range of a microgram or less per deciliter) or so difficult to precisely determine that the apparatus employed is complicated and useful only to skilled laboratory personnel. In this case the results are generally not available for some hours or days after sampling. In other instances, there is often an emphasis on the ability of lay operators to perform the test routinely, quickly and reproducibly outside a laboratory setting with rapid or immediate information display.

One common medical test is the measurement of blood glucose levels by diabetics. Diabetes is a major health concern, and treatment of the more severe form of the condition, Type I (insulin-dependent) diabetes, requires one or more insulin injections per day. Insulin controls utilization of glucose or sugar in the blood and prevents hyperglycemia which, if left uncorrected, can lead to ketosis. On the other hand, improper administration of insulin therapy can result in hypoglycemic episodes, which can cause coma and death. Hyperglycemia in diabetics has been correlated with several long-term effects of diabetes, such as heart disease, atherosclerosis, blindness, stroke, hypertension, and kidney failure.

Current teaching counsels diabetic patients to measure their blood glucose level from two to seven times a day depending on the nature and severity of their individual cases. Based on the observed pattern in the measured glucose levels, the patient and physician together make adjustments in diet, exercise and insulin intake to better manage the disease. Clearly, this information should be available to the patient immediately.

Conventional blood glucose monitoring methods generally require the drawing of a blood sample (e.g., by finger prick) for each test, and a determination of the glucose level using an instrument that reads glucose concentrations by electrochemical or colorimetric methods. Type I diabetics must obtain several finger prick blood glucose measurements each day in order to maintain tight glycemic control. However, the discomfort and inconvenience associated with this method of measurement, along with the fear of hypoglycemia, has lead to poor patient compliance, despite strong evidence that tight control dramatically reduces long-term diabetic complications. Accordingly, there remains a need in the art for medical devices which provide effortless analyte measurements in field or home-testing applications, particularly where continual and/or automatic monitoring is desired.

Figure 18A:
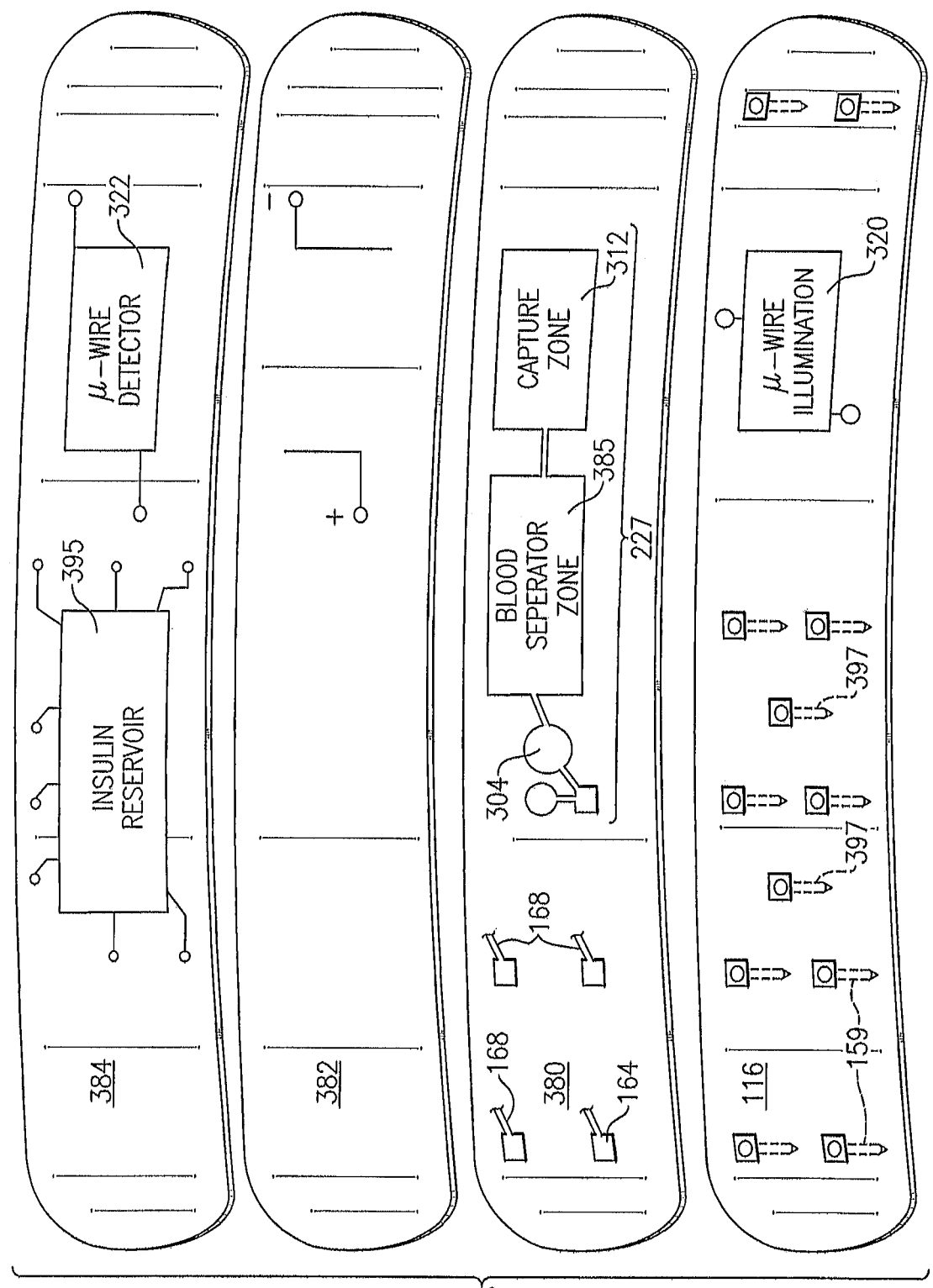
FIG. 18A is an exploded perspective view of a sample acquisition layer, fluid processing layer, and alternative results detection layers as employed in yet another specific embodiment of the present personal diagnostic device implemented to perform small molecule assays.
Figure 18B:
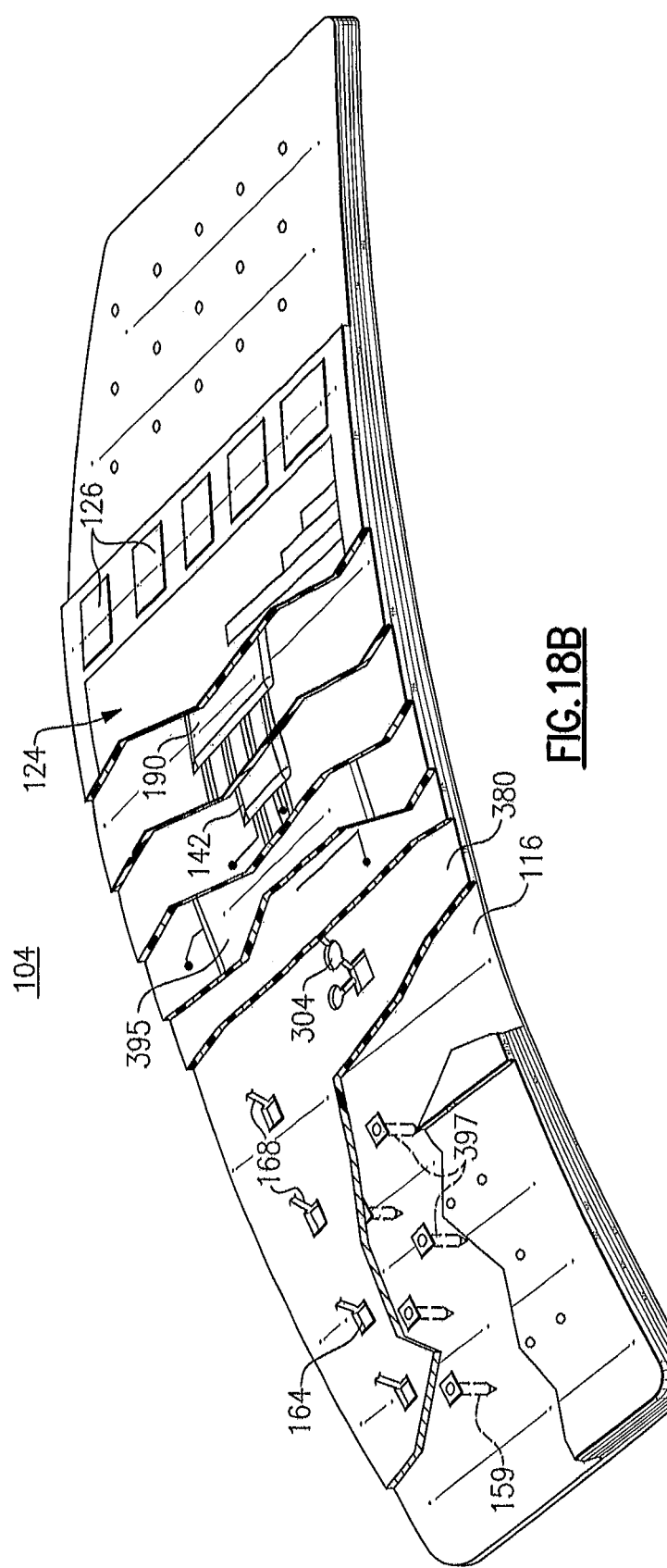
FIG. 18B is a perspective view with cut-away sections illustrating a fully assembled personal diagnostic device including the layers shown in FIG. 18A for performing a small molecule assay.

Now with reference to FIGS. 18A and 18B, there is shown exploded and cutaway views of the personal diagnostic device 104 of the present invention for detection of small molecules herein referred to as the small molecules patch. This bio-patch provides a quick, effortless, and automatic device and method for analyte quantification using only a simple patch or bracelet that interfaces with a personal computer. The small molecules patch may include a sample acquisition layer 116, a sample processing layer 380, and an electrochemical detector layer 382 or alternatively, (or in combination therewith), a photo detector layer 384. Sample processing is carried out in a biocompatible lateral flow matrix preloaded with analysis reagents as described in further detail blow with reference to FIGS. 19A and 19B.

The sample processing layer 380 includes a particular micro-fluidic circuit 227 with individual fluid components that will be described in detail below. The sample processing layer 380 may include one micro-fluidic circuit 227 or may alternatively include several micro-fluidic circuits 227 formed therein as represented in broken-line fashion by the four referenced reservoir openings 164 and their respective first fluid channels 168. Alternatively, the device 104 may include several sample processing layers 380 each with a single or a multiple number of micro-fluidic circuits 227. In this manner, several blood samples may be taken over time by using flow control at the first fluid channel 168 as described with reference to FIGS. 13A to 13E. Each of these separate blood samples may then be processed in real time in a separate micro-fluidic circuit 227. For example, the device 104 may include 12 micro-fluidic circuits 227 either all formed and situated on one sample processing layer 380, or each formed and situated on separate individual sample processing layers 380 for a total for 12 such sample processing layers. As understood, the 12 circuits would be preferably fluidly isolated from each other. Alternatively, the 12 micro-fluidic circuits 227 may be formed and situated in pairs, groups of three, or groups of four, for example, with each pair or group then being formed on one such layer 380. The various layers are then assembled accordingly to function as intended. In this specific embodiment, each of the 12 micro-fluidic circuits 227 would be fluidly connected to a respective lancet 159 as discussed above. With blood sampling and fluid control directed and timed by the controller 142, a melt plug associated with each lancet 159 may be activated at a specific time to put a respective metering chamber 304 in fluid communication with its respective lancet 159 to thereby draw a fresh sample of blood by capillary action at a specific predetermined time. With 12 circuits 227 and 12 corresponding lancets 159, for example, a user may wear the bio-patch device 104 for a twenty-four hour period with a blood sample taken every two hours.

The micro-fluidic circuit 227 includes the blood metering chamber 304, a separate blood separator zone 385 and a capture zone 312. In some implementations of this embodiment, the separate blood separator zone 385 and the capture zone 312 may be combined into a single zone or chamber with serial processing of the sample fluid through a biocompatible lateral flow matrix or membrane which may be comprised of separate pads or segments, or alternatively comprised of a single lateral flow matrix provided with various gradations for different fluid processing results along the length thereof. In FIGS. 19A and 19B, the blood separator zone 385 and the capture zone 312 are combined into a single membrane or matrix 386 including three lateral flow pads.

Figure 18C:
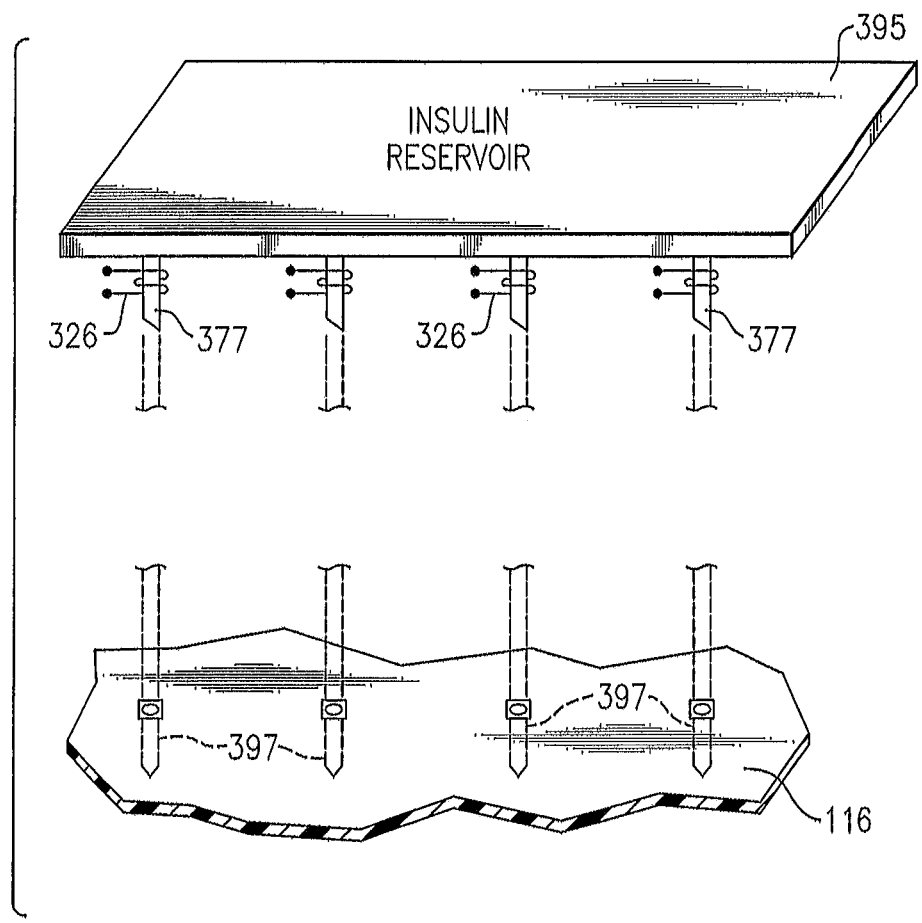
FIG. 18C is an exploded perspective isolation view of the insulin reservoir and related supply lancets of the personal diagnostic device of FIGS. 18A and 18B.

In the glucose assay implementation hereof, the bio-patch or bio-bracelet may advantageously include a pre-loaded supply reservoir of insulin 395, FIGS. 18A and 18C. Here software stored in the logic controller 190 or signal processor 142 is interactive to direct a control system to release a determined dose of insulin. To release the insulin, a supply duct may be provided with a one-way valve of the flexible detent lip type described above. Also a plug will be used to hold the insulin in the supply reservoir. This plug is not dissolvable upon contact with liquid because it needs to hold the insulin in the supply reservoir until directed by the control system to release the dosage in the reservoir. Here we use an electric signal generated by the control system to send a current to the plug which is pre-wired with a resistive element and designed to melt when current is supplied to the resistive element embedded in the plastic type plug material. In this manner, the insulin form the supply is released in a controlled, timed fashion. Metering the release flow and closing the channel or supply duct may also be achieved. The dosage is preferably controlled by the size of the supply reservoir wherein a simple discharge of the entire volume from the reservoir is initiated when needed. The reservoirs can be of different volumes and the desired volume selected by the control system by sending the melt current to the reservoir with the correct volume.

With continuing reference to FIG. 18A, the photo detector layer 384 includes the insulin reservoir 395 which may be pre-loaded with a predetermined amount of insulin according to the time-release aspects of this invention. The insulin reservoir 395 may have one pre-loaded reservoir or alternatively it may be subdivided into several smaller reservoirs each having a pre-determined amount of insulin stored therein for time-release application. According to this aspect of the present invention, a prescribed dosage of insulin, for example, is released from the insulin reservoir 395, directed to a respective supply lancet, tubule, or micro-probe 397 through suitable fluid circuits, and then thereby caused to enter the blood stream of the user. FIG. 18C shows in greater schematic detail this aspect of the present invention. As shown, the insulin reservoir 395 is provided with the dispensing nozzles 377 that are opened by a command from the controller 142 by use of the heating elements 326 as described above in regard to FIG. 15B. Through suitable supply fluid circuits, a pre-determined dose of insulin is thereby administered to the user of the device. The logic controller 190 may include expert software that determines the insulin needs of the patient and then administers a proper dosage of insulin as based on the detected results of the glucose assay. As would be readily apparent to one of skill in these arts, the device so described herein is not specifically limited to conducting glucose tests and administering a determined amount of insulin as based on those tests, but may be readily applied and adapted to a wide verity of different assays and hormone or drug release therapies or treatments.

FIG. 18B is a perspective view with cut-away sections showing a fully assembled personal diagnostic device 104 including the layers illustrated in FIG. 18A for performing a small molecule assay. In this view, there is thus shown the minimally invasive tubules, lancets, or micro-probes 159, the reservoir openings 164, the blood metering chamber 304, the insulin reservoir 395, the supply lancets 397, the signal processor 142, the controller 190, the output video display monitor 124, and the individual fixed-display results windows 126.

Referring now to FIG. 19A, there is illustrated a cross-sectional side view showing the blood metering chamber 304 and the biocompatible lateral flow matrix or membrane 386 which is divided into three sections including a cell separation pad 388, a reaction pad 390, and an adsorbent pad 392. Blood sample is withdrawn via the microprobe 159 at specified time intervals throughout the life time of the small molecules patch. There may be multiple collection sites and/or multiple inlet ducts as described above. Also as described above, there may be several microprobes to extract blood into the micro-fluidic circuit in the patch. For purposes of clear explanation here in regard to FIGS. 19A and 19B, the present assay will be described with reference to one such fluid circuit.

Preferably about 5-10 µl of blood is withdrawn at specified time intervals. The microprobes 159 are preferably coated with anticoagulant to prevent blood clotting. The micro-fluidic circuit may include a reservoir with programmable valves to flush out any old blood accumulated at the tip of the microprobes as described in further detail below in conjunction with FIGS. 20A and 20B. With continuing reference to FIG. 19A, blood enters the metering chamber 304 which is closed when the amount of blood reaches a desired or pre-determined level. The circuit may be closed using the pinch valve 372. The metered blood is then allowed to enter the cell separation pad 388 by opening melt plug 374.

For electrochemical detection method, glucose can be measured directly from whole blood in the metering reservoir 304 where appropriate electrodes, shown schematically in layer 382 of FIG. 18A, are placed in contact with the blood sample to measure glucose levels. In this case, glucose oxidase is preloaded into the metering chamber 304 which produces hydrogen peroxide ($H_2O_2$) in the presence of glucose which is detectable electrochemically.

However, should optical detection (absorbance, reflectance, or transmittance, for example) be the method of choice for the detection of results, a cell separation step can be included as shown. In this embodiment, the cell separation pad 388 separates RBC and WBC from the plasma or serum. In a typical operation, a 5-10 µl blood sample is collected and directed into the cell separation pad 388. As the sample migrates through pad 388, the fibrous network material making up pad 388 retards the movement of particulate matter, including blood cells, acting to partially remove blood cells before the sample reaches the reaction pad 390, FIGS. 19A and 19B.

All enzymes necessary for the glucose reaction are immobilized or preloaded in the reaction pad 390. For the glucose assay, the reaction pad(s) contains glucose oxidase, a peroxidase, and a substrate reagent which is converted by the peroxidase in the presence of $H_2O_2$ to a detectable reaction product 391 as illustrated in FIG. 19B. This reaction is presented below. Preferably, the reaction pads are porous, fused polymer substrate membranes having a thickness (after complete penetration of the fluid) of about 125 µm and side dimensions of about 1 mm. The absorption volume of each pad is preferably between about 1 and 2 µl.

Glucose Assay:

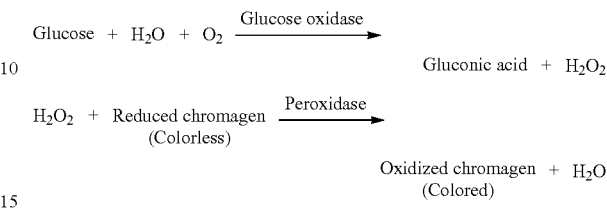

When the method of detection is optical, the micro-wire emitter 320 is activated to emit incident illumination 373 toward the detectable reaction product 391 as shown in FIG. 19B. After light/matter interaction between the incident energy 373 and the detectable reaction product 391, modified electro-magnetic energy is transmitted toward the micro-wire detector 322. Optical and/or image analysis is then performed to quantify the results as described above. In the alternate embodiment hereof where the method of detection is electrochemical, the enzyme peroxidase and chromagen substrate are omitted. In this case, the $H_2O_2$ produced is oxidized at a platinum electrode to produce an electric current which is proportional to the sample glucose concentration.

The amount of hydrogen peroxide produced is quantified either by absorbance (via a chromagen that changes color upon being oxidized as depicted in FIG. 19B or by the change in electrochemical force via the electrodes, for example, as alternatively illustrated in FIG. 18A. The small molecule patch may have an algorithm installed in the logic controller 190 that will result in a beep or beeping type sound should the analyte concentration drop below a prescribed threshold or become higher than a certain level so that the patient can take appropriate action.

The device hereof may be readily adopted for use in conjunction with other small molecules such as cholesterol, low density lipoproteins or high density lipoproteins, triglycerides, and others. For example, in an assay for total serum cholesterol, the reaction pad(s) will contain cholesterol esterase, cholesterol oxidase, a peroxidase, and a substrate reagent which is converted by the peroxidase in the presence of $H_2O_2$ to the detectable reaction product 391. If the method of detection is electrochemical, the enzyme peroxidase and chromagen substrate are omitted as discussed above.

As another example, the small molecule patch may be used in determining triglycerides in a blood-fluid sample, in this case the reaction pad will contain lipase, a source of ATP, glycerol kinase, and glycerol-phosphate oxidase, for generating $H_2O_2$, and the above components for generating the detectable reaction product 391 in the presence of $H_2O_2$.

Stress Monitoring Implementations and Methods

In daily life, individuals encounter many sources of stress. The detrimental effects of stress on general health are well documented. Health problems such as heart disease, depression, lack of energy, insomnia, and hypertension have all be related to stress. Thus the inventors hereof propose a personal diagnostic device that records a user's stress level throughout the day. At the end of the day, the user downloads the day's collection of analytical stress information to see at what time of the day the user encountered the highest stress levels.

In this implementation, a user of the personal stress monitoring device would keep a written or voice recorded journal of the day's activities. For example, simple entries such as "wake up, 6:45 am"; "fix breakfast, 7:30 am"; "drive kids to school, 8:00"; "meeting with boss, 9:45 am"; "argue with co-worker, 10:30 am"; "lunch, noon to 1:30 µm"; "afternoon coffee, 3:15 µm"; "pick kids up from day care, 5:15 µm"; "work out at gym, 5:00 to 7:00 µm"; "fix dinner, 7:30 µm"; "put kids to sleep, 9:00 µm"; "fight with spouse, 9:30 µm"; "do family finances, 10:00 to 11:15 µm"; "watch late night television, 11:30 µm"; and "go to sleep, 12:15 am" would be maintained on a daily basis while under the care of a medical doctor or other health care professional.

In this manner, a patient and the patient's doctor could determine patterns of daily living that cause the highest stress levels. With counseling and professional intervention, the patient's life style could be revised or adjusted to avoid the daily activities which cause unhealthy levels of stress. If stress levels are abnormally high when interacting with a spouse, for example, marriage counseling may be recommended. If stress levels are particularly high with a certain co-worker or the boss, then the employee's company may be liable for exposure to a hostile environment and then be required to take remedial action.

Many individuals now have private personal physicians who are available 24 hours a day by phone and email. The stress patch described below may be further provided with a fluid release reservoir that is pre-loaded with some type of prescription drug such as the insulin reservoir 395 described above with reference to FIGS. 18A to 18C. According to one method of use of the present invention, if the user of the stress patch desires medication, the user goes to his desk top computer as illustrated in FIG. 1 and clicks on the Life Patch icon. The PC and related software then download the day's collection of stress data stored in the PDD 104 via the RF receiver 114. The stress data is then relayed to the private personal physician who then determines that a dosage of the drug is needed by the patient. The doctor then inputs a command to his computer that is transmitted to the patient's computer. The patient's computer in turn sends a command to the user's patch to release a pre-loaded dosage of prescription medication. In this manner, over medication of dangerous or addictive drugs is avoided.

According to another method of use of the present invention, the above method is modified to remotely control use and dosage of experimental drugs during clinical trials. The use and dosage is thus doctor-controlled remotely by patch interaction, after the doctor analyzes downloaded bio-feedback information. Also, the doctor may monitor remotely the patient's biological and physiological response to the released drug via real-time patch/PC interaction.

In a similar manner, the inventors hereof propose that implementations of the present invention may be used to monitor and treat various psychiatric disorders such as depression, for example. In this use application, the bio-patch monitors in real time a patient's mental health and reports to the attending physician or psychiatrist when mental health is outside of normal parameters. In this case, the bio-patch or bio-bracelet then reports remotely to the attending physician or psychiatrist who in turn may remotely authorize the patch to release a dosage of anti-depression drugs. This use method according to the present invention may also be advantageously applied to other mental disorders, such as schizophrenia or paranoia, which are treated with strong drugs. Similarly, the doctor controlled drug release aspects of the present invention may be employed to wean drug addicts off of cocaine or heroin. In an alternate implementation of this embodiment, user/PC interaction is not required. Alternatively, the home or hospital environment to which a patient may be confined is equipped with remote RF receivers. The personal diagnostic device according to this aspect of the invention is then implemented to transmit a continuous or intermittent signal. As the device transmits this reporting signal, collected diagnostic information is thereby wirelessly communicated to the attending physician without the need of any user/PC interaction.

Returning now to the stress patch implementation of the present invention, it is understood by artisans in the field that the hormone cortisol is produced by the adrenal gland and is released in the body during stressed or agitated states. Thus cortisol has gained widespread attention as the so-called "stress hormone." This hormone, however, is more than a simple marker of stress levels, it is necessary for the functioning of almost every part of the body. Excesses or deficiencies of this crucial hormone also lead to various physical symptoms and disease states. Cortisol has been studied as a biomarker for many diseases such as Cushing's disease, chronic fatigue syndrome, and fibromyalgia—an autoimmune disorder. Cortisol has also been correlated with stress levels. It has been found that the level of salivary cortisol serves as a biochemical marker for post-traumatic psychological distress disorders and other conduct disorders. Thus, measurement of cortisol levels in the body can be an important diagnostic tool—both in clinical settings and during certain stress-intensive activities. Cortisol levels in the body, however, fluctuate throughout the day with levels being highest in the morning and lowest in the evening. Dietary intake and metabolic imbalances cause further fluctuations. To identify and allow for these different fluctuations, a real-time determination of cortisol levels is needed, without the use of costly and cumbersome laboratory equipment. Because the clinically significant concentration range of cortisol is very small (e.g. about 12.5 to 800 ng/ml), cortisol concentrations are commonly determined via immunoassay techniques.

For many cortisol detection applications, the development of portable, semi-invasive sensor devices, which are relatively highly-selective and sensitive to the detection of cortisol, and are capable of continuous monitoring cortisol levels in real-time, is of particular interest.

In view of the above, the inventors hereof propose a personal diagnostic device for monitoring stress markers or indicators such as cortisol. This specific PDD is herein referred to as a stress patch and as implemented provides a quick, effortless, and automatic device and method for cortisol quantification using only a simple patch or bracelet that can interface with a personal computer or RF wired computer network.

Figure 20A:
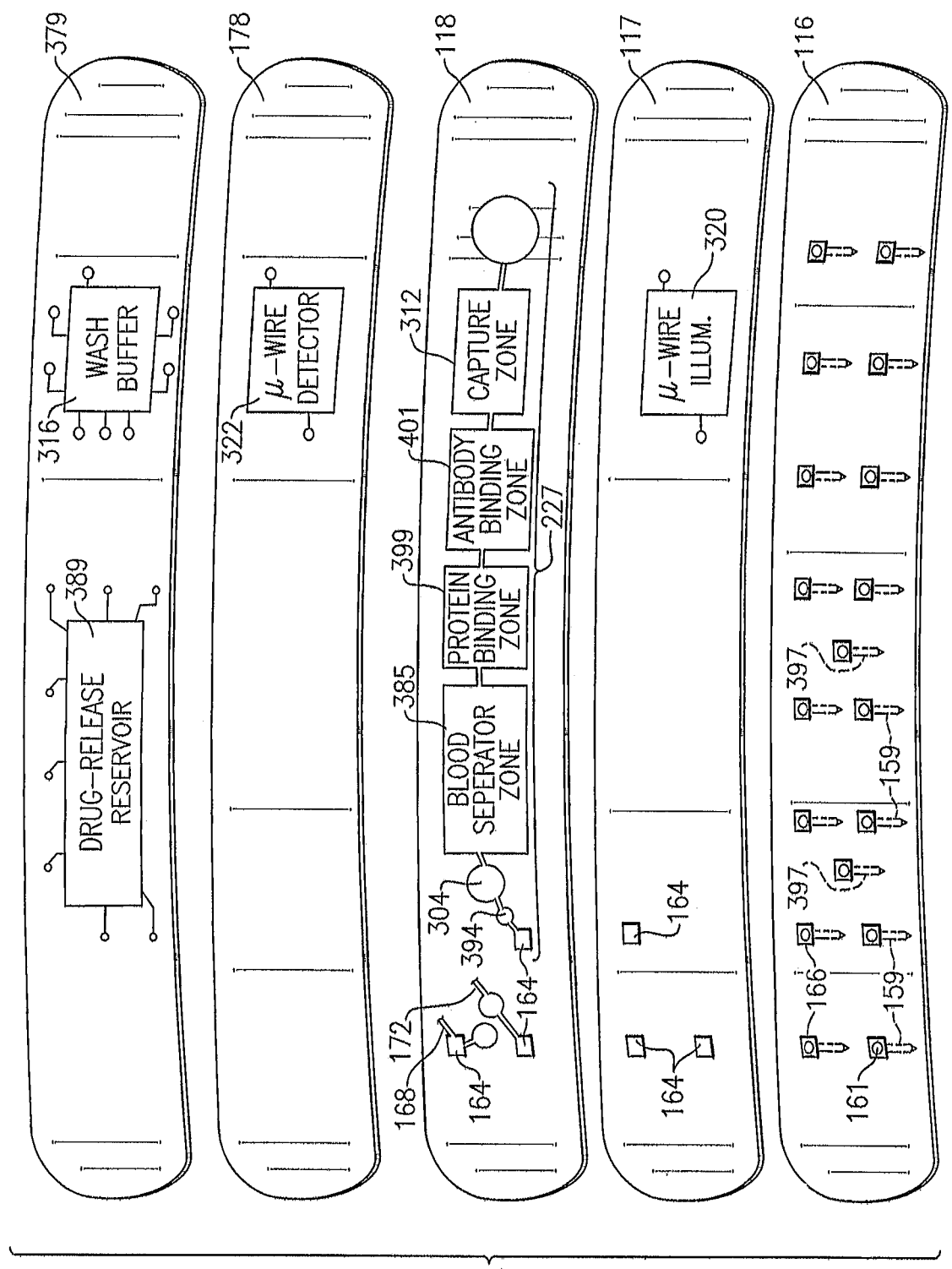
FIG. 20A is an exploded perspective view of a sample acquisition layer, results illumination layer, fluid processing layer, results detection layer, and wash buffer reservoir layer as employed in still another alternative specific embodiment of the present personal diagnostic device implemented to perform stress analysis.

Turning now to FIG. 20A, there is shown an exploded perspective view of the principal fluid sample processing layers of a stress patch according to another preferred embodiment of the present invention. These include the sample acquisition layer 116, a separate results illumination layer 117 as used in this particular embodiment, the fluid processing layer 118, the results detection layer 178, and reservoir layer 379 as utilized to perform stress monitoring. As illustrated, the sample acquisition layer 116 includes the minimally invasive tubules, lancets, or micro-probes 159 that penetrate the skin surface to thereby acquire blood samples from capillaries near the epidermis. In this particular embodiment of the personal diagnostic device, the micro-wire emitter 320 is employed as the light source for illuminating the assay results and herein is preferably provided in the separate results illumination layer 117. Alternatively, the micro-wire emitter 320 employed herein may be preferably integrated with the sample acquisition layer 116 as in the embodiments discussed above. The results illumination layer 117 is provided with the reservoir openings 164 with are respectively positioned in register with the inlet formations 166 formed around the discharge end 161 of the lancet or micro-probe 159. In this manner, the blood sample is allowed to pass through the results illumination layer 117 and enter the corresponding reservoir opening 164 in the fluid processing layer 118. The reservoir layer 379 includes and optional wash buffer 316 which is of the type described with reference to FIGS. 15A and 15B, and a drug-release reservoir 389. The results detection layer 178 is provided with the micro-wire detector 322 with is of the type described in detail in conjunction with FIGS. 14A-14K and as employed in the device embodiments shown in FIGS. 15A and 18A.

With continuing reference to FIG. 20A, the fluid processing layer 118 includes the micro-fluidic circuit 227. This particular embodiment of the micro-fluidic circuit 227 is provided with the reservoir opening 164, a draw-off reservoir or an initial sample collection chamber 394, the blood metering chamber 304, the blood separator zone 385, a protein binding zone 399, an antibody binding zone 401, and the capture zone 312.

The sample processing layer 118 may include one micro-fluidic circuit 227 or may alternatively preferably include several micro-fluidic circuits 227 formed therein as represented by the two referenced reservoir openings 164 and their respective fluid channels 168. Alternatively, the device 104 may include several sample processing layers 118 each with a single or a multiple number of micro-fluidic circuits 227. In this manner, several blood samples may be taken over time by using flow control at the first fluid channel 168 as described with reference to FIGS. 13A to 13E. Each of these separate blood samples may then be processed in real time in a separate micro-fluidic circuit 227. For example, the device 104 may include 24 micro-fluidic circuits 227 either all formed and situated on one sample processing layer 118, or each formed and situated on separate individual sample processing layers 118 for a total for 24 such sample processing layers. As understood, the 24 circuits would be preferably fluidly isolated from each other. Alternatively, the 24 micro-fluidic circuits 227 may be formed and situated in pairs, groups of three, or groups of four, for example, with each pair or group then being formed on one such layer 118. The various layers are then assembled accordingly to function as intended. In this particular embodiment of the stress patch, each of the 24 micro-fluidic circuits 227 would be fluidly connected to a respective lancet or micro-probe 159 as discussed above. With blood sampling and fluid control directed and timed by the controller 142, a melt plug associated with each lancet 159 may be activated at a specific time to put a respective initial sample collection chamber 394 in fluid communication with its respective lancet 159 to thereby draw a fresh sample of blood by capillary action at a pre-determined specific time. With 24 circuits 227 and 24 corresponding lancets 159, for example, a user may wear the bio-patch device 104 for a twenty-four hour period with a blood sample taken every hour.

The micro-fluidic circuit 227 illustrated in FIG. 20A includes the reservoir opening 164, the draw-off reservoir or initial sample collection chamber 394, the blood metering chamber 304, the blood separator zone 385, the protein binding zone 399, the antibody binding zone 401, and the capture zone 312. In some implementations of this embodiment, the blood separator zone 385, the protein binding zone 399, the antibody binding zone 401, and the capture zone 312 may be combined into a single zone or chamber with serial processing of the sample fluid through a biocompatible lateral flow matrix or membrane which may be comprised of separate pads or segments, or alternatively comprised of a single lateral flow matrix provided with various gradations of density, porosity, or material composition for different fluid processing results along the length thereof. In FIGS. 21A-21D, the blood separator zone 385, the protein binding zone 399, the antibody binding zone 401, and the capture zone 312 are combined into a series of lateral flow pads as described below.

As illustrated in FIG. 20A, the micro-fluidic circuit 227 is provided with the draw-off reservoir or initial sample chamber 394. In this embodiment, the draw-off reservoir 394 is associated with a melt plug and vent. The melt plug is controlled by the processor 142 and/or the controller 190. At a pre-determined time, the melt plug associated with the draw-off reservoir 394 is first activated to place its associated lancet 159 in fluid communication to thereby draw off any blood that may have resided in the lancet from the time of application of the patch to the time the particular circuit 227 is required by the controller. After the initial draw-off of blood, the draw-off reservoir is then fluidly isolated from the circuit by any one of the means described above. In this manner, when the initial sample collection chamber 394 is activated by the controller 190, a draw of fresh blood having real-time or then current biological characteristics of the user is then directed by capillary action into the metering chamber 304 as intended. As would be readily understood by those skilled in these arts, given the present disclosure, the draw-off reservoir aspects of the present invention may be advantageously employed in any of the embodiments hereof, and is preferably used in any fluidic circuit 227 that is employed in connection with the time-delayed sample acquisition aspects of this invention.

The reservoir layer 379 includes the drug-release reservoir 389 as shown. The drug-release reservoir 389 may be pre-loaded with a predetermined amount of a prescribed drug according to the time-release aspects of this invention. The drug-release reservoir 389 may have one pre-loaded reservoir or alternatively it may be subdivided into several smaller reservoirs each having a pre-determined amount of liquid drug stored therein for time-release application. According to this aspect of the present invention, a pre-scribed dosage of drug, for example, is released from the drug-release reservoir 389, directed to the respective supply lancet, tubule, or micro-probe 397 through suitable fluid circuits, and then thereby caused to enter the blood stream of the user. As in the embodiment of the insulin reservoir 395 shown in FIG. 18C, the drug-release reservoir 398 may be provided with dispensing nozzles 377 that are opened by a command from the controller 142 by use of the heating elements 326 as described above. Through suitable supply fluid circuits, a pre-determined dose of liquid drug is thereby administered to the user of the device. The logic controller 190 may include expert software that determines the drug needs of the patient and then administers a proper dosage of drug as based on the detected results of the stress assay. As would be readily apparent to one of skill in these arts, the device so described herein is not specifically limited to conducting stress tests and administering a determined amount of liquid drug as based on those tests, but may be readily applied and adapted to a wide verity of different assays and drug or hormone release therapies or treatments. As described above, the drug release command may be doctor administered by patch/PC/network/doctor communications, rather than by patient or patch administration.

Figure 20B:
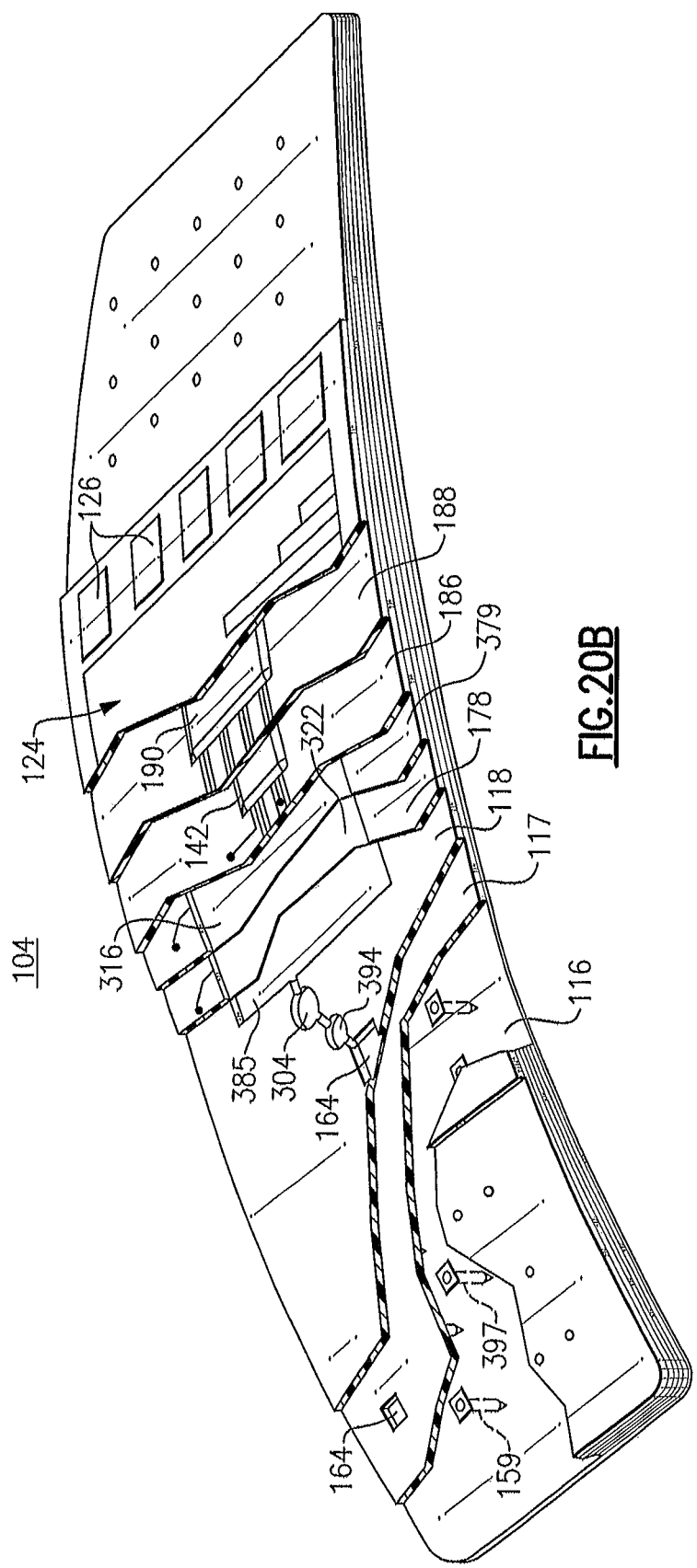
FIG. 20B is a perspective view with cut-away sections showing a fully assembled personal diagnostic device including the layers illustrated in FIG. 20A for performing stress analysis according to certain aspects of the present invention.

FIG. 20B is a perspective view with cut-away sections showing a fully assembled stress patch including the layers illustrated in FIG. 20A for performing stress analysis according to certain aspects of the present invention. More particularly, FIG. 20B shows the minimally invasive tubules, lancets, or micro-probes 159, the supply tubule or micro-probe 397, the reservoir openings 164, the draw-off reservoir or an initial sample collection chamber 394, the blood metering chamber 304, the micro-wire detector 322, the optional wash buffer wash buffer 316, the signal processor 142 in the signal processing layer 186, the controller 190 in the logic and input/output controller layer 188, the output video display monitor 124, and the individual fixed-display results windows 126.

Referring next to FIGS. 21A, 21B, and 21C, there is depicted a series of related cross-sectional side views showing the progression of a sample through the fluidic processing circuit 227 of the device illustrated in FIGS. 20A and 20B as implemented to perform stress analysis. In this implementation of the stress patch, blood sample is withdrawn via the microprobes 159 at specified time intervals throughout the life time of the stress patch. There may be multiple collection sites, and/or multiple inlet ducts, and/or multiple reservoirs as described above. Additionally, there may be several microprobes 159 that extract blood and direct the sample into a single micro-fluidic circuit 227 in the patch.

With reference now specifically to FIG. 21A, there is shown a fluidic circuit for analysis of cortisol. The circuit includes melt plugs 324, 244, and 350, detent pressure valves 330, melt valves 332, the initial sample collection chamber 394, the sample metering chamber 304, vent ports 340 having filter material 342, and a biocompatible membrane subdivided into different sections including a cell separation pad 388, a protein capture or binding pad 396, a reagent pad 400, a capture and sample analysis pad 402, and an adsorbent pad 392. Reagents required for the assay are preloaded into the reagent pad 400. These reagents may include a signal agent 398 made from a micro-particle and a target molecule binding agent such as an antibody that binds specifically to cortisol. Capture agents 378 having affinity to cortisol are located in the analysis pad 402. The capture agents 378 are preferably bound to the analysis pad 402 such that when the target molecule cortisol moves through the analysis pad 402 and binds to the capture agent 378, it is held in place by the capture agent for analysis.

Preferably about 10 to 30 μl of blood are withdrawn at specified time intervals. The microprobes are preferably coated with anticoagulant to prevent blood clotting. When the first melt plug 324 is opened, blood in the microprobe 159 enters the initial sample collection chamber 394 (FIG. 21B). This is performed, as described above, to flush out any old blood accumulated at the tip of the microprobes so as to provide a fresh blood sample for analysis. The next step is opening the second melt plug 344 to allow fresh blood to enter the metering chamber 304 (FIGS. 21B and 21C). Once the sample reaches a desired volume, chamber 304 is fluidly isolated by closing melt plugs 332. After metering the sample, the third melt plug 350 is opened and the metered sample is allowed to move into the biocompatible membrane (FIG. 21D) where cells are separated from the sample in pad 388 and proteins, specifically cortisol binding proteins, are then removed form the sample in pad 396. Pad 396 is preferably coated with protein capture agents that remove specific proteins from the sample. The sample then continues to move through the biocompatible membrane through the reagent pad 400 where cortisol 410 binds to the signal agent 398. This complex then moves into the analysis pad 402 where the capture agents bind to the cortisol 410 having attached thereto a signal agent 398. An incident beam of electromagnetic radiation 373 is then directed through pad 402 into a detector 322 which measures the modified light transmitted through pad 402. The light source 320 and the detector 322 utilized in this embodiment of the stress patch may be preferably of the micro-wire emitter and detector types described above. The presence and amount of cortisol is then analyzed by determining the difference between the intensity of the transmitted light before and after the sample is introduced into the analysis pad 402 and comparing the difference with a sample having a known amount of cortisol.

As described above, the blood or cell separation is mediated via the cell separation pad 388 that will separate RBC and WBC from the plasma or serum. In a typical operation, a blood fluid sample (10-30 μl) is withdrawn from the collection tubule and from here is drawn by capillary action through the cell separation pad. As the sample migrates through the filter, the fibrous network material making up the cell separation pad retards the movement of particulate matter, including blood cells, acting to partially remove blood cells before the sample reaches the protein binding pad 396.

In blood serum, there exist several cortisol binding proteins which can interfere with a cortisol immunoassay. The most commonly cited interfering protein is the protein transcortin (TC). The second step in the cortisol assay is its displacement from the binding proteins. As the plasma or serum sample migrates into the protein binding pad 396 by capillary action. The protein binding pad 396 consists of a conjugate pad or membrane, where a protein binding agent such as 8-anilino-1-naphthalene-sulfonic acid (ANS) is impregnated; which at low pH will free the serum cortisol from its endogeneous binding protein.

Because the clinically significant concentration range of cortisol is very small (e.g. about 12.5 to 800 ng/ml), cortisol concentrations are commonly determined via immunoassay techniques. In an alternative embodiment to the sandwich immunoassay and related method described above, the assay may be implemented as a competitive assay between preloaded labeled cortisol and the cortisol in the sample for a limited number of binding sites on the antibody coated analysis pad 412. A variety of labels or signal agents is known and can be implemented in the present invention. Micro-particles may be used as described above, and fluorogenic materials useful in a fluoroimmunoassay (FIA) described in U.S. Pat. No. 3,940,475 to Gross may also be used as an alternate signal agent. Another alternative signal agent includes enzyme labels coupled to antibodies or antigens used to perform an enzyme immunoassay (EIA) as illustrated in U.S. Pat. No. 3,654,090 to Schuurs et al. As used herein, the expression labeled substance, label, marker, tracer, or the equivalent, includes any of those known labels. By way of non-limiting example, enzyme labels such as Horse radish peroxidase or alkaline phosphatase which produce a detectable signal can be used in this assay.

The biocompatible membrane is preferably formed from conjugate pads or membrane strips that are commercially available. Membrane strips with good release efficiency are preferred which facilitate the migration of labeled cortisol into the analysis pad. By way of non-limiting example, hydrophilic polyethersulfone membranes can be used for this purpose. The movement of serum through this layer will allow the migration of labeled cortisol to the analysis pad.

As illustrated in FIGS. 21A-21D, impregnated or immobilized on the analysis pad 402 (nitrocellulose or borosilicate paper matrix) are antibody capture agents 378 against cortisol 410. By way of non-limiting example, antisera raised against cortisol 21 hemisuccinate and cortisol 3 carboxy methyloxime conjugates have proved suitable and are widely used for direct immunoassays without sample extraction. Antibodies may be immobilized on a solid phase by a variety of methods known in the art, including covalent coupling, direct adsorption, physical entrapment and attachment to a protein-coated surface. For references describing this methodology, see Silman, I. H. and Katchalski, E. in Annual Review of Biochemistry, Vol. 35, p. 873 (1966); Melrose, G. J. H., in Review of Pure and Applied Chemistry, Vol. 21, p. 83, (1971); and Cuatrecasas, P. and Anfinsen, C. B., in Methods in Enzymology, Vol. 22, (1971).

After capture, the analysis pad may be washed to remove unbound signal agents and cortisol. The wash process can be initiated by a time-controlled opening of a plug connecting a wash reservoir 316, FIG. 20A, to the analysis pad. In an enzyme assay implementation wherein the signal agent is an enzyme, a chromagen substrate that reacts with the enzyme to produce a detectable reaction may be mixed with the wash buffer. The wash buffer will elute unbound Enzyme-labeled cortisol while concomitantly allowing the bound enzyme to catalyze substrate cleavage. The wash buffer will be drained into the adsorbent pad.

The amount of enzyme-labeled cortisol can be quantified by optical detection (absorbance, reflectance, transmittance or fluorescence) and from there the concentration of sample cortisol will be derived. The concentration of cortisol will be computed using a pre-established standard curve.

Sports Performance Monitoring Implementations and Methods

Timely diagnosis of dehydration, heat stroke, or hypothermia is critical for athletes participating in sporting activities, as these conditions may lead to exercise-associated-collapse, which is linked with morbidity and mortality due to excessive physical activity. The two main causes for exercise-associated-collapse are exercise-induced-hyponatramia and cardiac disorders presenting as arrhythmias, cardiac arrest and myocardial ischemia.

Exercise-induced-hyponatramia is caused by abnormal levels of electrolytes, more specifically a decreased plasma sodium concentration (<136 mmol/L). Some cardiac disorders are attributed to abnormal lactate levels. Indeed, blood lactate levels have been demonstrated to be useful in establishing a diagnosis of acute myocardial ischemia within 3 hours of symptom development (Schmiechen, N.; Han, C. and Milzman, D. Ann Emerg Med 1997; 30:571-577). Furthermore, elevated lactate values in critical care medicine generally mean that tissues are not getting adequate oxygen. Oxygen deprivation of many tissues (e.g. brain, heart, kidney) correlates strongly with morbidity and mortality. Consequently, elevated lactate in many critical settings demands its rapid discovery, an explanation for the oxygen deprivation and rapid therapy to correct it. Therefore, monitoring lactate and oxygen levels may be useful in ruling out acute myocardial infarctions in athletes presenting with exercise-associated collapse.

Conventional blood analyte monitoring methods generally require the drawing of a blood sample (e.g., by finger prick) for each test, and a determination of the analyte level using specific diagnostic devices by specialized technical personnel. This may be problematic in sporting activities in areas remote from traditional medical facilities. Accordingly, there remains a need in the art for medical devices which provide effortless analyte measurements in field or home-testing applications, particularly where continual and/or automatic monitoring is desired.

Figure 22A:
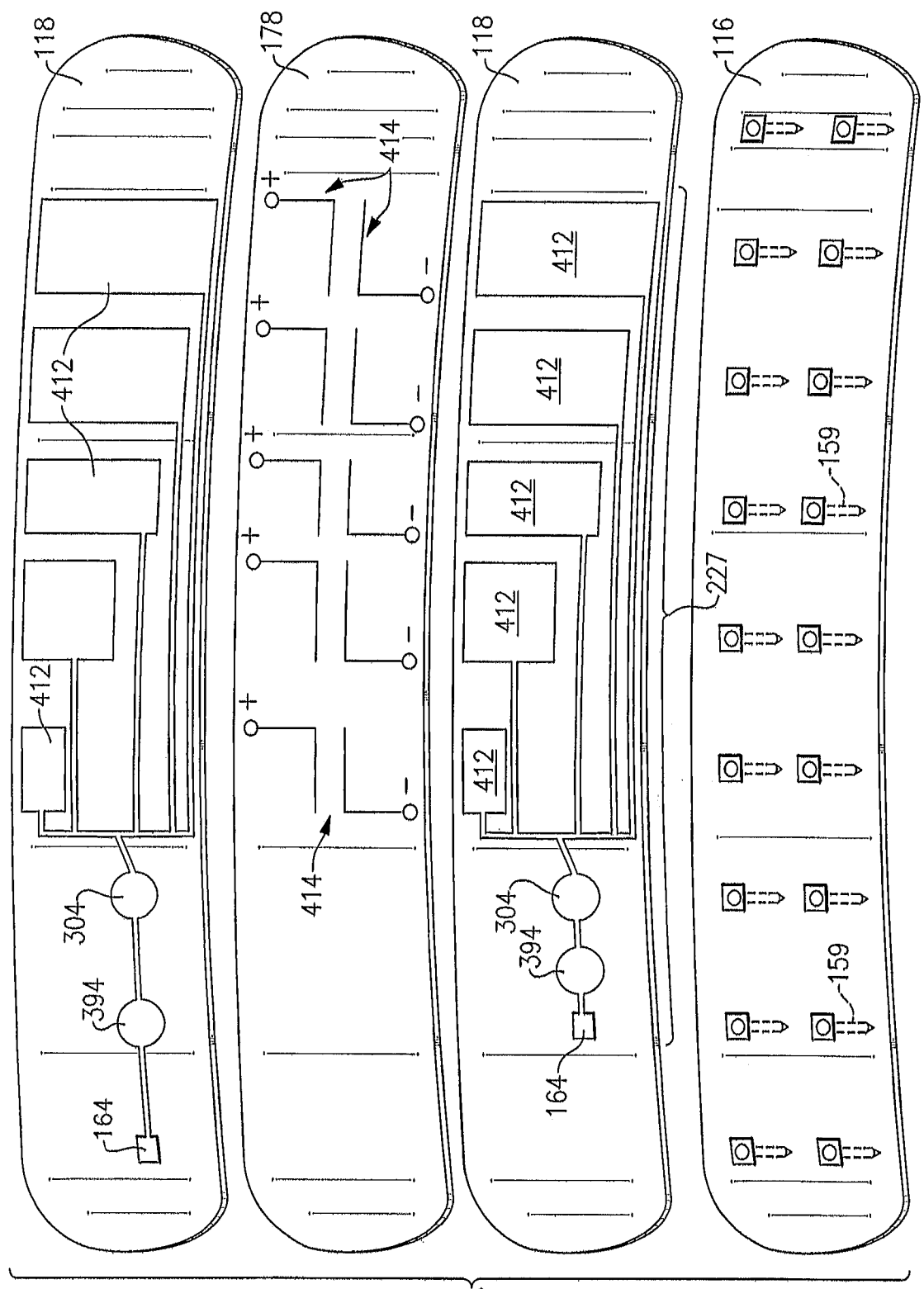
FIG. 22A is an exploded perspective view of a sample acquisition layer, repeated fluid processing layers, and a results detection layer as employed in yet still another alternative specific embodiment of the personal diagnostic device according to the present invention implemented to perform sports performance analysis during real-time use.

With reference now to FIG. 22A, there is shown an exploded perspective view of the principal fluid sample processing detection layers of a sports patch according to yet another preferred embodiment of the present invention. These include the sample acquisition layer 116, the fluid processing layer 118, the results detection layer 178 including electrodes 414, and another fluid processing layer 118 as utilized to perform sports performance monitoring. As illustrated, the sample acquisition layer 116 includes the minimally invasive tubules, lancets, or micro-probes 159 that penetrate the skin surface to thereby acquire blood samples from capillaries near the epidermis. Each pair of electrodes 414 is assigned to a particular analysis chamber 412 and situated in register therewith as illustrated.

The micro-fluidic circuit 227 illustrated in FIG. 22A includes the reservoir opening 164, the draw-off reservoir or initial sample collection chamber 394, the blood metering chamber 304, and a series of analysis chambers 412. The sample processing layer 118 may include one micro-fluidic circuit 227 or may alternatively preferably include several micro-fluidic circuits 227 formed therein. Alternatively, the device 104 may include several sample processing layers 118 (as represented by the second layer 118) each with a single or a multiple number of micro-fluidic circuits 227. In this manner, several blood samples may be taken over time by using flow control at the first fluid channel 168 as described with reference to FIGS. 13A to 13E. Each of these separate blood samples may then be processed in real time in a separate micro-fluidic circuit 227.

Figure 22B:
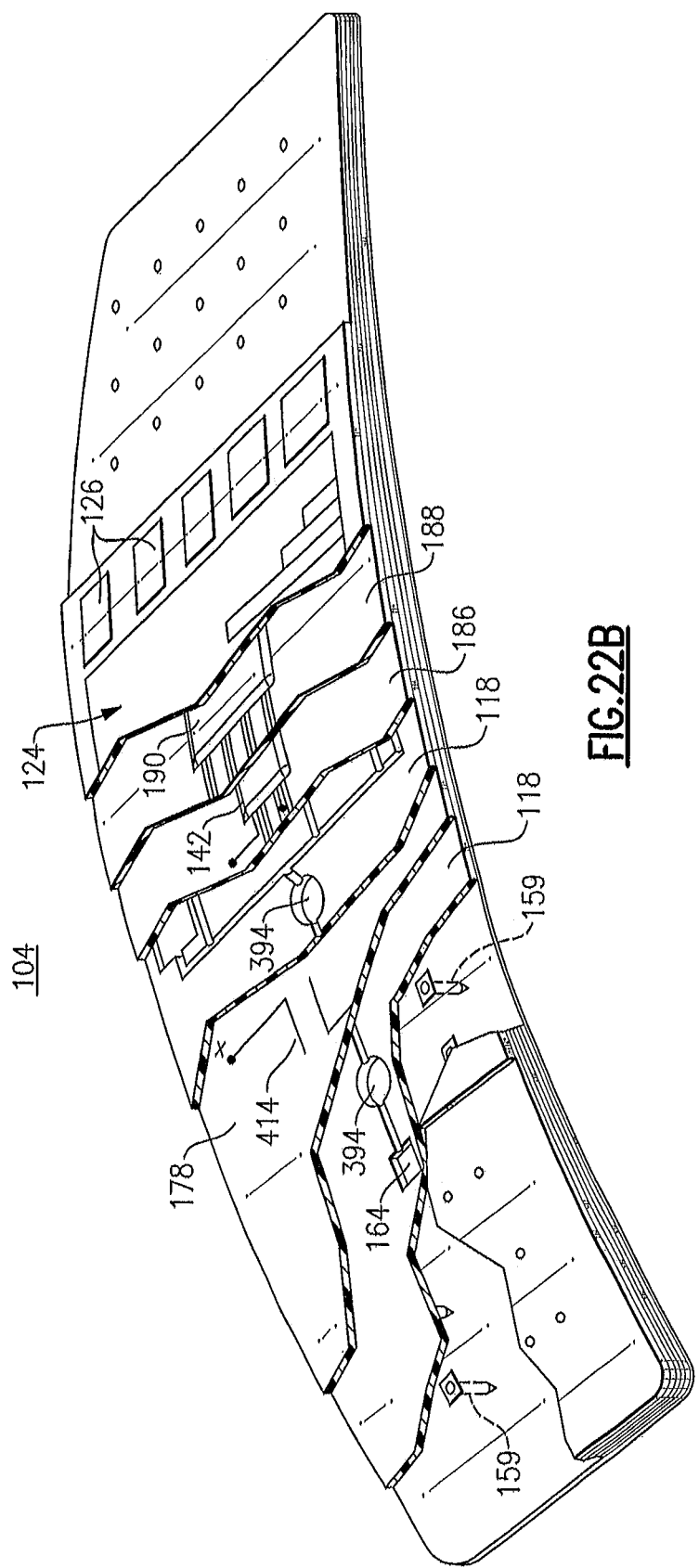
FIG. 22B is a perspective view with cut-away sections illustrating a fully assembled personal diagnostic device including the layers shown in FIG. 22A for conducting sports performance analysis according to other certain aspects of the present invention.

FIG. 22B is a perspective view with cut-away sections showing a fully assembled sports patch including the layers illustrated in FIG. 22A for performing sports performance analysis according to certain additional aspects of the present invention. More particularly, FIG. 22B shows the minimally invasive tubules, lancets, or micro-probes 159 in the sample acquisition layer 116, the reservoir openings 164 in layer 118, the draw-off reservoir or an initial sample collection chamber 394 also in layer 118, the electrodes 414 in the results detection layer 178, the second fluid processing layer 118, the signal processor 142 in the signal processing layer 186, the controller 190 in the logic and input/output controller layer 188, the output video display monitor 124, and the individual fixed-display results windows 126.

Figure 23A:
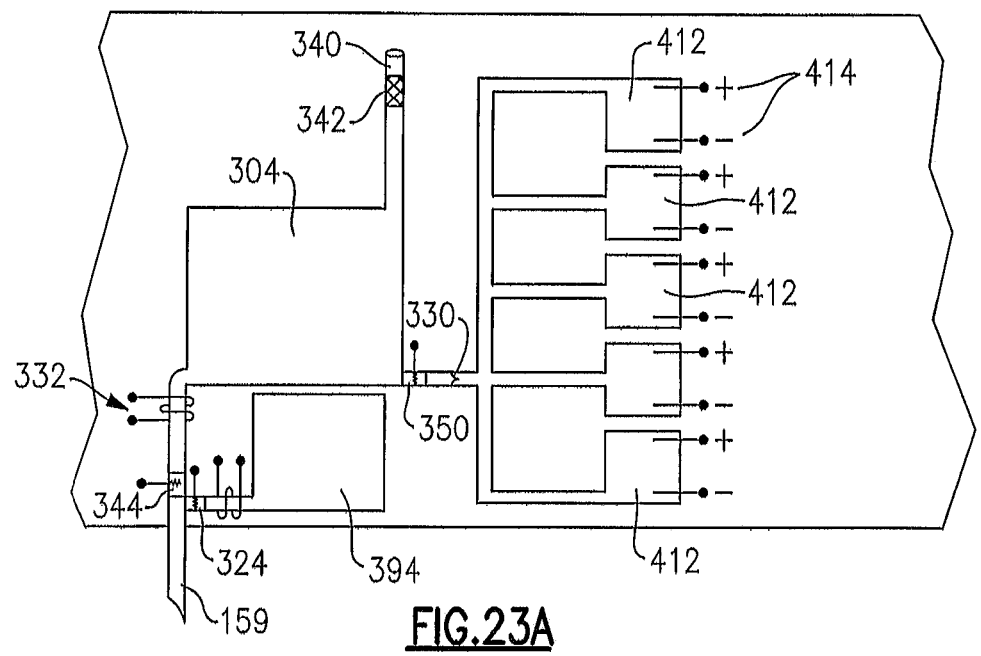
FIGS. 23A to 23E present a series of a cross-sectional side views showing the progression of a sample through the fluidic processing circuit of the device of FIGS. 22A and 22B as implemented to perform sports performance analysis.

FIGS. 23A-23E, illustrate a cross-sectional side views showing the progression of a sample through the fluidic processing circuit of the present sports performance monitoring patch, herein after referred to for convenience as the sport patch. FIG. 23A shows typical components of a fluidic circuit including the microprobe 159, a first melt valve 324, the initial sample collection chamber 394, a second melt valve 344, a metering chamber 304, a vent port 340 having a filter 342, a third melt plug 350, a detent pressure valve 330, analysis chambers 412, and electrodes 414.

Figure 23B:
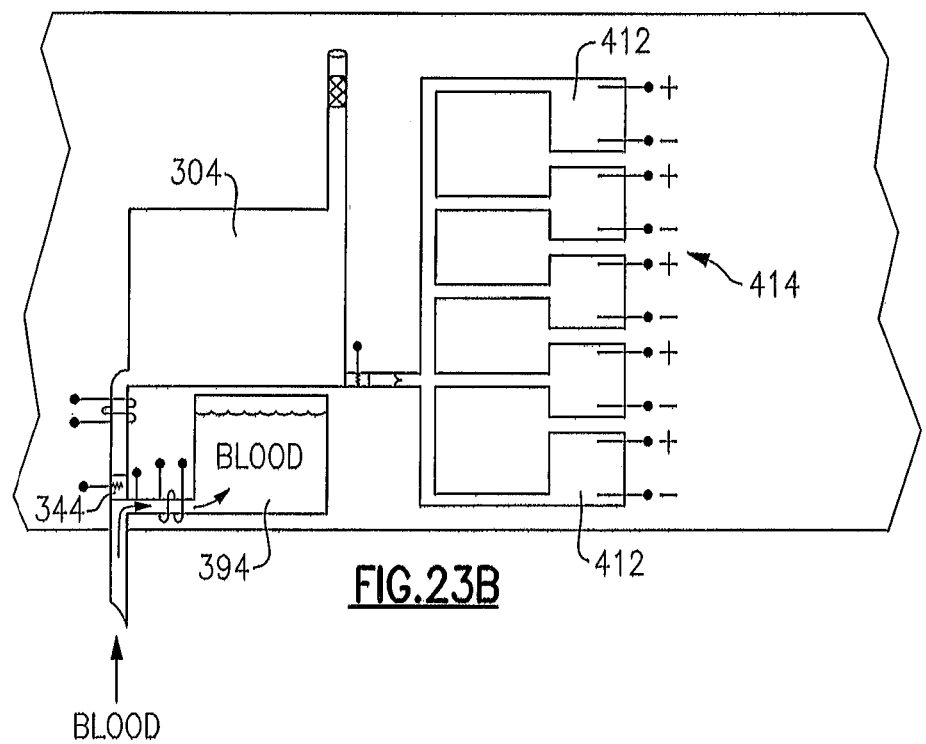
Figure 23C:
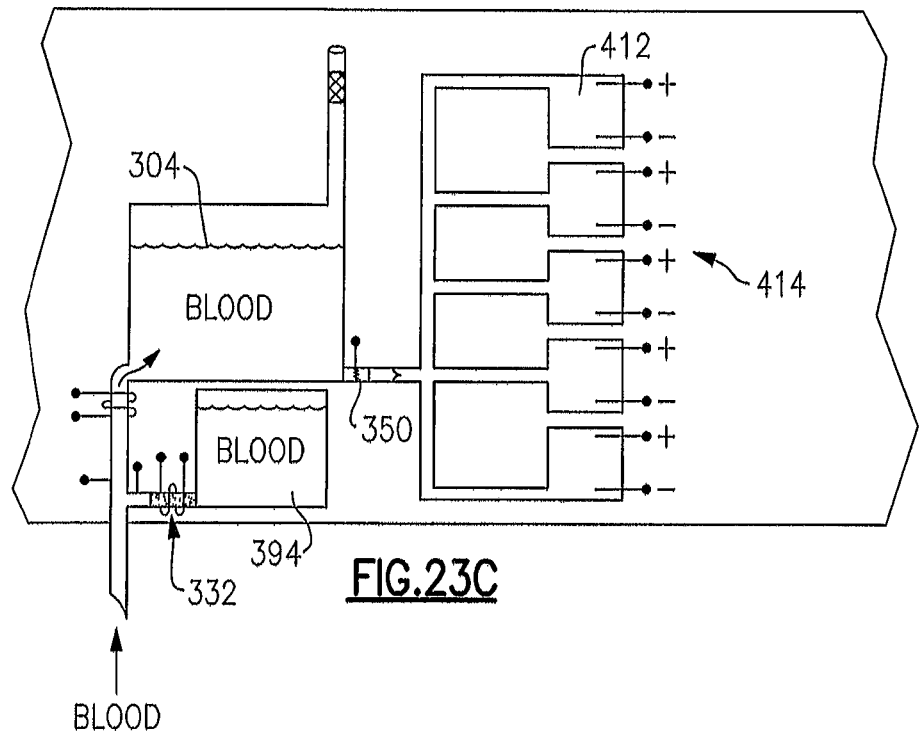
Figure 23D:
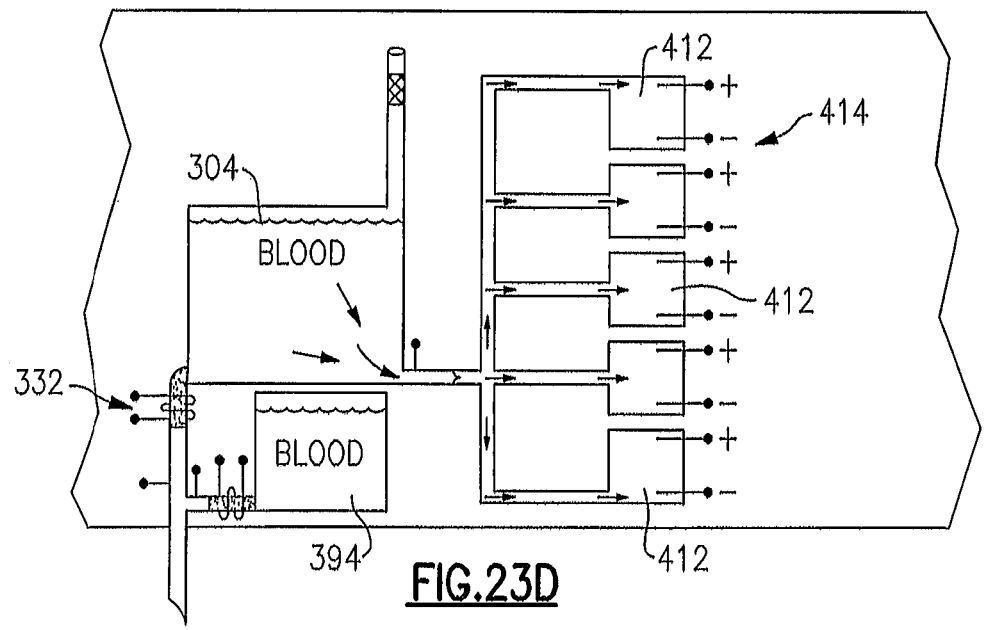
Figure 23E:
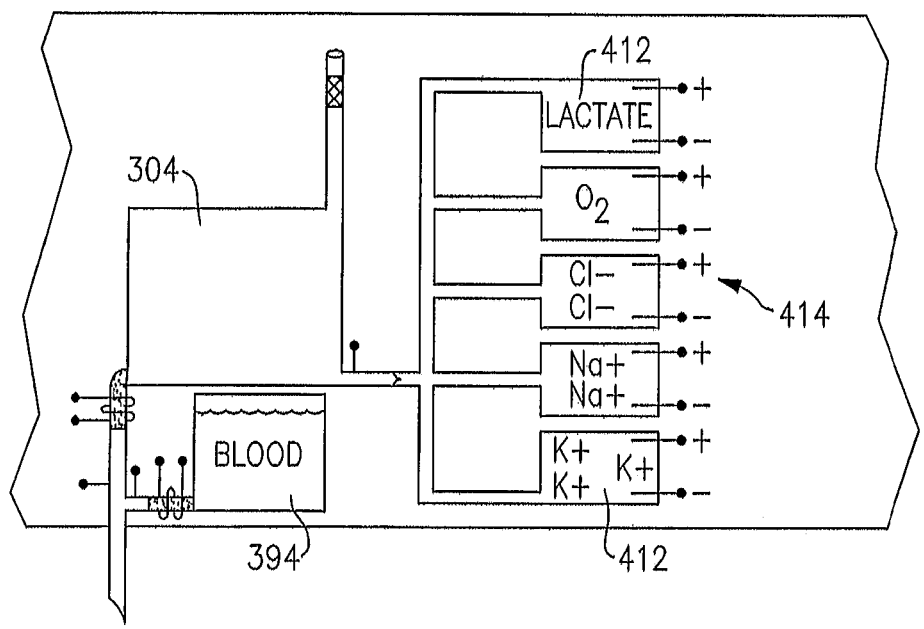

The first step in the analysis is removal of old blood accumulated in the microprobe 159 so as to provide a fresh blood sample for analysis. This step is illustrated in FIG. 23B where the first melt plug 324 is opened allowing blood to enter the initial sample collection chamber 394. Chamber 394 is then sealed by closing a melt valve 332 in the channel leading into chamber 394 (FIG. 23C). The second melt plug 344 is then opened to allow blood to enter the metering chamber 304. Once the blood in the metering chamber 304 reaches a pre-determined amount, the blood flow into chamber 304 is cut off by closing the melt valve in the channel leading into chamber 304 (FIG. 23D). The third melt valve 350 is then opened to allow the sample to enter into the analysis chambers 412 as illustrated in FIG. 23D. The amount of analytes in the sample are then determined electrochemically using appropriate electrodes 414 specific for each analyte as described below. These analytes may include hydrogen peroxide ($H_2O_2$), oxygen ($O_2$), chloride ($Cl^-$), sodium ($Na^+$) and potassium ($K^+$) as shown in FIG. 23E.

More specifically now regarding the methods hereof, blood sample is withdrawn via microprobes at specified time intervals throughout the life time of the sport patch. There may be multiple collection sites and/or multiple inlet ducts and/or reservoirs as described above. There may be several microprobes to extract blood into the micro-fluidic circuit in the sports patch. Preferably about 15-30 µl of blood is withdrawn at specified time intervals. The microprobes are preferably coated with anticoagulant to prevent blood clotting. The micro-fluidic circuit includes the initial collection chamber or draw-off reservoir 394 with programmable valves to flush out any old blood accumulated at the tip of the microprobes. Fresh blood sample is then channeled into the metering chamber 304 then distributed in to analysis chambers 412.

As discussed above, the detection of the analytes of interest is electrochemical, hence no blood separation is required prior to analysis. However, should optical detection (absorbance, reflectance, or transmittance for example) be the method of choice, a blood separation step may be included. In this alternate embodiment, the first layer on the sport patch will be a blood or cell separation pad that will separate RBC and WBC from the plasma or serum similar to that described above in conjunction with FIGS. 21A to 21D. In a typical operation, a blood fluid sample (15-30 µl) is withdrawn from the collection tubule and from here is drawn by capillary action through the cell separation pad. As the sample migrates through the cell separation pad, the fibrous network material making up the cell separation pad retards the movement of particulate matter, including blood cells, acting to partially remove blood cells before the sample moves into the subsequent pads.

As described above in connection with FIG. 23E, the whole blood sample migrates into 5 analyses chambers (situated in parallel configurations). The analysis chamber used to quantify lactate is preloaded with all enzymes necessary for the lactate reaction diagrammed below. For the lactate assay, the analysis chamber may contain lactate oxidase, a peroxidase and a substrate reagent which is converted by the peroxidase in the presence of $H_2O_2$ to the detectable reaction product. Given the method of detection of choice in this patch which is electrochemical, the enzyme peroxidase and chromagen substrate are omitted. In this case, the $H_2O_2$ produced is oxidized at a platinum electrode to produce an electric current which is proportional to the sample lactate concentration. Presented below is the lactate assay reaction related to the present sports patch.

Lactate Assay:

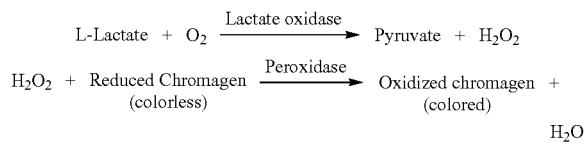

Oxygen is measured amperometrically. An oxygen permeable membrane allows oxygen to permeate into an internal electrolyte solution where it is reduced at the cathode. The oxygen reduction current is proportional to the dissolved oxygen concentration.

Oxygen electrodes are used to measure the oxygen concentration. The composition of oxygen electrodes is well known to those skilled in the art. A typical oxygen electrode contains a working electrode (cathode), a counter electrode (anode), an electrolyte, and a gas permeable membrane. The oxygen dissolved in the electrolyte through the gas permeable membrane and water react with electrons on the working electrode (cathode) to form hydroxide ions $OH^-$ (i.e., $O_2+2H_2O+4e^-=4OH^-$) and cause an electric current in relation to the amount of the dissolved oxygen so that the oxygen concentration can be estimated from the electric current detected.

A tetrafluoroethylene/hexafluoroethylene copolymer (FEP) film is preferably used as the gas-permeable film, and the thickness of this film is preferably smaller than 20 µm. A gold electrode, a platinum electrode, a carbon electrode and the like are preferably used as the working electrode (cathode), and similarly, a gold electrode, a platinum electrode, carbon electrode and the like are preferably used as the counter electrode (anode). Furthermore, a silver/silver chloride electrode is preferably used as the reference electrode.

An aqueous solution of potassium chloride, an aqueous solution of potassium hydroxide and the like are preferably used as the electrolyte.

Sodium, potassium, and chloride are measured by ion-selective electrode potentiometry. Concentrations are calculated from the measured potential through the Nernst Equation. Different ions are measured by specific ion-selective electrode. As known to those skilled in the art, ion-selected electrodes, which are commercially available, are made of membranes which are made of varying composition of the glass electrodes with directed selectivity for the ion of interest.

An algorithm may be included in firmware or software that will result in a beep should the analyte concentration drop below or is higher than a certain level so that the patient can take appropriate action. Use of the sports patch includes real-time use during sports activity. Such sports may include daily work-outs in the gym or health club by ordinary individuals or more disciplined work-outs by professional athletes such as marathon runners, swimmers, or hockey, baseball, football, and soccer players, for example.

In the case of daily works-outs in the health club, an individual may monitor the body's response to certain exercise routines. With the aid of a trainer, results from the sports patch may be used to modify the work-out routine and/or the diet of the individual. In this manner, health and nutrition aspects for good health maintenance are integrated with use of the sports patch.

In the case of professional sports the sports patch may be similarly used. In addition thereto, the sports patch may be equipped with RF detectors and transmitters as discussed above. In this manner, the coaching staff may use wirelessly transmitted diagnostic information to make coaching decision during an event or game. For example, in the game of professional hockey, line changes are of critical importance tactically and strategically. Thus the inventors hereof propose a sports patch that is used to monitor the performance level of a professional during a game or other competitive match. The retail time information is transmitted from the sports field or ice rink to the coaching staff. The coaching staff then utilizes this information in making coaching decisions like line changes in professional ice hockey, substitutions in basketball, football, or soccer, for example. The sports patch may be similarly utilized during training sessions.

Elderly Care Monitoring Implementations and Methods

One of the major challenges facing the world today is providing health care to our ever-growing aging population. Not only will there be more individuals reaching the retirement age of 65, but they will be living longer. Along with longevity come chronic ailments such as heart diseases, kidney diseases, and diabetes, all of which infringe on one's independence. The need to provide economical healthcare to the elderly is therefore becoming more and more pressing.

Real time measurements of cardiac biochemical markers are critical in the diagnosis of cardiovascular diseases. Furthermore, patients with kidney diseases are also at high risk for developing cardiovascular diseases. Therefore, early detection of deteriorating kidney function and intervention can improve outcomes. Measurement of serum creatinine can be used to detect a reduction in renal function. Anemia is known to affect up to 80% of patients with renal impairment, with a reduction of life and early death. Measurement of total hemoglobin can be used to monitor anemia status.

Conventionally, the quantification of the above blood analytes generally require the patient to have their blood drawn at a medical facility and the determination of the analytes of interest is carried out by specialized technical personnel using specific diagnostic devices. However, the discomfort and inconvenience associated with this process may lead to poor patient compliance, resulting in failure of timely diagnosis and treatment.

Accordingly, there remains a need in the art for medical devices which provide effortless analyte measurements in field or home-testing applications, particularly where continual and/or automatic monitoring is desired.

In view of the above, the inventors hereof propose a personal diagnostic device for monitoring cardiac, renal, and anemia markers, for example, herein after referred to as an elderly care patch or elder care patch. The proposed elder care patch allows measurements of cardiac markers (CK-MB, Tnl, and myoglobin), the renal marker (creatinine), and anemia marker (total hemoglobin). The elder care patch thus provides a quick, effortless device and method for analyte determination using only a simple patch or bracelet that interfaces with a personal computer or alternatively interfaces wirelessly with a smart home environment that may be advantageously networked with a professional health care service.

With reference now to FIG. 24A, there is shown an exploded perspective view of the principal fluid sample processing and detection layers of an elder care patch according to still yet another preferred embodiment of the present invention. These include the sample acquisition layer 116 including the light sources 320, the fluid processing layer 118, and the results detection layer 178 including the detectors 322 as utilized to perform elder care monitoring. As illustrated, the sample acquisition layer 116 includes the minimally invasive tubules, lancets, or micro-probes 159 that penetrate the skin surface to thereby acquire blood samples from capillaries near the epidermis. The fluid circuit illustrated in FIG. 24A includes the reservoir opening 164, the blood metering chamber 304 in a rectangular format, and three analysis chambers 412. In this particular embodiment, the light sources 320 are implemented as micro-wire emitters and the detectors 322 are implemented as corresponding micro-wire detectors as illustrated.

Figure 24B:
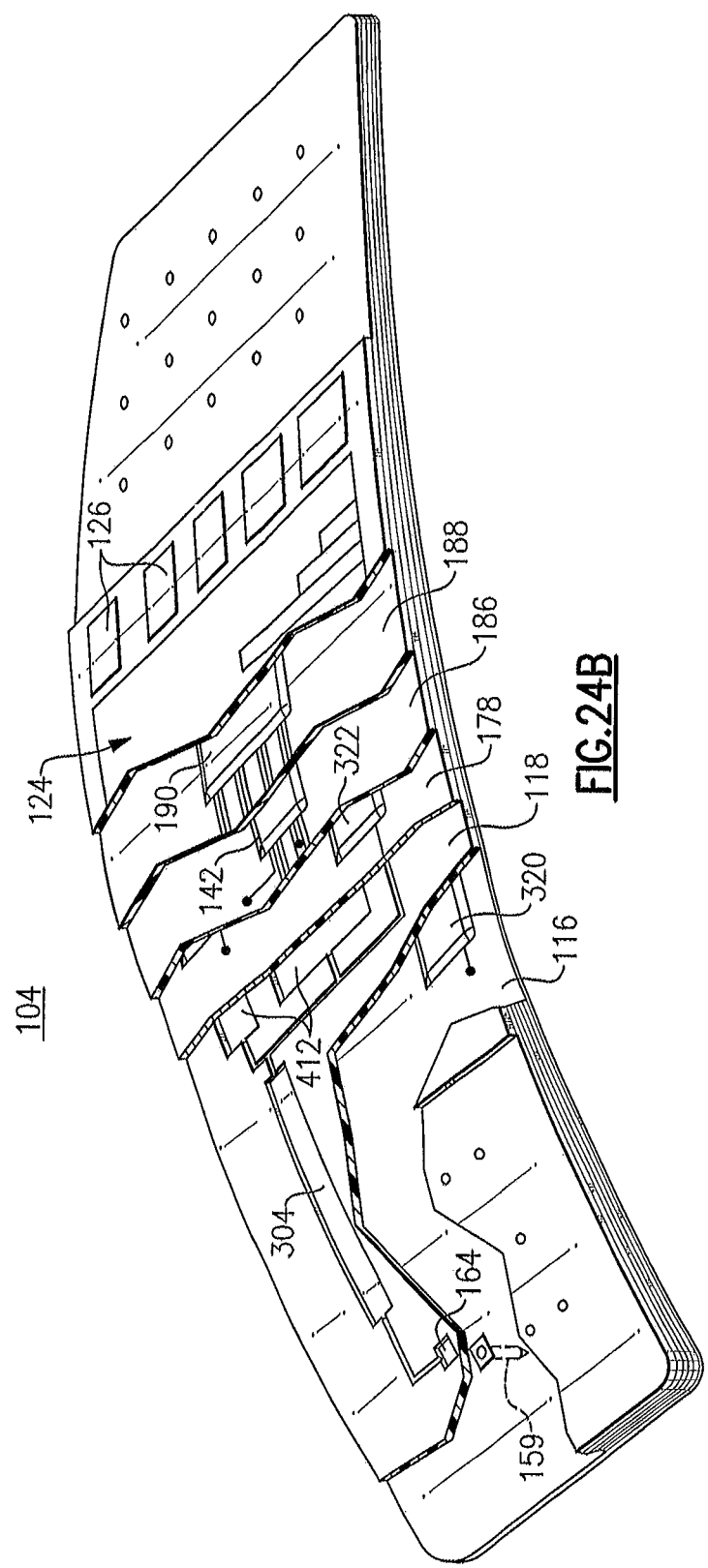
FIG. 24B is a perspective view with cut-away sections showing a fully assembled personal diagnostic device including the layers illustrated in FIG. 24A as utilized to perform elderly care monitoring in older patients.

FIG. 24B is a perspective view with cut-away sections showing a fully assembled elder care patch including the layers illustrated in FIG. 24A for performing elder care monitoring according to certain further and additional aspects of this present invention. More particularly, FIG. 24B shows the minimally invasive tubules, lancets, or micro-probes 159 in the sample acquisition layer 116, the reservoir openings 164 and analysis chambers 412 in the fluid processing layer 118, the micro-wire detector 322 in the results detection layer 178, the signal processor 142 in the signal processing layer 186, the controller 190 in the logic and input/output controller layer 188, the output video display monitor 124, and the individual fixed-display results windows 126.

Figure 25A:
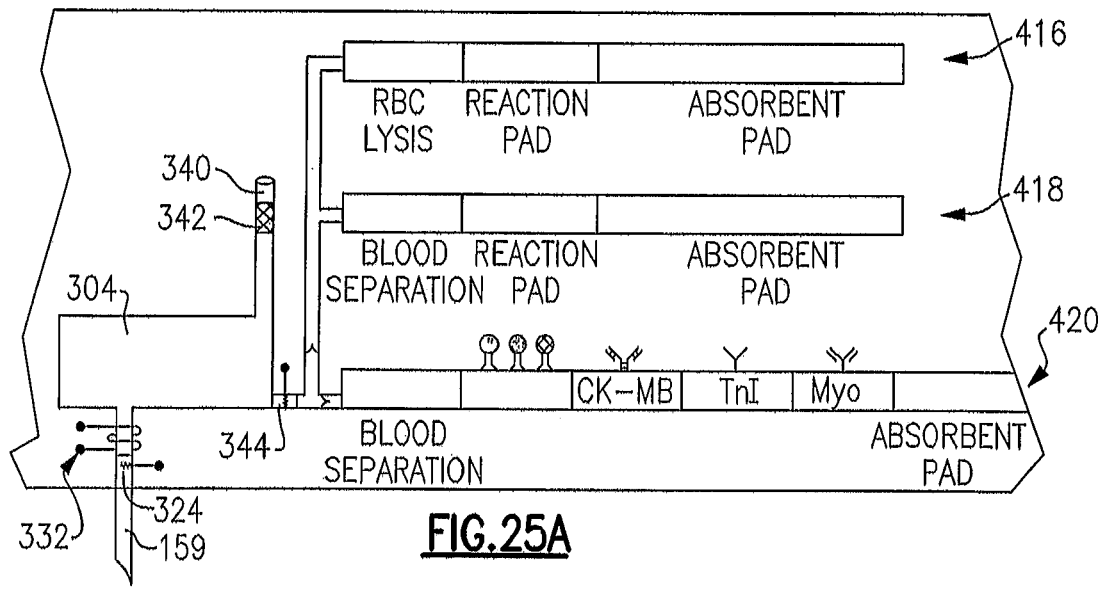
FIGS. 25A to 25D present a series cross-sectional side views showing the progression of a sample through the fluidic processing circuit of the device illustrated in FIGS. 24A and 24B as employed for elderly care monitoring in older patients.

FIGS. 25A-25D present cross-sectional side views showing the progression of a sample through the fluidic processing circuit of the elder care patch of FIGS. 24A and 24B as implemented to perform monitoring in older patients. Referring now specifically to FIG. 25A, there is shown a fluidic circuit for analysis of CK-MB, Troponin-I (Tn-I), myoglobin, creatinine, and hemoglobin. The fluidic circuit illustrated includes a microprobe 159, a first melt plug 324, a melt valve 332, a metering chamber 304, a vent 340 having a filter 342, a second melt plug 344, a first analysis membrane 416, a second analysis membrane 418, and a third analysis membrane 420. First analysis membrane 416 is used for analysis of hemoglobin while the second analysis membrane 418 is made for analysis of creatinine and the third analysis membrane is for analysis of the cardiac markers. The various assays and methods for detection and quantitation are described in detail below.

Figure 25B:
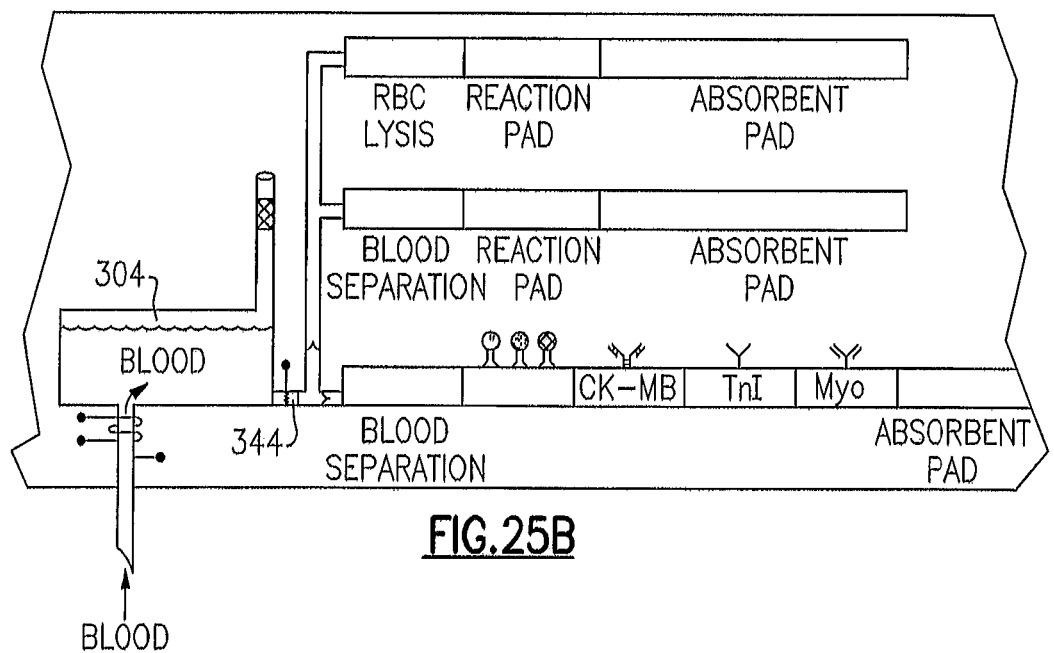
Figure 25C:
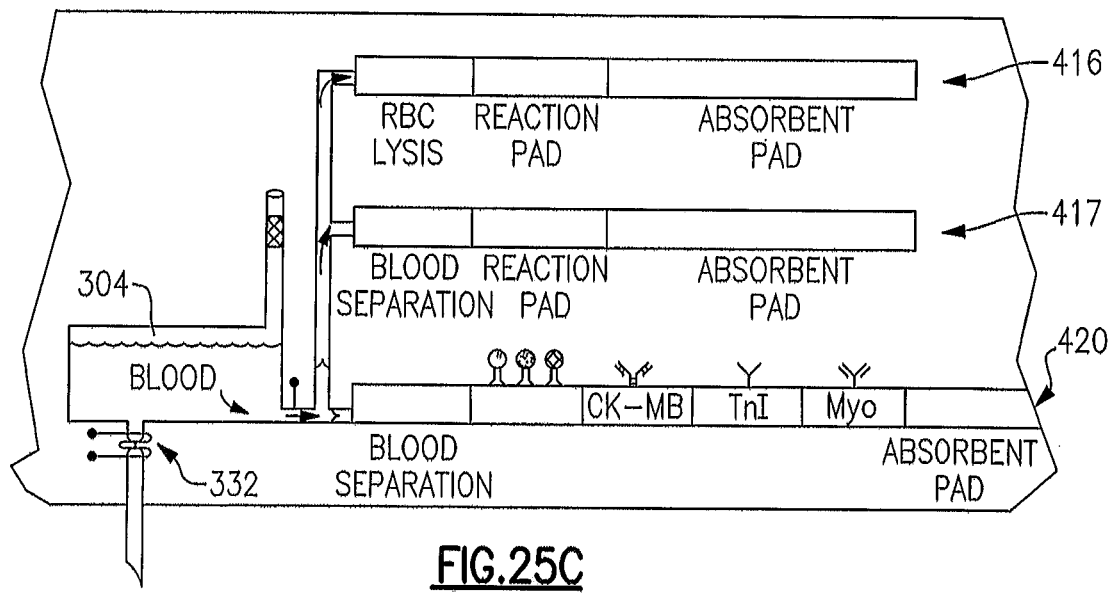
Figure 25D:
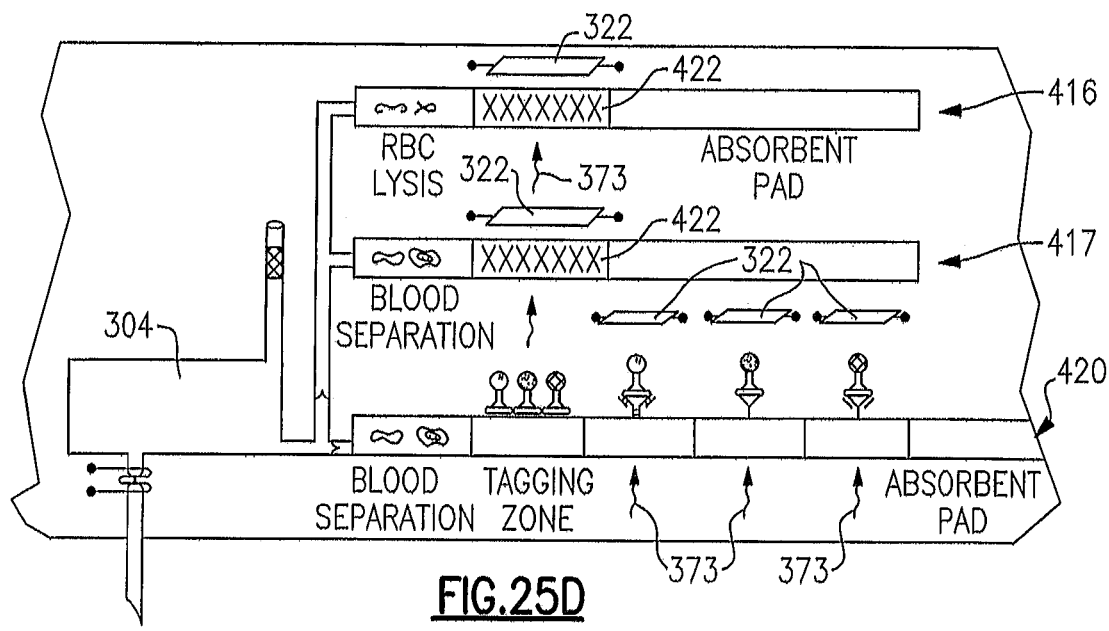

Moving next to FIG. 25B, plug 324 is opened allowing blood to enter the metering chamber 304. Once the blood level in the chamber reaches a pre-determined volume valve 332 is closed (FIG. 25C). The second melt plug 344 is then opened allowing the blood sample to flow into the analysis membranes 416, 418, and 420. FIG. 25D next shows the steps of the sample processing and analyses of the various analytes mentioned above.

The hemoglobin analysis is carried out in membrane 316 where RBCs are lysed in the RBC lysis pad which releases the hemoglobin. The sample containing hemoglobin then enters the adjacent analysis or reaction pad where preloaded reagents that react with hemoglobin produce a detectable signal 422. The incident beam of electromagnetic radiation 373 is then directed through the analysis pad and into the photo detector 322. The amount of light detected by the photo detector 322 is then analyzed to determine the hemoglobin concentration in the sample.

Creatinine analysis is carried in membrane 418 where cells are removed from the blood sample in the blood separation pad, serum then moves into the reaction or analysis pad where pre-loaded reagents react with creatinine through a series of reactions to produce a detectable product 422. Details of these reactions are described and discussed below. The amount of creatinine is then calculated based on the signal detected by the photo detector.

With continuing reference to FIG. 25D, the cardiac marker assay is performed in membrane 420 where the plasma is separated from the cells in the sample while the sample passes through the blood separation pad. The blood separation pad is preferably a sieve or filter having a desired pore size that prevents cells from passing through. The serum containing the various cardiac marker analytes then enter a tagging zone containing different types of signal agents specific for each analyte. The different signal agents may include a binding moiety that has specific affinity to the respective analytes. For example, a first signal agent may be a fluorescent micro-particle having attached thereto an antibody that binds to CK-MB, a second signal agent may be an opaque micro-particle having attached thereto an antibody that binds to TnI, and a third signal agent may be an IR (infrared) absorbing micro-particle having attached thereto an antibody that binds to myoglobin. As the sample flows through the tagging zone, each respective analyte is tagged with its respective signal agent. Membrane 420 includes a series of analysis pads each containing a binding agent specific for one of the analytes. For example, the first analysis pad may contain capture antibodies against CK-MB, the second capture antibodies against TnI and the third capture antibodies against myoglobin. So as the tagged sample moves through each of the analysis or reaction pads each respective tagged analyte will be bound to its respective capture agent in each respective analysis pad. In this manner, each of the analyte concentrations may then be determined by analysis of the amount of signal agent present in each respective analysis zone. As one of skill in the art would surmise in view of this disclosure, different types of light sources and detectors may be required for interrogation of the analysis pads. The fluorescent micro-particles will require a light source of a specific wavelength to excite the fluorescent label in the micro-particle and a specific photo detector will be need to detect the emitted light of a particular wavelength coming from the fluorescing micro-particle. The IR micro-particle will thus need an IR light source and the opaque micro-particle yet another appropriate light source. As illustrated above in FIG. 17B, the micro-wire detector may be implemented with different diameter individual semi-conductor micro-wires that each emits a specific wave length of light. Any desired packing density and variation of sizes, diameters, and resulting wavelengths may be provided. The micro-wire emitter 320 may be similarly constructed to achieve these desired results in combination with a corresponding micro-wire detector as described.

The following are details of reactions and detection systems that may be used for the above-described elder care patch of the present invention.

A. Quantification of Cardiac Markers CK-MB, TnI, and Myoglobin

Impregnated in the tagging zone or conjugate release pad is a first antibody to a cardiac marker of interest which is labeled with a particular signal label (colored latex particle or fluorescent tags or enzyme tags). The capture antibodies in the analysis pads can be produced in vivo or in vitro. Methods for the production of antibodies are well known to those skilled in the art. For example, see Antibody Production: Essential Techniques, Peter Delves (Ed.), John Wiley & Son Ltd, ISBN: 0471970107 (1997). Alternatively, antibodies may be obtained from commercial sources. Antibodies may be immobilized on a solid phase by a variety of methods known in the art, including covalent coupling, direct adsorption, physical entrapment, and attachment to a protein-coated surface.

The cardiac markers will bind to the first antibody in the sample layer. The movement of serum through this layer will allow the migration of the analyte-antibody complex to the analysis pad.

Impregnated on the analysis pad (nitrocellulose or borosilicate paper matrix) is a capture antibody, typically coupled to the analysis pad in a band like format to form a capture zone. The capture antibody captures the labeled analyte. The presence of the analyte creates a detectable signal line or band in the capture zone and a signal is produced (fluorescent or color). Excess labeled antibody can also continue to migrate along the solid phase and be captured by an immobilized antispecie antibody, creating a second signal band. This is used as an internal quality control check to indicate that the device has worked.

B. Quantification of Creatinine

The following section describes the quantification of creatinine and the creatinine assay as implemented and utilized in the elder care patch of the present invention.

Creatinine Assay:

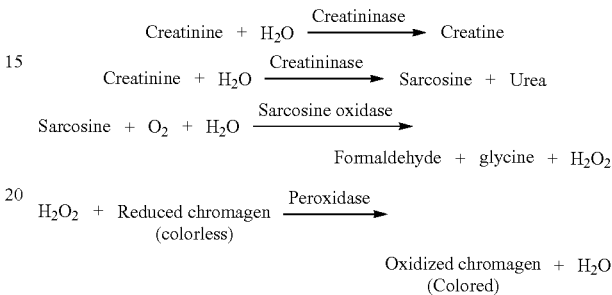

Reaction Zone:

Impregnated on a membrane are all enzymes necessary for the creatinine reaction shown above. For the creatinine assay, the reaction pad(s) contains creatininase, creatinase, sarcosine oxidase, a peroxidase, and a substrate reagent which is converted by the peroxidase in the presence of $H_2O_2$ to a detectable reaction product. Desirably, the reaction pads are porous, fused polymer substrate membranes having a thickness, after complete penetration of the fluid, of about 125 μm and side dimensions of about 1 mm. The absorption volume of each pad is preferably between about 5-10 μl.

Creatinine Quantification:

At the end of the reaction zone is the analysis zone, where the amount of hydrogen peroxide produced is quantified by absorbance via a chromagen that changes color upon being oxidized.

An algorithm may be included in firmware or software that will result in a beep should the analyte concentration drop below or is higher than a certain level so that the patient can take appropriate action. In addition thereto, various drugs, hormones, or other liquid therapies may be administered from the elder care patch according to the controlled time-release aspects of this invention.

C. Quantification of Total Hemoglobin

Hemoglobin assay is used to detect anemia. Anemia is known to affect 60-80% of patients with renal impairment, with a reduction in the quality of life and risk of early death.

Measurement of hemoglobin concentration has been conducted by means of a cyanmethemoglobin method. With this method, an erythrocytolytic or red blood cell lysing agent is used to lyse the RBCs in the RBC lysis pad. Several red blood cell lysing reagents and methods have been described by previous scientific publications and patents including, for example, U.S. Pat. Nos. 3,874,852; 4,286,963; 4,346,018; 4,485,175; 4,528,274; 4,751,179; and 5,731,206. The cell lysis reagents are available commercially. The RBC lysis pad may also contain a nonionic surfactant to reduce turbidity caused by the erythrocyte cell membranes. The released hemoglobin is oxidized by the action of an oxidizing agent in the reaction pad, such as potassium ferricyanate, to produce methemoglobin. Subsequently, the cyanide ions bind to methemoglobin to form cyanmethemoglobin (HiCN) which produces a stable hemoglobin measurement sample. The absorbance of the cyanmethemoglobin sample is measured at a predetermined wavelength. This method is accepted worldwide as the standard method to determine hemoglobin concentration.

For the hemoglobin assay, the reaction pad(s) contains potassium ferricyanide (0.6 mM), potassium cyanide 0.7 mM. In an alkaline medium, potassium ferricyanide oxidizes hemoglobin and its derivatives to methoglobin. Subsequent reactions with potassium cyanide produces the more stable cyanmethemoglobin which has a maximum absorbance at 540 nm.

At the end of the reaction zone is the analysis zone, where the amount of colored product is quantified. The detector measures the change in reflected or transmitted light before and after blood application to determine total hemoglobin.

An algorithm may be included in firmware or software that will result in a beep should the analyte concentration drop below or is higher than a certain level so that the patient can take appropriate action.

In this particular embodiment of the present invention, the elderly care patch or bracelet may be advantageously equipped with a voice activated or voice recognition patch sub-system wirelessly connected to and integrated with the patient's smart home environment. Thus according to further use methods of the present invention, if an elderly person is wearing a patch in a retirement community with remote sensing of real time output for all users in the community, as contemplated by the inventors hereof, and the patient has some type of abnormal health condition come on suddenly—the user may simply say aloud, for example, "call 911". The elder care patch then receives this voice command and dials 911 via remote wireless interfaces implemented in the elder care smart home environment according to these aspects of this invention. According to further steps of this use method, the attending doctor is promptly notified, and vital signs of the patient are then transmitted in real time via the patch to the hospital, the doctor's office, and/or to the paramedics in the ambulance that has been dispatch to the patient's location. To add further functionality to the elder care patch, the device may be advantageously equipped with a GPS locator so that in the event the users is unable to communicate his location to health officials, his location can be determined by the GPS locator and then communicated by wireless transmission within the smart home environment and any networks associated therewith.

Concluding Aspects and Applications

It is presently contemplated by the inventors hereof that certain aspects of the present invention may be implemented in a personal diagnostic device that is employed in the related fields of mental health and brain and cognitive sciences. In this application of the present invention, the inventors contemplate a bio-patch or bio-bracelet that can monitor the brain activity and function of a user and/or related signals in the user's nervous system.

In the case when a patient feels fear, sadness, or depression; detecting purely physiological parameters like blood pressure and heart rate that are associated with such mental states may be performed by the patch technologies disclosed and discussed herein. In addition thereto, the inventors hereof propose that patterns of mental processes and nervous reactions may be detected by the bio-patches and bio-bracelets and utilized in combination with detected biological and physiological parameters to thereby further treat patients in a more comprehensive manner.

The Brain Engineering Laboratory at the University of California at Irvine (UCI) has as its goal the attainment of a fundamental understanding of the brain, its mechanisms, operation, and behaviors. There has been explosive growth of information about the brain from a broad range of fields including neuro-anatomy, physiology, biochemistry and behavior, and tools from mathematics, computer science, and engineering are brought to bear to make sense of the voluminous data. The UCI lab and others investigate detailed designs of real brain areas, taking advantage of the explosion of new data and insights from the growing fields of neurobiology.

The UCI researchers have found that previously ignored details of the anatomical wiring diagrams and physiological operating mechanisms of brain circuits suggest powerful algorithms that differ substantially from those in neural networks, and were unexpected from psychological or neuroscience studies. For example, the UCI models of superficial cortical layers perform the unexpectedly complex task of hierarchical clustering. See for example, Ambros-Ingerson, J., Granger, R., and Lynch, G. (1990); Simulation of Paleocortex Performs Hierarchical Clustering, Science vol. 247, pgs 1344-1348.

The UCI algorithms derived from various brain areas have turned out to be so unexpectedly effective and efficient that they have found use in a variety of real-world applications. A hardware and software system derived from the UCI cortical models has been used to analyze EEG data in normal and early Alzheimer's subjects, as a potential device for aiding clinicians in the early detection of Alzheimer's Disease. See, Benvenuto, J., Jin, Y., Casale, M., Lynch, G., Granger, R. (2002), Identification of Diagnostic Evoked Response Potential Segments in Alzheimeris Disease, Exper. Neurology, 176: 269-276; and Granger, R. (2001), Method and Computer Program Product for Assessing Neurological Conditions and Treatments using Evoked Response Potentials, U.S. Pat. No. 6,223,074.

At the Massachusetts Institute of Technology (MIT), researchers in the Brain and Cognitive Sciences Department are exploring how cellular and molecular neuroscience may be employed to understand the brain at its most fundamental level by examining the basic elements of the nervous system. They have determined that the interplay of the complex molecular machinery of the neuronal membrane with the dynamics of electrical potentials is critical to understanding the synaptic contacts where neurons communicate with each other. Such understanding may advantageously be applied to the inventions disclosed herein.

Thus in view of the basic research and experimental work currently being performed in the fields of cognitive and brain sciences at several leading academic institutions, such as UCI and MIT for example, the inventors hereof contemplate useful applications for the present bio-patch and bio-bracelet in the realm of mental health and brain sciences which heretofore have not been contemplated by any artisan endeavoring in the various arts related hereto. For example, the inventors hereof contemplate that once the signals of the brain are well understood, an implementation of the present inventions may include detection of such signals which may then be converted to useful results in wireless networks such as those described above in connection with the stress patch, controlled drug release patches, and elderly cares patches.

If not so specifically incorporated herein, all patents, patent applications, and other publications mentioned, cited, or otherwise referred to in this specification are hereby expressly incorporated herein by reference in their entireties.

And while this invention has been described in detail with reference to certain preferred embodiments, it should be appreciated that the present invention is not limited to those precise embodiments. Rather, in view of the present disclosure which describes the current best mode for practicing the invention, many modifications and variations would present themselves to those of skill in the art without departing from the scope and spirit of this invention. For example, the bio-patch implementation may be made to conform to any particular surface area of the body and is not intended to necessarily be limited to a rectangular shape for use on the wrist areas. Any number of different size and shape configurations would be applicable. The bio-patch may also have pre-defined contours to promote adhesion with the body surface for use, for example, on the lower back, lower neck, shoulder, chest area, or skull. Similarly, many of the individual layers and layer components such as the fluidic circuits, the processors and controllers, wash buffer reservoirs, drug or hormone release reservoirs, valves, fluid channels, detectors, emitters, and electrodes, for example, are not necessarily restricted to the placements or locations shown but rather may alternatively be located on any suitable layer or otherwise combined on single layers to achieve the intended functions and results hereof.

The scope of the invention is, therefore, indicated by the following claims rather than by the foregoing description. All changes, modifications, and variations coming within the meaning and range of equivalency of the claims are to be considered within their scope.

What is claimed is:

1. A personal diagnostic patch device having multiple layers for analysis of a blood sample, said personal diagnostic patch device comprising:
a patch that is configured to be worn by a user on a skin surface, said patch having multiple layers;
a sample acquisition layer on a first layer of said patch that obtains blood samples from said user, said sample acquisition layer comprising a plurality of tubules and valves;
a fluidic processing layer on a second layer of said patch above said first layer, said fluidic processing layer having a plurality of fluidic circuits, each of said plurality of fluidic circuits having a reservoir opening that is in register with at least one of said plurality of tubules and valves in said first layer;
an assay results detection layer on a third layer of said patch above said second layer, said assay results detection layer including a bottom surface that covers said reservoir opening of each of said plurality of fluidic circuits to form at least a metering chamber for each of said plurality of fluidic circuits, said metering chamber for each of said plurality of fluidic circuits having glucose oxidase, said assay results detection layer further having a plurality of detectors therein, one or more of said plurality of detectors having electrodes that contact a blood sample in said metering chamber of each of said plurality of fluidic circuits to detect glucose electrochemically;
said sample acquisition layer configured to direct at a first time, at least a first blood sample from a first tubule to a first metering chamber by controlling a first valve and closing said first metering chamber with a second valve when said first blood sample reaches a predetermined level, said sample acquisition layer further configured to direct at a second time, at least a second blood sample from a second tubule to a second metering chamber by controlling a third valve and closing said second metering chamber with a fourth valve when said second blood sample reaches a predetermined level, said second time occurring after said first time;
an insulin reservoir on said patch comprising at least first and second time-release reservoirs, said first and second time-release reservoirs in fluid communication with one or more dispensing nozzles on said patch that deliver insulin from said first and second time-release reservoirs to said user wearing said patch; and
a logic controller on said patch that directs delivery of said insulin in said first time-release reservoir to said one or more dispensing nozzles based on assay results associated with said first blood sample, said logic controller further directs delivery of said insulin in said second time-release reservoir to said one or more dispensing nozzles based on assay results associated with said second blood sample.

2. The personal diagnostic patch device according to claim 1 wherein said reservoir opening in each of said plurality of fluidic circuits is further connected to at least a cell separation pad and a reaction pad, said cell separation pad partially removes blood cells before said blood sample reaches said reaction pad, said reaction pad contains at least a peroxidase with one or more optical emitters below said reaction pad and at least one optical detector in the assay results detection layer above said reaction pad.

3. The personal diagnostic patch device according to claim 1 wherein said metering chamber of each of said plurality of fluidic circuits comprises a vacuum.

4. The personal diagnostic patch device according to claim 1 further comprising hydrophobic surfaces for varying fluid flow.

5. The personal diagnostic patch device according to claim 1 wherein said logic controller is part of a logic processing system with an internet protocol address.

6. The personal diagnostic patch device according to claim 1 further comprising a receiver and a transmitter to provide telemetry information regarding location of said user.

7. The personal diagnostic patch device according to claim 1 further comprising a signal processing unit that wirelessly transmits an electronic signal including at least some information about diagnostic results to a remote location.

8. The personal diagnostic patch device according to claim 1 further comprising an interface that communicates with a computer device remotely maintained from said personal diagnostic patch device, said computer device comprising at least one of the group consisting of: a desk top computer, a lap top computer, a hand-held computer, a receiver that receives at least some information about said diagnostic results, a receiver that receives at least some of said information about said diagnostic results wirelessly, a monitor that displays at least some of said information about said diagnostic results.

9. The personal diagnostic patch device according to claim 1 further comprising a signal processing unit, said signal processing unit comprising an address so that said personal diagnostic patch device is addressable remotely over a network.

10. The personal diagnostic patch device according to claim 1 wherein one or more of said plurality of detectors comprise at least one of the group consisting of: a charged coupled device (CCD), at least one light receiving nano-wire, and a semi-conductor light detecting material.

11. The personal diagnostic patch device according to claim 1 further comprising at least one drug-release reservoir having supply probes that penetrate into said user to release a pre-determined amount of liquid medication from said at least one drug-release reservoir into said user through said supply probes.

12. The personal diagnostic patch device according to claim 2 wherein said reaction pad is in register with said one or more optical emitters below said reaction pad and in register with said at least one optical detector above said reaction pad.

13. The personal diagnostic patch device according to claim 12 wherein at least one of said one or more optical emitters is a micro-wire emitter located in said sample acquisition layer.

14. The personal diagnostic patch device according to claim 13 wherein said electrodes are micro-wire detectors located in said assay results detection layer.

15. The personal diagnostic patch device according to claim 1 wherein said fluidic processing layer is between 25 microns and 500 microns thick.

16. The personal diagnostic patch device according to claim 1 wherein said sample acquisition layer is 100 microns thick.

17. The personal diagnostic patch device according to claim 1 wherein at least one metering chamber is 200 microns thick.

18. The personal diagnostic patch device according to claim 1 wherein said first valve comprises a first heating element and a first melt plug.

19. The personal diagnostic patch device according to claim 1 wherein said first valve comprises dissolvable plug that is activated when it comes in contact with a liquid.

20. The personal diagnostic patch device according to claim 1 wherein said second valve comprises a pinch valve.

* * * * *